(12) United States Patent
Alvarez et al.

(10) Patent No.: US 10,881,741 B2
(45) Date of Patent: *Jan. 5, 2021

(54) SINGLE CHAIN FC FUSION PROTEINS

(71) Applicant: Alkermes, Inc., Waltham, MA (US)

(72) Inventors: Juan Alvarez, Lincoln, MA (US);
Demetri T. Moustakas, Belmont, MA (US); Heather R. Brodkin, Warwick, RI (US); Leslie A. McSweeney, Milford, MA (US)

(73) Assignee: Alkermes, Inc., Waltham, MA (US)

( * ) Notice: Subject to any disclaimer, the term of this patent is extended or adjusted under 35 U.S.C. 154(b) by 331 days.

This patent is subject to a terminal disclaimer.

(21) Appl. No.: 15/949,596

(22) Filed: Apr. 10, 2018

(65) Prior Publication Data

US 2018/0289825 A1    Oct. 11, 2018

Related U.S. Application Data

(63) Continuation of application No. 14/974,114, filed on Dec. 18, 2015, now abandoned.

(60) Provisional application No. 62/094,242, filed on Dec. 19, 2014.

(51) Int. Cl.

| | | |
|---|---|---|
| *C07K 14/54* | (2006.01) |
| *C07K 14/715* | (2006.01) |
| *A61K 38/20* | (2006.01) |
| *A61K 47/64* | (2017.01) |
| *A61K 47/68* | (2017.01) |
| *A61P 17/06* | (2006.01) |
| *A61P 35/00* | (2006.01) |
| *A61P 37/02* | (2006.01) |
| *A61P 37/06* | (2006.01) |
| *A61P 43/00* | (2006.01) |
| *A61K 38/17* | (2006.01) |
| *A61K 38/21* | (2006.01) |
| *A61K 38/48* | (2006.01) |
| *C07K 14/55* | (2006.01) |
| *C07K 14/565* | (2006.01) |
| *C07K 14/705* | (2006.01) |
| *C12N 9/64* | (2006.01) |
| *A61K 38/00* | (2006.01) |

(52) U.S. Cl.
CPC ............ *A61K 47/64* (2017.08); *A61K 38/179* (2013.01); *A61K 38/1793* (2013.01); *A61K 38/2013* (2013.01); *A61K 38/2066* (2013.01); *A61K 38/215* (2013.01); *A61K 38/4846* (2013.01); *C07K 14/5428* (2013.01); *C07K 14/55* (2013.01); *C07K 14/565* (2013.01); *C07K 14/70578* (2013.01); *C07K 14/7151* (2013.01); *C07K 14/7155* (2013.01); *C12N 9/644* (2013.01); *A61K 38/00* (2013.01); *C07K 2319/30* (2013.01); *C07K 2319/70* (2013.01); *C12Y 304/21022* (2013.01)

(58) Field of Classification Search
CPC ............ A61K 47/6803; A61K 38/2066; A61K 47/64; C07K 14/5428; C07K 14/7155; C07K 2319/30; A61P 35/00; A61P 37/02; A61P 37/06; A61P 43/00
See application file for complete search history.

(56) References Cited

U.S. PATENT DOCUMENTS

| | | |
|---|---|---|
| 6,428,985 B1 | 8/2002 | Bromberg et al. |
| 7,696,322 B2 | 4/2010 | Bleck et al. |
| 8,063,182 B1 | 11/2011 | Brockhaus et al. |
| 8,163,522 B1 | 4/2012 | Brockhaus et al. |
| 2002/0127227 A1 | 9/2002 | Holmes et al. |
| 2005/0069552 A1 | 3/2005 | Bleck et al. |
| 2010/0227394 A1 | 9/2010 | Bleck et al. |
| 2010/0285014 A1 | 11/2010 | Cox, III et al. |

(Continued)

FOREIGN PATENT DOCUMENTS

| | | |
|---|---|---|
| CN | 101962413 A | 2/2011 |
| JP | 2003508023 A | 3/2003 |

(Continued)

OTHER PUBLICATIONS

Linderholm, A.L., et al., "Immunoglobulin Fc-Fusion Proteins Part 2: Therapeutic Uses and Clinical Development," Bioprocess International, vol. 12(10): pp. 2-7, Nov. 2014.
Vallee, S., et al., "Pulmonary Administration of Interferon Beta-1a-Fc Fusion Protein in Non-Human Primates Using an Immunoglobulin Transport Pathway," Journal of Interferon and Cytokine Research, vol. 32(4): pp. 178-184 (Apr. 2012).

(Continued)

*Primary Examiner* — Vanessa L. Ford
*Assistant Examiner* — Bruce D. Hissong
(74) *Attorney, Agent, or Firm* — Lathrop GPM LLP; Andrew T. Wilkins; Michael J. Spellberg

(57) ABSTRACT

The present invention provides novel, single chain Fc fusion proteins having improved properties. The invention provides single chain fusions of soluble proteins fused to the Fc region of an immunoglobulin via a novel linker comprising a constant region of an immunoglobulin light chain linked to a CH1 constant region of an immunoglobulin heavy chain. This novel linker confers favorable properties on the Fc fusion proteins of the invention such as improved bioactivity and increased half-life as compared to non-Fc fusion counterparts or as compared to prior art Fc fusion proteins. The novel Fc fusion protein scaffold as described herein may be designed to include soluble proteins of interest capable of binding or interacting with any target of interest. Preferably, the Fc fusion protein of the invention is a dimer. The dimer preferably forms via a disulfide bond between free cysteine residues in the hinge region of two monomeric Fc fusion proteins of the invention.

15 Claims, 21 Drawing Sheets

Specification includes a Sequence Listing.

(56) References Cited

U.S. PATENT DOCUMENTS

| | | | |
|---|---|---|---|
| 2013/0217864 | A1 | 8/2013 | Cho et al. |
| 2013/0295084 | A1 | 11/2013 | Hunter et al. |
| 2013/0316404 | A1 | 11/2013 | Roers et al. |
| 2013/0336925 | A1 | 12/2013 | Alvarez et al. |
| 2014/0056895 | A1 | 2/2014 | Baurin et al. |
| 2014/0072581 | A1 | 3/2014 | Dixit et al. |
| 2014/0234962 | A1 | 8/2014 | Alvarez |
| 2015/0071948 | A1 | 3/2015 | Lazar et al. |
| 2016/0068583 | A1 | 3/2016 | McCauley et al. |
| 2016/0175458 | A1 | 6/2016 | Alvarez et al. |
| 2018/0289825 | A1 | 10/2018 | Alvarez et al. |

FOREIGN PATENT DOCUMENTS

| | | |
|---|---|---|
| WO | 0103737 A1 | 1/2001 |
| WO | 0158950 A1 | 8/2001 |
| WO | 2004101740 A2 | 11/2004 |
| WO | 2008140595 A2 | 11/2008 |
| WO | 2011076781 A1 | 6/2011 |
| WO | 2011090762 A1 | 7/2011 |
| WO | 2011122923 A2 | 10/2011 |
| WO | 2012146628 A1 | 11/2012 |
| WO | 2012178137 A1 | 12/2012 |
| WO | 2013026833 A1 | 2/2013 |
| WO | 2013184942 A1 | 12/2013 |
| WO | 2014018572 A2 | 1/2014 |
| WO | 2014023673 A1 | 2/2014 |
| WO | 2014151910 A1 | 9/2014 |
| WO | 2015017548 A2 | 2/2015 |
| WO | 2015117930 A1 | 8/2015 |
| WO | 2016082677 A1 | 6/2016 |
| WO | 2016100788 A1 | 6/2016 |
| WO | 2017165464 A1 | 9/2017 |
| WO | 2018/005226 A3 | 1/2018 |
| WO | 2018005226 A3 | 4/2018 |

OTHER PUBLICATIONS

Zheng, X., et al., "Administration of Noncytolytic IL-10/Fc in Murine Models of Lipopolysaccharide-Induced Septic Shock and Allogeneic Islet Transplantation," The Journal of Immunology, The American Association of Immunologists, 154(10): pp. 5590-5600 (May 1995).

Zheng, X., et al., "A Noncytolytic IL-10/Fc Fusion Protein Prevents Diabetes, Blocks Autoimmunity, and Promotes Suppressor Phenomena in NOD Mice," The Journal of Immunology, The American Association of Immunologists, vol. 158(9); pp. 4507-4513 (May 1997).

Zheng, X., et al., "IL-2 Receptor-Targeted Cytolytic IL-2/FC Fusion Protein Treatment Blocks Diabetogenic Autoimmunity in Nonobese Diabetic Mice," The Journal of Immunology, The American Association of Immunologists, 163(7): pp. 4041-4048 (Oct. 1999).

Czajkowsky, D.M., et al., "Fc-Fusion Proteins: New Developments and Future Perspectives," EMBO Molecular Medicine, vol. 4(10): pp. 1015-1028 (Jul. 2012).

Wu, B., et al., "Pharmacokinetics of Peptide-Fc Fusion Proteins," Journal of Pharmaceutical Sciences, vol. 103(1): pp. 53-64 (Jan. 2014).

Shimamoto, G., et al., "Peptibodies A Flexible Alternative Format to Antibodies," MABS, vol. 4(5): pp. 586-591 (Sep. 2012).

Ding, Y. et al., "A Single Amino Acid Determines the Immunostimulatory Activity of Interleukin 10", J. Exp. Med., 191(2), Jan. 2000, 213-223.

Vallee, S. et al., "Pulmonary Administration of Interferon Beta-1a-Fc Fusion Protein in Non-Human Primates Using an Immunoglobulin Transport Pathway", Journal of Interferon and Cytokine Research, vol. 32, No. 4, Apr. 1, 2012, 178-184.

Yoon, S. et al., "Conformational changes mediate interleukin-10 receptor 2 (IL-10R2) binding to IL-10 and assembly of the signaling complex", J Biol Chem., 281(46), 2006, 35088-96.

Zhao, L. et al., "Eradication of non-Hodgkin lymphoma through the induction of tumor-specific T-cell immunity by CD20-Flex BiFP", Blood, 122(26), 2013, 4230-6.

SEQUENCE LISTING

```
<160> NUMBER OF SEQ ID NOS: 27

<210> SEQ ID NO 1
<211> LENGTH: 107
<212> TYPE: PRT
<213> ORGANISM: Homo sapiens

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105

<210> SEQ ID NO 2
<211> LENGTH: 98
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 3
<211> LENGTH: 330
```

```
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Glu Pro Lys Ser Ser Asp Lys Thr His Thr Cys Pro Pro Cys Pro
1               5                   10                  15

<210> SEQ ID NO 5
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 6
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Gln Val Lys Phe Asn Trp Tyr Val
 50                  55                  60

Asp Gly Val Gln Val His Asn Ala Lys Thr Lys Pro Arg Glu Gln Gln
 65                  70                  75                  80

Tyr Asn Ser Thr Tyr Arg Val Val Ser Val Leu Thr Val Leu His Gln
                 85                  90                  95

Asn Trp Leu Asp Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 7
<211> LENGTH: 900
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Thr Val Phe Leu Asp His Glu Asn Ala Asn Lys Ile Leu Asn Arg Pro
1               5                   10                  15

Lys Arg Tyr Asn Ser Gly Lys Leu Glu Glu Phe Val Gln Gly Asn Leu
            20                  25                  30

Glu Arg Glu Cys Met Glu Glu Lys Cys Ser Phe Glu Glu Ala Arg Glu
        35                  40                  45

Val Phe Glu Asn Thr Glu Arg Thr Thr Glu Phe Trp Lys Gln Tyr Val
 50                  55                  60

Asp Gly Asp Gln Cys Glu Ser Asn Pro Cys Leu Asn Gly Gly Ser Cys
 65                  70                  75                  80

Lys Asp Asp Ile Asn Ser Tyr Glu Cys Trp Cys Pro Phe Gly Phe Glu
                 85                  90                  95

Gly Lys Asn Cys Glu Leu Asp Val Thr Cys Asn Ile Lys Asn Gly Arg
            100                 105                 110

Cys Glu Gln Phe Cys Lys Asn Ser Ala Asp Asn Lys Val Val Cys Ser
        115                 120                 125

Cys Thr Glu Gly Tyr Arg Leu Ala Glu Asn Gln Lys Ser Cys Glu Pro
130                 135                 140

Ala Val Pro Phe Pro Cys Gly Arg Val Ser Val Ser Gln Thr Ser Lys
145                 150                 155                 160

Leu Thr Arg Ala Glu Thr Val Phe Pro Asp Val Asp Tyr Val Asn Ser
                165                 170                 175

```
Thr Glu Ala Glu Thr Ile Leu Asp Asn Ile Thr Gln Ser Thr Gln Ser
            180                 185                 190

Phe Asn Asp Phe Thr Arg Val Val Gly Gly Glu Asp Ala Lys Pro Gly
        195                 200                 205

Gln Phe Pro Trp Gln Val Val Leu Asn Gly Lys Val Asp Ala Phe Cys
    210                 215                 220

Gly Gly Ser Ile Val Asn Glu Lys Trp Ile Val Thr Ala Ala His Cys
225                 230                 235                 240

Val Glu Thr Gly Val Lys Ile Thr Val Val Ala Gly Glu His Asn Ile
                245                 250                 255

Glu Glu Thr Glu His Thr Glu Gln Lys Arg Asn Val Ile Arg Ile Ile
            260                 265                 270

Pro His His Asn Tyr Asn Ala Ala Ile Asn Lys Tyr Asn His Asp Ile
        275                 280                 285

Ala Leu Leu Glu Leu Asp Glu Pro Leu Val Leu Asn Ser Tyr Val Thr
    290                 295                 300

Pro Ile Cys Ile Ala Asp Lys Glu Tyr Thr Asn Ile Phe Leu Lys Phe
305                 310                 315                 320

Gly Ser Gly Tyr Val Ser Gly Trp Gly Arg Val Phe His Lys Gly Arg
                325                 330                 335

Ser Ala Leu Val Leu Gln Tyr Leu Arg Val Pro Leu Val Asp Arg Ala
            340                 345                 350

Thr Cys Leu Arg Ser Thr Lys Phe Thr Ile Tyr Asn Asn Met Phe Cys
        355                 360                 365

Ala Gly Phe His Glu Gly Gly Arg Asp Ser Cys Gln Gly Asp Ser Gly
    370                 375                 380

Gly Pro His Val Thr Glu Val Glu Gly Thr Ser Phe Leu Thr Gly Ile
385                 390                 395                 400

Ile Ser Trp Gly Glu Glu Cys Ala Met Lys Gly Lys Tyr Gly Ile Tyr
                405                 410                 415

Thr Lys Val Ser Arg Tyr Val Asn Trp Ile Lys Glu Lys Thr Lys Leu
            420                 425                 430

Thr Gly Gly Gly Ser Gly Gly Gly Ser Arg Thr Val Ala Ala
        435                 440                 445

Pro Ser Val Phe Ile Phe Pro Pro Ser Asp Glu Gln Leu Lys Ser Gly
    450                 455                 460

Thr Ala Ser Val Val Cys Leu Leu Asn Asn Phe Tyr Pro Arg Glu Ala
465                 470                 475                 480

Lys Val Gln Trp Lys Val Asp Asn Ala Leu Gln Ser Gly Asn Ser Gln
                485                 490                 495

Glu Ser Val Thr Glu Gln Asp Ser Lys Asp Ser Thr Tyr Ser Leu Ser
            500                 505                 510

Ser Thr Leu Thr Leu Ser Lys Ala Asp Tyr Glu Lys His Lys Val Tyr
        515                 520                 525

Ala Cys Glu Val Thr His Gln Gly Leu Ser Ser Pro Val Thr Lys Ser
    530                 535                 540

Phe Asn Arg Gly Glu Ser Gly Gly Gly Ser Gly Gly Gly Ser
545                 550                 555                 560

Gly Gly Gly Gly Ser Gly Gly Gly Ser Ala Ser Thr Lys Gly Pro
                565                 570                 575

Ser Val Phe Pro Leu Ala Pro Ser Ser Lys Ser Thr Ser Gly Gly Thr
            580                 585                 590
```

Ala Ala Leu Gly Cys Leu Val Lys Asp Tyr Phe Pro Glu Pro Val Thr
                595                 600                 605

Val Ser Trp Asn Ser Gly Ala Leu Thr Ser Gly Val His Thr Phe Pro
            610                 615                 620

Ala Val Leu Gln Ser Ser Gly Leu Tyr Ser Leu Ser Ser Val Val Thr
625                 630                 635                 640

Val Pro Ser Ser Ser Leu Gly Thr Gln Thr Tyr Ile Cys Asn Val Asn
                645                 650                 655

His Lys Pro Ser Asn Thr Lys Val Asp Lys Arg Val Glu Pro Lys Ser
            660                 665                 670

Ser Asp Lys Thr His Thr Cys Pro Pro Cys Pro Ala Pro Glu Leu Leu
675                 680                 685

Gly Gly Pro Ser Val Phe Leu Phe Pro Pro Lys Pro Lys Asp Thr Leu
            690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
            740                 745                 750

Tyr Arg Val Val Ser Val Leu Thr Val Leu His Gln Asp Trp Leu Asn
            755                 760                 765

Gly Lys Glu Tyr Lys Cys Lys Val Ser Asn Lys Ala Leu Pro Ala Pro
            770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Glu Glu Met Thr Lys Asn Gln Val
                805                 810                 815

Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
            835                 840                 845

Pro Val Leu Asp Ser Asp Gly Ser Phe Phe Leu Tyr Ser Lys Leu Thr
850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900

<210> SEQ ID NO 8
<211> LENGTH: 702
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

```
Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Gly Gly Ser
225                 230                 235                 240

Gly Gly Gly Gly Ser Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
    290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Ser
            340                 345                 350

Gly Gly Gly Gly Ser Gly Gly Gly Gly Ser Gly Gly Gly Gly Ser Gly
        355                 360                 365

Gly Gly Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
        435                 440                 445

Gly Thr Gln Thr Tyr Ile Cys Asn Val Asn His Lys Pro Ser Asn Thr
    450                 455                 460
```

Lys Val Asp Lys Arg Val Glu Pro Lys Ser Cys Asp Lys Thr His Thr
465                 470                 475                 480

Cys Pro Pro Cys Pro Ala Pro Glu Leu Leu Gly Gly Pro Ser Val Phe
            485                 490                 495

Leu Phe Pro Pro Lys Pro Lys Asp Thr Leu Met Ile Ser Arg Thr Pro
            500                 505                 510

Glu Val Thr Cys Val Val Val Asp Val Ser His Glu Asp Pro Gln Val
            515                 520                 525

Lys Phe Asn Trp Tyr Val Asp Gly Val Gln Val His Asn Ala Lys Thr
    530                 535                 540

Lys Pro Arg Glu Gln Gln Tyr Asn Ser Thr Tyr Arg Val Val Ser Val
545                 550                 555                 560

Leu Thr Val Leu His Gln Asn Trp Leu Asp Gly Lys Glu Tyr Lys Cys
                565                 570                 575

Lys Val Ser Asn Lys Ala Leu Pro Ala Pro Ile Glu Lys Thr Ile Ser
                580                 585                 590

Lys Ala Lys Gly Gln Pro Arg Glu Pro Gln Val Tyr Thr Leu Pro Pro
    595                 600                 605

Ser Arg Glu Glu Met Thr Lys Asn Gln Val Ser Leu Thr Cys Leu Val
610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Tyr Ser Lys Leu Thr Val Asp Lys Ser Arg Trp
                660                 665                 670

Gln Gln Gly Asn Val Phe Ser Cys Ser Val Met His Glu Ala Leu His
                675                 680                 685

Asn His Tyr Thr Gln Lys Ser Leu Ser Leu Ser Pro Gly Lys
                690                 695                 700

<210> SEQ ID NO 9
<211> LENGTH: 618
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

-continued

```
Gln Pro Val Ser Leu Thr Asn Met Pro Asp Glu Gly Val Met Val Thr
    130                 135                 140
Lys Phe Tyr Phe Gln Glu Asp Glu Gly Gly Gly Ser Gly Gly Gly
145                 150                 155                 160
Gly Ser Arg Thr Val Ala Ala Pro Ser Val Phe Ile Phe Pro Pro Ser
                165                 170                 175
Asp Glu Gln Leu Lys Ser Gly Thr Ala Ser Val Val Cys Leu Leu Asn
            180                 185                 190
Asn Phe Tyr Pro Arg Glu Ala Lys Val Gln Trp Lys Val Asp Asn Ala
        195                 200                 205
Leu Gln Ser Gly Asn Ser Gln Glu Ser Val Thr Glu Gln Asp Ser Lys
    210                 215                 220
Asp Ser Thr Tyr Ser Leu Ser Ser Thr Leu Thr Leu Ser Lys Ala Asp
225                 230                 235                 240
Tyr Glu Lys His Lys Val Tyr Ala Cys Glu Val Thr His Gln Gly Leu
                245                 250                 255
Ser Ser Pro Val Thr Lys Ser Phe Asn Arg Gly Glu Ser Gly Gly Gly
            260                 265                 270
Ser Gly Gly Gly Ser Gly Gly Gly Ser Gly Gly Gly Ser
        275                 280                 285
Ala Ser Thr Lys Gly Pro Ser Val Phe Pro Leu Ala Pro Ser Ser Lys
    290                 295                 300
Ser Thr Ser Gly Gly Thr Ala Ala Leu Gly Cys Leu Val Lys Asp Tyr
305                 310                 315                 320
Phe Pro Glu Pro Val Thr Val Ser Trp Asn Ser Gly Ala Leu Thr Ser
                325                 330                 335
Gly Val His Thr Phe Pro Ala Val Leu Gln Ser Ser Gly Leu Tyr Ser
            340                 345                 350
Leu Ser Ser Val Val Thr Val Pro Ser Ser Ser Leu Gly Thr Gln Thr
        355                 360                 365
Tyr Ile Cys Asn Val Asn His Lys Pro Ser Asn Thr Lys Val Asp Lys
    370                 375                 380
Arg Val Glu Pro Lys Ser Ser Asp Lys Thr His Thr Cys Pro Pro Cys
385                 390                 395                 400
Pro Ala Pro Glu Leu Leu Gly Gly Pro Ser Val Phe Leu Phe Pro Pro
                405                 410                 415
Lys Pro Lys Asp Thr Leu Met Ile Ser Arg Thr Pro Glu Val Thr Cys
            420                 425                 430
Val Val Val Asp Val Ser His Glu Asp Pro Glu Val Lys Phe Asn Trp
        435                 440                 445
Tyr Val Asp Gly Val Glu Val His Asn Ala Lys Thr Lys Pro Arg Glu
    450                 455                 460
Glu Gln Tyr Asn Ser Thr Tyr Arg Val Val Ser Val Leu Thr Val Leu
465                 470                 475                 480
His Gln Asp Trp Leu Asn Gly Lys Glu Tyr Lys Cys Lys Val Ser Asn
                485                 490                 495
Lys Ala Leu Pro Ala Pro Ile Glu Lys Thr Ile Ser Lys Ala Lys Gly
            500                 505                 510
Gln Pro Arg Glu Pro Gln Val Tyr Thr Leu Pro Pro Ser Arg Glu Glu
        515                 520                 525
Met Thr Lys Asn Gln Val Ser Leu Thr Cys Leu Val Lys Gly Phe Tyr
    530                 535                 540
```

```
Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Tyr Ser Lys Leu Thr Val Asp Lys Ser Arg Trp Gln Gln Gly Asn
            580                 585                 590

Val Phe Ser Cys Ser Val Met His Glu Ala Leu His Asn His Tyr Thr
        595                 600                 605

Gln Lys Ser Leu Ser Leu Ser Pro Gly Lys
    610                 615

<210> SEQ ID NO 10
<211> LENGTH: 20
<212> TYPE: PRT
<213> ORGANISM: Unknown
<220> FEATURE:
<223> OTHER INFORMATION: Description of Unknown:
      N-terminal leader sequence

<400> SEQUENCE: 10

Met Tyr Arg Met Gln Leu Leu Ser Cys Ile Ala Leu Ser Leu Ala Leu
1               5                   10                  15

Val Thr Asn Ser
            20

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly Ser
1               5                   10

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Gly Gly Gly Ser Gly Gly Gly Gly Ser Gly
1               5                   10                  15

Gly Gly Gly Ser
            20

<210> SEQ ID NO 13
<211> LENGTH: 2760
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgtaccgga tgcagctgct gagctgtatc gccctgtctc tggccctcgt gaccaacagc        60
accgtgtttc tggaccacga gaacgccaac aagatcctga ccggcccaa gcggtacaac       120 agcggcaagc tggaagagtt cgtgcagggc aacctggaac gcgagtgcat ggaagagaag       180
```

-continued

```
tgcagcttcg aagaggccag agaggtgttc gagaacaccg agcggaccac cgagttctgg      240
aagcagtacg tggacggcga ccagtgcgag agcaacccct gtctgaatgg cggcagctgc      300
aaggacgaca tcaacagcta cgagtgctgg tgccccttcg gcttcgaggg caagaactgc      360
gagctggacg tgacctgcaa catcaagaac ggcagatgcg agcagttctg caagaacagc      420
gccgacaaca aggtcgtgtg ctcctgcacc gagggctaca actggccgga aaccagaag      480 tcctgcgagc ccgccgtgcc tttcccatgt ggaagagtgt ccgtgtccca gaccagcaag      540
ctgaccagag ccgagacagt gttccccgac gtggactacg tgaactccac cgaggccgag      600
acaatcctgg acaacatcac ccagagcacc cagtccttca cgacttcac cagagtcgtg       660 ggcggcgagg atgccaagcc tggacagttc ccgtggcagg tggtgctgaa cggaaaggtg      720
gacgcctttt gcggcggcag catcgtgaac gagaagtgga tcgtgacagc cgcccactgc      780
gtggaaaccg gcgtgaagat tacagtggtg gccggcgagc acaacatcga ggaaaccgag      840
cacacagagc agaaacggaa cgtgatcaga atcatccccc accacaacta caacgccgcc      900
atcaacaagt acaaccacga cattgccctg ctggaactgg acgagcccct ggtgctgaat      960
agctacgtga ccccccatctg cattgccgac aaagagtaca ccaacatctt tctgaagttc     1020
ggcagcggct acgtgtccgg ctggggcaga gtgtttcaca agggcagatc cgctctggtg      1080
ctgcagtacc tgagagtgcc tctggtggac cgggccacct gtctgagaag caccaagttc      1140
accatctaca acaacatgtt ctgcgccggc ttccatgagg gcggcagaga tagctgtcag      1200
ggcgattctg gcggccctca cgtgacagaa gtggaaggca ccagctttct gaccggcatc      1260
atcagctggg gcgaggaatg cgccatgaag gggaagtacg gcatctacac caaggtgtcc      1320
agatatgtga actggatcaa agaaaagacc aagctgacag gcggcggagg ctctggcgga      1380
ggcggatcta gaacagtggc cgctcccagc gtgttcatct tcccacctag cgacgagcag      1440
ctgaagtccg gcacagcctc tgtcgtgtgc ctgctgaaca acttctaccc cgcgaggcc      1500 aaggtgcagt ggaaggtgga caatgccctg cagagcggca cagccagga aagcgtgacc      1560 gagcaggaca gcaaggactc cacctacagc ctgagcagca gcctgaccct gagcaaggcc      1620
gactacgaga agcacaaggt gtacgcctgc gaagtgaccc accagggcct gtctagccca      1680
gtgaccaaga gcttcaaccg gggcgaatct ggggcggag gatcaggcgg gggaggaagt       1740 ggggagggg gaagcggagg gggaggatct gcctctacaa agggccctag cgtgttcccc       1800
ctggccccta gcagcaagtc tacaagcgga ggcacagctg ccctgggctg cctcgtgaag     1860
gactacttcc ctgagcccgt gaccgtgtcc tggaacagcg gagcactgac aagcggcgtg      1920
cacacctttc cagccgtgct gcagagcagc ggcctgtact ctctgagcag cgtcgtgaca     1980
gtgcccagca gctctctggg cacccagacc tacatctgca acgtgaacca caagcccagc    2040
aataccaaag tggacaagcg ggtggaaccc aagagcagcg acaagaccca cacctgtccc     2100
ccttgtcctg ccccgaact gctgggaggc cttccgtgt tcctgttccc cccaaagccc       2160
aaggacaccc tgatgatcag ccggacccct gaagtgacct gcgtggtggt ggatgtgtcc    2220
cacgaggacc cagaagtgaa gttcaattgg tatgtggacg gggtggaagt gcacaacgcc    2280
aagaccaaac ccagagagga acagtacaat agcacctacc gggtggtgtc cgtgctgaca     2340
gtgctgcacc aggactggct gaatggcaaa gagtataagt gcaaagtgtc caacaaggcc    2400
ctgcctgccc ccatcgagaa aaccatcagc aaggccaagg gccagccccg cgaaccccag     2460
gtgtacacac tgcccccaag ccgggaagag atgaccaaga ccaggtgtc cctgacctgt     2520
```

```
ctcgtgaaag gcttctaccc ttccgatatc gccgtggaat gggagagcaa cggccagccc    2580
gagaacaatt acaagaccac ccccctgtg ctggactccg acggctcatt cttcctgtac    2640
agcaaactga ccgtggacaa gagccggtgg cagcaggaa acgtgttcag ctgcagcgtg    2700
atgcacgagg ccctgcacaa ccactacacc cagaaaagcc tgagcctgtc cctggcaag    2760
```

<210> SEQ ID NO 14
<211> LENGTH: 2166
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 14

```
atgtatagga tgcagctcct cagctgcatc gctctgtccc tcgccctggt gaccaacagc      60
ctccctgccc aggtggcctt tacaccctac gctcctgagc ccggaagcac ctgcaggctc     120
agggagtact acgatcagac cgcccaaatg tgttgcagca agtgctcccc tggccagcac     180
gccaaggtgt tctgcaccaa gacaagcgat accgtgtgcg atagctgtga ggacagcacc     240
tacacccagc tgtggaattg ggtgcccgag tgcctgagct gtggcagcag gtgcagcagc     300
gatcaggtgg agacacaggc ctgcaccaga gagcagaaca ggatttgtac ctgcaggccc     360
ggctggtatt gcgccctgag caagcaggag ggatgtaggc tgtgcgcccc tctgaggaaa     420
tgcagacctg gctttggagt ggctaggccc ggcaccgaga catccgacgt ggtgtgcaag     480
ccttgtgccc ctggcacctt tccaacacc accagctcca ccgacatctg caggccccat     540
cagatttgca acgtggtggc catccccgga aacgctagca tggatgccgt gtgcacctcc     600
acctccccta ccaggagcat ggcccctgga gccgtgcatc tgcctcaacc cgtcagcacc     660
agaagccagc acacacagcc caccccgaa cctagcaccg ctccctccac cagcttcctg     720
ctgcctatgg gacccgcccc tcctgccgaa gggagcaccg agatggagg aggaggaagc     780 ggcggaggag gctccagaac agtggctgcc cctagcgtgt tcattttccc tcccctccgac     840 gagcagctca gtccggaac cgcttccgtg tctgcctgc tgaacaactt ctacccagga     900
gaggccaagg tgcagtggaa agtcgacaat gctctgcaga cggaaactc caggagtcc     960 gtcaccgagc aggacagcaa ggactccaca tatagcctgt cctccaccct gaccctgagc    1020
aaggccgact atgagaaaca caaggtgtat gcctgcgaag tgacccacca gggcctgtcc    1080
agccccgtca ccaagtcctt caatagggc gagagcggag gcggcgggag cggcggcggc    1140
gggagcggag gaggagggag cggaggaggc ggaagcgctt ccaccaaggg acctagcgtg    1200 tttccctcg ccccagctc caagagcaca gcggaggca cagccgctct gggctgtctg    1260
gtgaaggatt acttccccga gccgtcaca gtgagctgga actccggagc cctgacctcc    1320
ggagtgcaca ccttctcctgc cgtgctgcag agcagcggac tgtacagcct gtccagcgtg    1380
gtcacagtgc cctccagctc cctgggcacc cagacctaca tctgcaacgt gaaccacaag    1440
cccagcaaca caaaggtgga caagagagtg gaacctaagt cctgtgacaa acccataccc    1500
tgccctccct gccctgcccc tgagctgctg ggaggaccta gcgtgtttct gtttcccccc    1560
aaacccaagg ataccctgat gatcagcagg acccctgagg tgacatgcgt ggtggtggac    1620
gtgtcccacg aggaccctca ggtcaagttc aactggtacg tggatggcgt ccaggtgcac    1680
aatgctaaga ccaagcccag ggagcagcaa tacaattcca cctacagggt ggtgtccgtg    1740
ctcaccgtcc tccaccagaa ctggctcgac ggcaaagaat acaagtgcaa agtgagcaac    1800
```

| | |
|---|---|
| aaggctctcc ccgcccctat cgagaagacc atttccaaag ccaagggcca gcccagagaa | 1860 |
| cctcaagtct acaccctgcc ccccagcagg gaggagatga ccaagaacca ggtgagcctg | 1920 |
| acctgcctcg tcaagggatt ctatcccagc gacatcgccg tggaatggga gtccaatggc | 1980 |
| cagcccgaga taactacaa gaccacaccc cccgtgctgg attccgatgg cagcttttc | 2040 |
| ctgtacagca agctgacagt ggataagagc aggtggcagc agggcaacgt gttcagctgc | 2100 |
| tccgtcatgc acgaagccct gcacaatcac tacacccaga gagcctgtc cctcagcccc | 2160 |
| ggcaag | 2166 |

<210> SEQ ID NO 15
<211> LENGTH: 1917
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

| | |
|---|---|
| atgtaccgga tgcagctgct gtcctgtatc gccctgtctc tggccctggt caccaactcc | 60 |
| agaccctctg gccggaagtc ctccaagatg caggccttcc ggatctggga cgtgaaccag | 120 |
| aaaaccttct acctgcggaa caaccagctg gtggccggct atctgcaggg ccccaacgtg | 180 |
| aacctggaag agaagatcga cgtggtgccc atcgagcccc acgccctgtt tctgggaatc | 240 |
| cacggcggca agatgtgcct gtcctgcgtg aagtccggcg acgagacacg gctgcagctg | 300 |
| gaagccgtga acatcaccga cctgtccgag aacggaagc aggacaagag attcgccttc | 360 |
| atcagatccg actccggccc taccacctcc ttcgagtctg ctgcttgccc cggctggttc | 420 |
| ctgtgcaccg ccatggaagc tgaccagccc gtgtccctga ccaacatgcc tgacgagggc | 480 |
| gtgatggtca ccaagttcta ttttcaggaa gatgagggcg aggcggctc tggcggcgga | 540 |
| ggatctagaa cagtggccgc tccctccgtg ttcatcttcc caccttccga cgagcagctg | 600 |
| aagtctggca ccgcctctgt cgtgtgcctg ctgaacaact tctaccctcg cgaggccaag | 660 |
| gtgcagtgga aggtggacaa cgccctgcag tccggcaact cccaggaatc cgtcaccgag | 720 |
| caggactcca aggacagcac ctactccctg tcctccaccc tgaccctgtc caaggccgac | 780 |
| tacgagaagc acaaggtgta cgcctgcgaa gtgacccacc agggcctgtc tagccccgtg | 840 |
| accaagtctt tcaaccgggg cgaaagcgga ggcgaggtt caggtggtgg tggatcaggt | 900 |
| ggcggcggat ctggcggtgg tggctctgct tctaccaagg cccttccgt gttccctctg | 960 |
| gccccttcca gcaagtctac ctctggcggc acagccgctc tgggctgcct ggtcaaggac | 1020 |
| tacttccccg agcctgtgac cgtgtcctgg aactctggcg ctctgacatc cggcgtgcac | 1080 |
| accttccctg ctgtgctgca gtcctccggc ctgtacagcc tgtcctccgt cgtgaccgtg | 1140 |
| ccttccagct ctctgggcac ccagacctac atctgtaacg tgaaccacaa gcctccaac | 1200 |
| accaaagtgg acaagcgggt ggaacccaag tcctccgaca gacccacac tgtcctccc | 1260 |
| tgccctgctc ctgaactgct gggcggacct agcgtgttcc tgttccctcc aaagcccaag | 1320 |
| gacaccctga tgatctcccg gacccctgaa gtgacctgcg tggtggtcga tgtgtcccac | 1380 |
| gaggacccaa agtgaagtt caattggtac gtggacggcg tggaagtgca caatgccaag | 1440 |
| accaagccca gagaggaaca gtacaactcc acctaccggg tggtgtccgt gctgaccgtg | 1500 |
| ctgcaccagg attggctgaa cggcaaagag tacaagtgca aggtgtccaa caaggccctg | 1560 |
| cctgccccta tcgaaaagac catctccaag gccaagggcc agccccggga acctcaggtg | 1620 |

```
tacaccctgc ctcccagccg ggaagagatg accaagaacc aggtgtcact gacctgtctg    1680
gtcaagggct ctaccccctc cgacattgcc gtggaatggg agtccaacgg ccagcccgag    1740
aacaactaca agaccacccc tcccgtgctg gactccgacg gctcattctt cctgtactcc    1800
aagctgaccg tggacaagtc ccggtggcag cagggcaacg tgttctcctg ctccgtgatg    1860
cacgaggccc tgcacaacca ctacacccag aagtccctgt ccctgagccc cggcaag      1917
```

```
<210> SEQ ID NO 16
<211> LENGTH: 6
<212> TYPE: DNA
<213> ORGANISM: Unknown
<220> FEATURE:
<223> OTHER INFORMATION: Description of Unknown:
      Eukaryotic sequence
<220> FEATURE:
<221> NAME/KEY: modified_base
<222> LOCATION: (2)..(2)
<223> OTHER INFORMATION: a, c, t, g, unknown or other

<400> SEQUENCE: 16 cncaat                                                                6

<210> SEQ ID NO 17
<211> LENGTH: 6
<212> TYPE: DNA
<213> ORGANISM: Unknown
<220> FEATURE:
<223> OTHER INFORMATION: Description of Unknown:
      Eukaryotic sequence

<400> SEQUENCE: 17 aataaa                                                                6

<210> SEQ ID NO 18
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu

-continued

```
            145                 150                 155                 160
        Thr Gly Tyr Leu Arg Asn Gly Gly Gly Ser Gly Gly Gly Ser
                        165                 170                 175

Arg Thr Val Ala Ala Pro Ser Val Phe Ile Phe Pro Pro Ser Asp Glu
                        180                 185                 190

Gln Leu Lys Ser Gly Thr Ala Ser Val Val Cys Leu Leu Asn Asn Phe
                        195                 200                 205

Tyr Pro Arg Glu Ala Lys Val Gln Trp Lys Val Asp Asn Ala Leu Gln
                        210                 215                 220

Ser Gly Asn Ser Gln Glu Ser Val Thr Glu Gln Asp Ser Lys Asp Ser
        225                 230                 235                 240

Thr Tyr Ser Leu Ser Ser Thr Leu Thr Leu Ser Lys Ala Asp Tyr Glu
                        245                 250                 255

Lys His Lys Val Tyr Ala Cys Glu Val Thr His Gln Gly Leu Ser Ser
                        260                 265                 270

Pro Val Thr Lys Ser Phe Asn Arg Gly Glu Cys Gly Gly Gly Gly Ser
                        275                 280                 285

Gly Gly Gly Gly Ser Gly Gly Gly Ser Gly Gly Gly Gly Ser Ala
                        290                 295                 300

Ser Thr Lys Gly Pro Ser Val Phe Pro Leu Ala Pro Ser Ser Lys Ser
        305                 310                 315                 320

Thr Ser Gly Gly Thr Ala Ala Leu Gly Cys Leu Val Lys Asp Tyr Phe
                        325                 330                 335

Pro Glu Pro Val Thr Val Ser Trp Asn Ser Gly Ala Leu Thr Ser Gly
                        340                 345                 350

Val His Thr Phe Pro Ala Val Leu Gln Ser Ser Gly Leu Tyr Ser Leu
                        355                 360                 365

Ser Ser Val Val Thr Val Pro Ser Ser Ser Leu Gly Thr Gln Thr Tyr
                        370                 375                 380

Ile Cys Asn Val Asn His Lys Pro Ser Asn Thr Lys Val Asp Lys Arg
        385                 390                 395                 400

Val Glu Pro Lys Ser Cys Asp Lys Thr His Thr Cys Pro Pro Cys Pro
                        405                 410                 415

Ala Pro Glu Leu Leu Gly Gly Pro Ser Val Phe Leu Phe Pro Pro Lys
                        420                 425                 430

Pro Lys Asp Thr Leu Met Ile Ser Arg Thr Pro Glu Val Thr Cys Val
                        435                 440                 445

Val Val Asp Val Ser His Glu Asp Pro Glu Val Lys Phe Asn Trp Tyr
        450                 455                 460

Val Asp Gly Val Glu Val His Asn Ala Lys Thr Lys Pro Arg Glu Glu
        465                 470                 475                 480

Gln Tyr Asn Ser Thr Tyr Arg Val Val Ser Val Leu Thr Val Leu His
                        485                 490                 495

Gln Asp Trp Leu Asn Gly Lys Glu Tyr Lys Cys Lys Val Ser Asn Lys
                        500                 505                 510

Ala Leu Pro Ala Pro Ile Glu Lys Thr Ile Ser Lys Ala Lys Gly Gln
                        515                 520                 525

Pro Arg Glu Pro Gln Val Tyr Thr Leu Pro Pro Ser Arg Glu Glu Met
                        530                 535                 540

Thr Lys Asn Gln Val Ser Leu Thr Cys Leu Val Lys Gly Phe Tyr Pro
        545                 550                 555                 560

Ser Asp Ile Ala Val Glu Trp Glu Ser Asn Gly Gln Pro Glu Asn Asn
                        565                 570                 575
```

Tyr Lys Thr Thr Pro Pro Val Leu Asp Ser Asp Gly Ser Phe Phe Leu
            580                 585                 590

Tyr Ser Lys Leu Thr Val Asp Lys Ser Arg Trp Gln Gln Gly Asn Val
    595                 600                 605

Phe Ser Cys Ser Val Met His Glu Ala Leu His Asn His Tyr Thr Gln
    610                 615                 620

Lys Ser Leu Ser Leu Ser Pro Gly Lys
625                 630

<210> SEQ ID NO 19
<211> LENGTH: 767
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Lys Asn Phe His Leu Arg Pro Arg Asp Leu Ile Ser Asn Ile Asn
1               5                   10                  15

Val Ile Val Glu Leu Lys Gly Ser Glu Thr Thr Phe Met Cys Glu Tyr
            20                  25                  30

Ala Asp Glu Thr Ala Thr Ile Val Glu Phe Leu Asn Arg Trp Ile Thr
        35                  40                  45

Phe Ser Gln Ser Ile Ile Ser Thr Leu Thr Gly Gly Ser Ser Ser Thr
    50                  55                  60

Lys Lys Thr Gln Leu Gln Leu Glu His Leu Leu Leu Asp Leu Gln Met
65                  70                  75                  80

Ile Leu Asn Gly Ile Asn Asn Tyr Lys Asn Pro Lys Leu Thr Arg Met
                85                  90                  95

Leu Thr Phe Lys Phe Tyr Met Pro Lys Lys Ala Thr Glu Leu Lys His
            100                 105                 110

Leu Gln Cys Leu Glu Glu Glu Leu Lys Pro Leu Glu Glu Val Leu Asn
        115                 120                 125

Leu Ala Gln Gly Ser Gly Gly Gly Ser Glu Leu Cys Asp Asp Asp Pro
    130                 135                 140

Pro Glu Ile Pro His Ala Thr Phe Lys Ala Met Ala Tyr Lys Glu Gly
145                 150                 155                 160

Thr Met Leu Asn Cys Glu Cys Lys Arg Gly Phe Arg Arg Ile Lys Ser
                165                 170                 175

Gly Ser Leu Tyr Met Leu Cys Thr Gly Asn Ser Ser His Ser Ser Trp
            180                 185                 190

Asp Asn Gln Cys Gln Cys Thr Ser Ser Ala Thr Arg Asn Thr Thr Lys
        195                 200                 205

Gln Val Thr Pro Gln Pro Glu Glu Gln Lys Glu Arg Lys Thr Thr Glu
    210                 215                 220

Met Gln Ser Pro Met Gln Pro Val Asp Gln Ala Ser Leu Pro Gly His
225                 230                 235                 240

Cys Arg Glu Pro Pro Pro Trp Glu Asn Glu Ala Thr Glu Arg Ile Tyr
                245                 250                 255

His Phe Val Val Gly Gln Met Val Tyr Tyr Gln Cys Val Gln Gly Tyr
            260                 265                 270

Arg Ala Leu His Arg Gly Pro Ala Glu Ser Val Cys Lys Met Thr His
        275                 280                 285

Gly Lys Thr Arg Trp Thr Gln Pro Gln Leu Ile Cys Thr Gly Gly Gly

```
             290                 295                 300
Gly Gly Ser Gly Gly Ser Arg Thr Val Ala Ala Pro Ser Val Phe
305                 310                 315                 320

Ile Phe Pro Pro Ser Asp Glu Gln Leu Lys Ser Gly Thr Ala Ser Val
                325                 330                 335

Val Cys Leu Leu Asn Asn Phe Tyr Pro Arg Glu Ala Lys Val Gln Trp
                340                 345                 350

Lys Val Asp Asn Ala Leu Ser Gly Asn Ser Gln Glu Ser Val Thr Glu
                355                 360                 365

Gln Asp Ser Lys Asp Ser Thr Tyr Ser Leu Ser Ser Thr Leu Thr Leu
            370                 375                 380

Ser Lys Ala Asp Tyr Glu Lys His Lys Val Tyr Ala Cys Glu Val Thr
385                 390                 395                 400

His Gln Gly Leu Ser Ser Pro Val Thr Lys Ser Phe Asn Arg Gly Glu
                405                 410                 415

Cys Gly Gly Gly Gly Ser Gly Gly Gly Ser Gly Gly Gly Gly Ser
                420                 425                 430

Gly Gly Gly Gly Ser Ala Ser Thr Lys Gly Pro Ser Val Phe Pro Leu
            435                 440                 445

Ala Pro Ser Ser Lys Ser Thr Ser Gly Gly Thr Ala Ala Leu Gly Cys
    450                 455                 460

Leu Val Lys Asp Tyr Phe Pro Glu Pro Val Thr Val Ser Trp Asn Ser
465                 470                 475                 480

Gly Ala Leu Thr Ser Gly Val His Thr Phe Pro Ala Val Leu Gln Ser
                485                 490                 495

Ser Gly Leu Tyr Ser Leu Ser Ser Val Val Thr Val Pro Ser Ser Ser
                500                 505                 510

Leu Gly Thr Gln Thr Tyr Ile Cys Asn Val Asn His Lys Pro Ser Asn
            515                 520                 525

Thr Lys Val Asp Lys Arg Val Glu Pro Lys Ser Cys Asp Lys Thr His
        530                 535                 540

Thr Cys Pro Pro Cys Pro Ala Pro Glu Leu Leu Gly Gly Pro Ser Val
545                 550                 555                 560

Phe Leu Phe Pro Pro Lys Pro Lys Asp Thr Leu Met Ile Ser Arg Thr
                565                 570                 575

Pro Glu Val Thr Cys Val Val Val Asp Val Ser His Glu Asp Pro Glu
                580                 585                 590

Val Lys Phe Asn Trp Tyr Val Asp Gly Val Glu Val His Asn Ala Lys
            595                 600                 605

Thr Lys Pro Arg Glu Glu Gln Tyr Asn Ser Thr Tyr Arg Val Val Ser
        610                 615                 620

Val Leu Thr Val Leu His Gln Asp Trp Leu Asn Gly Lys Glu Tyr Lys
625                 630                 635                 640

Cys Lys Val Ser Asn Lys Ala Leu Pro Ala Pro Ile Glu Lys Thr Ile
                645                 650                 655

Ser Lys Ala Lys Gly Gln Pro Arg Glu Pro Gln Val Tyr Thr Leu Pro
            660                 665                 670

Pro Ser Arg Glu Glu Met Thr Lys Asn Gln Val Ser Leu Thr Cys Leu
        675                 680                 685

Val Lys Gly Phe Tyr Pro Ser Asp Ile Ala Val Glu Trp Glu Ser Asn
    690                 695                 700

Gly Gln Pro Glu Asn Asn Tyr Lys Thr Thr Pro Pro Val Leu Asp Ser
705                 710                 715                 720
```

-continued

```
Asp Gly Ser Phe Phe Leu Tyr Ser Lys Leu Thr Val Asp Lys Ser Arg
                725                 730                 735

Trp Gln Gln Gly Asn Val Phe Ser Cys Ser Val Met His Glu Ala Leu
            740                 745                 750

His Asn His Tyr Thr Gln Lys Ser Leu Ser Leu Ser Pro Gly Lys
        755                 760                 765

<210> SEQ ID NO 20
<211> LENGTH: 770
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Lys Asn Phe His Leu Arg Pro Arg Asp Leu Ile Ser Asn Ile Asn
1               5                   10                  15

Val Ile Val Leu Glu Leu Lys Gly Ser Glu Thr Thr Phe Met Cys Glu
            20                  25                  30

Tyr Ala Asp Glu Thr Ala Thr Ile Val Glu Phe Leu Asn Arg Trp Ile
        35                  40                  45

Thr Phe Ser Gln Ser Ile Ile Ser Thr Leu Thr Gly Gly Ser Ser Ser
    50                  55                  60

Thr Lys Lys Thr Gln Leu Gln Leu Glu His Leu Leu Leu Asp Leu Gln
65                  70                  75                  80

Met Ile Leu Asn Gly Ile Asn Asn Tyr Lys Asn Pro Lys Leu Thr Arg
                85                  90                  95

Met Leu Thr Phe Lys Phe Tyr Met Pro Lys Lys Ala Thr Glu Leu Lys
            100                 105                 110

His Leu Gln Cys Leu Glu Glu Glu Leu Lys Pro Leu Glu Glu Val Leu
        115                 120                 125

Asn Leu Ala Gln Gly Ser Gly Gly Gly Ser Glu Leu Cys Asp Asp Asp
    130                 135                 140

Pro Pro Glu Ile Pro His Ala Thr Phe Lys Ala Met Ala Tyr Lys Glu
145                 150                 155                 160

Gly Thr Met Leu Asn Cys Glu Cys Lys Arg Gly Phe Arg Arg Ile Lys
                165                 170                 175

Ser Gly Ser Leu Tyr Met Leu Cys Thr Gly Asn Ser Ser His Ser Ser
            180                 185                 190

Trp Asp Asn Gln Cys Gln Cys Thr Ser Ser Ala Thr Arg Asn Thr Thr
        195                 200                 205

Lys Gln Val Thr Pro Gln Pro Glu Glu Gln Lys Glu Arg Lys Thr Thr
    210                 215                 220

Glu Met Gln Ser Pro Met Gln Pro Val Asp Gln Ala Ser Leu Pro Gly
225                 230                 235                 240

His Cys Arg Glu Pro Pro Pro Trp Glu Asn Glu Ala Thr Glu Arg Ile
                245                 250                 255

Tyr His Phe Val Val Gly Gln Met Val Tyr Tyr Gln Cys Val Gln Gly
            260                 265                 270

Tyr Arg Ala Leu His Arg Gly Pro Ala Glu Ser Val Cys Lys Met Thr
        275                 280                 285

His Gly Lys Thr Arg Trp Thr Gln Pro Gln Leu Ile Cys Thr Gly Gly
    290                 295                 300

Gly Gly Gly Ser Gly Gly Gly Gly Ser Ala Ser Thr Lys Gly Pro Ser
```

```
            305                 310                 315                 320
Val Phe Pro Leu Ala Pro Ser Ser Lys Ser Thr Ser Gly Gly Thr Ala
                    325                 330                 335

Ala Leu Gly Cys Leu Val Lys Asp Tyr Phe Pro Glu Pro Val Thr Val
                    340                 345                 350

Ser Trp Asn Ser Gly Ala Leu Thr Ser Gly Val His Thr Phe Pro Ala
                    355                 360                 365

Val Leu Gln Ser Ser Gly Leu Tyr Ser Leu Ser Ser Val Val Thr Val
                    370                 375                 380

Pro Ser Ser Ser Leu Gly Thr Gln Thr Tyr Ile Cys Asn Val Asn His
385                 390                 395                 400

Lys Pro Ser Asn Thr Lys Val Asp Lys Arg Val Gly Gly Gly Gly Ser
                    405                 410                 415

Gly Gly Gly Gly Ser Gly Gly Gly Ser Arg Thr Val Ala Ala Pro
                    420                 425                 430

Ser Val Phe Ile Phe Pro Pro Ser Asp Glu Gln Leu Lys Ser Gly Thr
                    435                 440                 445

Ala Ser Val Val Cys Leu Leu Asn Asn Phe Tyr Pro Arg Glu Ala Lys
                    450                 455                 460

Val Gln Trp Lys Val Asp Asn Ala Leu Gln Ser Gly Asn Ser Gln Glu
465                 470                 475                 480

Ser Val Thr Glu Gln Asp Ser Lys Asp Ser Thr Tyr Ser Leu Ser Ser
                    485                 490                 495

Thr Leu Thr Leu Ser Lys Ala Asp Tyr Glu Lys His Lys Val Tyr Ala
                    500                 505                 510

Cys Glu Val Thr His Gln Gly Leu Ser Ser Pro Val Thr Lys Ser Phe
                    515                 520                 525

Asn Arg Gly Glu Cys Gly Gly Ser Gly Gly Pro Lys Ser Cys Asp
                    530                 535                 540

Lys Thr His Thr Cys Pro Pro Cys Pro Ala Pro Glu Leu Leu Gly Gly
545                 550                 555                 560

Pro Ser Val Phe Leu Phe Pro Pro Lys Pro Lys Asp Thr Leu Met Ile
                    565                 570                 575

Ser Arg Thr Pro Glu Val Thr Cys Val Val Val Asp Val Ser His Glu
                    580                 585                 590

Asp Pro Glu Val Lys Phe Asn Trp Tyr Val Asp Gly Val Glu Val His
                    595                 600                 605

Asn Ala Lys Thr Lys Pro Arg Glu Glu Gln Tyr Asn Ser Thr Tyr Arg
                    610                 615                 620

Val Val Ser Val Leu Thr Val Leu His Gln Asp Trp Leu Asn Gly Lys
625                 630                 635                 640

Glu Tyr Lys Cys Lys Val Ser Asn Lys Ala Leu Pro Ala Pro Ile Glu
                    645                 650                 655

Lys Thr Ile Ser Lys Ala Lys Gly Gln Pro Arg Glu Pro Gln Val Tyr
                    660                 665                 670

Thr Leu Pro Pro Ser Arg Glu Glu Met Thr Lys Asn Gln Val Ser Leu
                    675                 680                 685

Thr Cys Leu Val Lys Gly Phe Tyr Pro Ser Asp Ile Ala Val Glu Trp
                    690                 695                 700

Glu Ser Asn Gly Gln Pro Glu Asn Asn Tyr Lys Thr Thr Pro Pro Val
705                 710                 715                 720

Leu Asp Ser Asp Gly Ser Phe Phe Leu Tyr Ser Lys Leu Thr Val Asp
                    725                 730                 735
```

-continued

```
Lys Ser Arg Trp Gln Gln Gly Asn Val Phe Ser Cys Ser Val Met His
            740                 745                 750

Glu Ala Leu His Asn His Tyr Thr Gln Lys Ser Leu Ser Leu Ser Pro
        755                 760                 765

Gly Lys
    770

<210> SEQ ID NO 21
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 'Gly Gly Gly
      Ser' repeating units, wherein some positions may be absent

<400> SEQUENCE: 21

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 22
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 'Gly Gly Gly
      Gly Ser' repeating units, wherein some positions may be absent

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 23
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Tyr Arg Met Gln Leu Leu Ser Cys Ile Ala Leu Ser Leu Ala Leu
1               5                   10                  15

Val Thr Asn Ser Ser Pro Gly Gln Gly Thr Gln Ser Glu Asn Ser Cys
            20                  25                  30
```

```
Thr His Phe Pro Gly Asn Leu Pro Asn Met Leu Arg Asp Leu Arg Asp
            35                  40                  45

Ala Phe Ser Arg Val Lys Thr Phe Phe Gln Met Lys Asp Gln Leu Asp
        50                  55                  60

Asn Leu Leu Leu Lys Glu Ser Leu Leu Glu Asp Phe Lys Gly Tyr Leu
65                  70                  75                  80

Gly Cys Gln Ala Leu Ser Glu Met Ile Gln Phe Tyr Leu Glu Glu Val
                85                  90                  95

Met Pro Gln Ala Glu Asn Gln Asp Pro Asp Ile Lys Ala His Val Asn
                100                 105                 110

Ser Leu Gly Glu Asn Leu Lys Thr Leu Arg Leu Arg Leu Arg Arg Cys
            115                 120                 125

His Arg Phe Leu Pro Cys Glu Asn Lys Ser Lys Ala Val Glu Gln Val
        130                 135                 140

Lys Asn Ala Phe Asn Lys Leu Gln Glu Lys Gly Ile Tyr Lys Ala Met
145                 150                 155                 160

Ser Glu Phe Asp Ile Phe Ile Asn Tyr Ile Glu Ala Tyr Met Thr Met
                165                 170                 175

Lys Ile Arg Asn Gly Gly Ser Gly Gly Gly Ser Gly Gly Ser Pro
            180                 185                 190

Gly Gln Gly Thr Gln Ser Glu Asn Ser Cys Thr His Phe Pro Gly Asn
            195                 200                 205

Leu Pro Asn Met Leu Arg Asp Leu Arg Asp Ala Phe Ser Arg Val Lys
        210                 215                 220

Thr Phe Phe Gln Met Lys Asp Gln Leu Asp Asn Leu Leu Leu Lys Glu
225                 230                 235                 240

Ser Leu Leu Glu Asp Phe Lys Gly Tyr Leu Gly Cys Gln Ala Leu Ser
                245                 250                 255

Glu Met Ile Gln Phe Tyr Leu Glu Glu Val Met Pro Gln Ala Glu Asn
                260                 265                 270

Gln Asp Pro Asp Ile Lys Ala His Val Asn Ser Leu Gly Glu Asn Leu
            275                 280                 285

Lys Thr Leu Arg Leu Arg Leu Arg Arg Cys His Arg Phe Leu Pro Cys
        290                 295                 300

Glu Asn Lys Ser Lys Ala Val Glu Gln Val Lys Asn Ala Phe Asn Lys
305                 310                 315                 320

Leu Gln Glu Lys Gly Ile Tyr Lys Ala Met Ser Glu Phe Asp Ile Phe
                325                 330                 335

Ile Asn Tyr Ile Glu Ala Tyr Met Thr Met Lys Ile Arg Asn Gly Gly
            340                 345                 350

Gly Gly Ser Gly Gly Gly Ser Arg Thr Val Ala Ala Pro Ser Val
            355                 360                 365

Phe Ile Phe Pro Pro Ser Asp Glu Gln Leu Lys Ser Gly Thr Ala Ser
        370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
        435                 440                 445
```

```
Val Thr His Gln Gly Leu Ser Ser Pro Val Thr Lys Ser Phe Asn Arg
    450                 455                 460

Gly Glu Cys Gly Gly Gly Ser Gly Gly Gly Ser Gly Gly Gly
465                 470                 475                 480

Gly Ser Gly Gly Gly Ser Ala Ser Thr Lys Gly Pro Ser Val Phe
                485                 490                 495

Pro Leu Ala Pro Ser Ser Lys Ser Thr Ser Gly Gly Thr Ala Ala Leu
                500                 505                 510

Gly Cys Leu Val Lys Asp Tyr Phe Pro Glu Pro Val Thr Val Ser Trp
            515                 520                 525

Asn Ser Gly Ala Leu Thr Ser Gly Val His Thr Phe Pro Ala Val Leu
530                 535                 540

Gln Ser Ser Gly Leu Tyr Ser Leu Ser Ser Val Val Thr Val Pro Ser
545                 550                 555                 560

Ser Ser Leu Gly Thr Gln Thr Tyr Ile Cys Asn Val Asn His Lys Pro
                565                 570                 575

Ser Asn Thr Lys Val Asp Lys Arg Val Glu Pro Lys Ser Cys Asp Lys
            580                 585                 590

Thr His Thr Cys Pro Pro Cys Pro Ala Pro Glu Leu Leu Gly Gly Pro
        595                 600                 605

Ser Val Phe Leu Phe Pro Pro Lys Pro Lys Asp Thr Leu Met Ile Ser
    610                 615                 620

Arg Thr Pro Glu Val Thr Cys Val Val Val Asp Val Ser His Glu Asp
625                 630                 635                 640

Pro Glu Val Lys Phe Asn Trp Tyr Val Asp Gly Val Glu Val His Asn
                645                 650                 655

Ala Lys Thr Lys Pro Arg Glu Glu Gln Tyr Asn Ser Thr Tyr Arg Val
            660                 665                 670

Val Ser Val Leu Thr Val Leu His Gln Asp Trp Leu Asn Gly Lys Glu
        675                 680                 685

Tyr Lys Cys Lys Val Ser Asn Lys Ala Leu Pro Ala Pro Ile Glu Lys
    690                 695                 700

Thr Ile Ser Lys Ala Lys Gly Gln Pro Arg Glu Pro Gln Val Tyr Thr
705                 710                 715                 720

Leu Pro Pro Ser Arg Glu Glu Met Thr Lys Asn Gln Val Ser Leu Thr
                725                 730                 735

Cys Leu Val Lys Gly Phe Tyr Pro Ser Asp Ile Ala Val Glu Trp Glu
            740                 745                 750

Ser Asn Gly Gln Pro Glu Asn Asn Tyr Lys Thr Thr Pro Pro Val Leu
        755                 760                 765

Asp Ser Asp Gly Ser Phe Phe Leu Tyr Ser Lys Leu Thr Val Asp Lys
    770                 775                 780

Ser Arg Trp Gln Gln Gly Asn Val Phe Ser Cys Ser Val Met His Glu
785                 790                 795                 800

Ala Leu His Asn His Tyr Thr Gln Lys Ser Leu Ser Leu Ser Pro Gly
                805                 810                 815

Lys

<210> SEQ ID NO 24
<211> LENGTH: 822
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 24

```
Met Tyr Arg Met Gln Leu Leu Ser Cys Ile Ala Leu Ser Leu Ala Leu
1               5                   10                  15
Val Thr Asn Ser Ser Pro Gly Gln Gly Thr Gln Ser Glu Asn Ser Cys
            20                  25                  30
Thr His Phe Pro Gly Asn Leu Pro Asn Met Leu Arg Asp Leu Arg Asp
        35                  40                  45
Ala Phe Ser Arg Val Lys Thr Phe Phe Gln Met Lys Asp Gln Leu Asp
    50                  55                  60
Asn Leu Leu Leu Lys Glu Ser Leu Leu Glu Asp Phe Lys Gly Tyr Leu
65                  70                  75                  80
Gly Cys Gln Ala Leu Ser Glu Met Ile Gln Phe Tyr Leu Glu Glu Val
                85                  90                  95
Met Pro Gln Ala Glu Asn Gln Asp Pro Asp Ile Lys Ala His Val Asn
            100                 105                 110
Ser Leu Gly Glu Asn Leu Lys Thr Leu Arg Leu Arg Leu Arg Arg Cys
        115                 120                 125
His Arg Phe Leu Pro Cys Glu Asn Lys Ser Lys Ala Val Glu Gln Val
    130                 135                 140
Lys Asn Ala Phe Asn Lys Leu Gln Glu Lys Gly Ile Tyr Lys Ala Met
145                 150                 155                 160
Ser Glu Phe Asp Ile Phe Ile Asn Tyr Ile Glu Ala Tyr Met Thr Met
                165                 170                 175
Lys Ile Arg Asn Gly Gly Ser Gly Gly Gly Ser Gly Gly Ser Pro
            180                 185                 190
Gly Gln Gly Thr Gln Ser Glu Asn Ser Cys Thr His Phe Pro Gly Asn
        195                 200                 205
Leu Pro Asn Met Leu Arg Asp Leu Arg Asp Ala Phe Ser Arg Val Lys
    210                 215                 220
Thr Phe Phe Gln Met Lys Asp Gln Leu Asp Asn Leu Leu Leu Lys Glu
225                 230                 235                 240
Ser Leu Leu Glu Asp Phe Lys Gly Tyr Leu Gly Cys Gln Ala Leu Ser
                245                 250                 255
Glu Met Ile Gln Phe Tyr Leu Glu Glu Val Met Pro Gln Ala Glu Asn
            260                 265                 270
Gln Asp Pro Asp Ile Lys Ala His Val Asn Ser Leu Gly Glu Asn Leu
        275                 280                 285
Lys Thr Leu Arg Leu Arg Leu Arg Arg Cys His Arg Phe Leu Pro Cys
    290                 295                 300
Glu Asn Lys Ser Lys Ala Val Glu Gln Val Lys Asn Ala Phe Asn Lys
305                 310                 315                 320
Leu Gln Glu Lys Gly Ile Tyr Lys Ala Met Ser Glu Phe Asp Ile Phe
                325                 330                 335
Ile Asn Tyr Ile Glu Ala Tyr Met Thr Met Lys Ile Arg Asn Gly Gly
            340                 345                 350
Gly Gly Ser Gly Gly Gly Ser Ala Ser Thr Lys Gly Pro Ser Val
        355                 360                 365
Phe Pro Leu Ala Pro Ser Ser Lys Ser Thr Ser Gly Gly Thr Ala Ala
    370                 375                 380
Leu Gly Cys Leu Val Lys Asp Tyr Phe Pro Glu Pro Val Thr Val Ser
385                 390                 395                 400
Trp Asn Ser Gly Ala Leu Thr Ser Gly Val His Thr Phe Pro Ala Val
```

```
                    405                 410                 415
Leu Gln Ser Ser Gly Leu Tyr Ser Leu Ser Val Val Thr Val Pro
            420                 425                 430
Ser Ser Ser Leu Gly Thr Gln Thr Tyr Ile Cys Asn Val Asn His Lys
            435                 440                 445
Pro Ser Asn Thr Lys Val Asp Lys Arg Val Gly Gly Gly Ser Gly
            450                 455                 460
Gly Gly Gly Ser Gly Gly Gly Ser Gly Gly Gly Ser Arg Thr
465                 470                 475                 480
Val Ala Ala Pro Ser Val Phe Ile Phe Pro Pro Ser Asp Glu Gln Leu
                485                 490                 495
Lys Ser Gly Thr Ala Ser Val Val Cys Leu Leu Asn Asn Phe Tyr Pro
                500                 505                 510
Arg Glu Ala Lys Val Gln Trp Lys Val Asp Asn Ala Leu Gln Ser Gly
                515                 520                 525
Asn Ser Gln Glu Ser Val Thr Glu Gln Asp Ser Lys Asp Ser Thr Tyr
            530                 535                 540
Ser Leu Ser Ser Thr Leu Thr Leu Ser Lys Ala Asp Tyr Glu Lys His
545                 550                 555                 560
Lys Val Tyr Ala Cys Glu Val Thr His Gln Gly Leu Ser Ser Pro Val
                565                 570                 575
Thr Lys Ser Phe Asn Arg Gly Glu Cys Gly Gly Ser Gly Gly Glu Pro
                580                 585                 590
Lys Ser Cys Asp Lys Thr His Thr Cys Pro Pro Cys Pro Ala Pro Glu
                595                 600                 605
Leu Leu Gly Gly Pro Ser Val Phe Leu Phe Pro Pro Lys Pro Lys Asp
        610                 615                 620
Thr Leu Met Ile Ser Arg Thr Pro Glu Val Thr Cys Val Val Val Asp
625                 630                 635                 640
Val Ser His Glu Asp Pro Glu Val Lys Phe Asn Trp Tyr Val Asp Gly
                645                 650                 655
Val Glu Val His Asn Ala Lys Thr Lys Pro Arg Glu Glu Gln Tyr Asn
            660                 665                 670
Ser Thr Tyr Arg Val Val Ser Val Leu Thr Val Leu His Gln Asp Trp
        675                 680                 685
Leu Asn Gly Lys Glu Tyr Lys Cys Lys Val Ser Asn Lys Ala Leu Pro
        690                 695                 700
Ala Pro Ile Glu Lys Thr Ile Ser Lys Ala Lys Gly Gln Pro Arg Glu
705                 710                 715                 720
Pro Gln Val Tyr Thr Leu Pro Pro Ser Arg Glu Glu Met Thr Lys Asn
                725                 730                 735
Gln Val Ser Leu Thr Cys Leu Val Lys Gly Phe Tyr Pro Ser Asp Ile
            740                 745                 750
Ala Val Glu Trp Glu Ser Asn Gly Gln Pro Glu Asn Asn Tyr Lys Thr
            755                 760                 765
Thr Pro Pro Val Leu Asp Ser Asp Gly Ser Phe Phe Leu Tyr Ser Lys
        770                 775                 780
Leu Thr Val Asp Lys Ser Arg Trp Gln Gln Gly Asn Val Phe Ser Cys
785                 790                 795                 800
Ser Val Met His Glu Ala Leu His Asn His Tyr Thr Gln Lys Ser Leu
                805                 810                 815
Ser Leu Ser Pro Gly Lys
            820
```

<210> SEQ ID NO 25
<211> LENGTH: 577
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Tyr Arg Met Gln Leu Leu Ser Cys Ile Ala Leu Ser Leu Ala Leu
1               5                   10                  15

Val Thr Asn Ser Ser Pro Gly Gln Gly Thr Gln Ser Glu Asn Ser Cys
            20                  25                  30

Thr His Phe Pro Gly Asn Leu Pro Asn Met Leu Arg Asp Leu Arg Asp
        35                  40                  45

Ala Phe Ser Arg Val Lys Thr Phe Phe Gln Met Lys Asp Gln Leu Asp
    50                  55                  60

Asn Leu Leu Leu Lys Glu Ser Leu Leu Glu Asp Phe Lys Gly Tyr Leu
65                  70                  75                  80

Gly Cys Gln Ala Leu Ser Glu Met Ile Gln Phe Tyr Leu Glu Glu Val
                85                  90                  95

Met Pro Gln Ala Glu Asn Gln Asp Pro Asp Ile Lys Ala His Val Asn
            100                 105                 110

Ser Leu Gly Glu Asn Leu Lys Thr Leu Arg Leu Arg Leu Arg Arg Cys
        115                 120                 125

His Arg Phe Leu Pro Cys Glu Asn Lys Ser Lys Ala Val Glu Gln Val
    130                 135                 140

Lys Asn Ala Phe Asn Lys Leu Gln Glu Lys Gly Ile Tyr Lys Ala Met
145                 150                 155                 160

Ser Glu Phe Asp Ile Phe Ile Asn Tyr Ile Glu Ala Tyr Met Thr Met
                165                 170                 175

Lys Ile Arg Asn Gly Gly Ser Gly Gly Ser Pro Gly Gln Gly Thr Gln
            180                 185                 190

Ser Glu Asn Ser Cys Thr His Phe Pro Gly Asn Leu Pro Asn Met Leu
        195                 200                 205

Arg Asp Leu Arg Asp Ala Phe Ser Arg Val Lys Thr Phe Phe Gln Met
    210                 215                 220

Lys Asp Gln Leu Asp Asn Leu Leu Leu Lys Glu Ser Leu Leu Glu Asp
225                 230                 235                 240

Phe Lys Gly Tyr Leu Gly Cys Gln Ala Leu Ser Glu Met Ile Gln Phe
                245                 250                 255

Tyr Leu Glu Glu Val Met Pro Gln Ala Glu Asn Gln Asp Pro Asp Ile
            260                 265                 270

Lys Ala His Val Asn Ser Leu Gly Glu Asn Leu Lys Thr Leu Arg Leu
        275                 280                 285

Arg Leu Arg Arg Cys His Arg Phe Leu Pro Cys Glu Asn Lys Ser Lys
    290                 295                 300

Ala Val Glu Gln Val Lys Asn Ala Phe Asn Lys Leu Gln Glu Lys Gly
305                 310                 315                 320

Ile Tyr Lys Ala Met Ser Glu Phe Asp Ile Phe Ile Asn Tyr Ile Glu
                325                 330                 335

Ala Tyr Met Thr Met Lys Ile Arg Asn Glu Pro Lys Ser Ser Asp Lys
            340                 345                 350

Thr His Thr Cys Pro Pro Cys Pro Ala Pro Glu Leu Leu Gly Gly Pro
```

```
                    355                 360                 365
Ser Val Phe Leu Phe Pro Pro Lys Pro Lys Asp Thr Leu Met Ile Ser
            370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 2 or 4 'Gly Gly Gly
      Gly Ser' repeating units, wherein some positions may be absent

<400> SEQUENCE: 26

Gly Gly Gly Gly Ser Gly Gly Gly Ser Gly Gly Gly Gly Ser Gly
1               5                   10                  15

Gly Gly Gly Ser
            20

<210> SEQ ID NO 27
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 'Gly Gly Gly
      Gly Ser' repeating units, wherein some positions may be absent
```

```
<400> SEQUENCE: 27

Gly Gly Gly Gly Ser Gly Gly Gly Ser Gly Gly Gly Gly Ser Gly
1               5                   10                  15
Gly Gly Gly Ser Gly Gly Gly Gly Ser
            20                  25
```

SINGLE CHAIN FC FUSION PROTEINS

RELATED APPLICATIONS

This application is a continuation of U.S. application Ser. No. 14/974,114, filed Dec. 18, 2015, which claims the benefit of U.S. Provisional Application No. 62/094,242, filed on Dec. 19, 2014. The entire teachings of the above applications are incorporated herein by reference.

SEQUENCE LISTING

The instant application contains a Sequence Listing which has been submitted electronically in ASCII format and is hereby incorporated by reference in its entirety. Said ASCII copy, created on Jan. 13, 2016, is named 4000.3065US1_SL.txt and is 80,419 bytes in size.

BACKGROUND OF THE INVENTION

One strategy for increasing serum half-life of a therapeutic protein is to attach the protein to an Fc (fragment crystallizable) domain of an antibody. Many such fusion proteins are capable of forming homodimers or heterodimers thereby forming antibody-like fusion protein molecules. However, many prior art approaches to Fc fusion protein engineering have limitations including, but not limited to, immunogenicity and poor pharmacokinetic properties.

The present invention provides monomers and dimers of Fc fusion proteins comprising novel linkers having single chain constant light (CL) and constant heavy (CH1) immunoglobulin domains. Such novel linkers are also referred to herein as scCLCH1 linkers.

Without limitation to a particular theory, the novel linkers of the invention reduce steric hindrance between the protein "payloads" on each of the single chain Fc fusion protein molecules when such molecules form dimers. Steric hindrance can result in losses in bioactivity, inefficient dimerization or reduction in the half-life of the dimer molecule for example, due to reduced binding to the FcRn. Thus incorporation of the novel linkers of the invention may result in improvement in bioactivity, increased dimer formation, in increased half-life, and the ability to incorporate larger protein payloads than those possible on prior Fc fusion proteins. Additionally, in some Fc proteins of the invention are able to form dimers that provide a more native antibody structure around the Fc domain that may improve binding of the dimer molecules to the FcRn receptor and therefore increase the circulating half-life of the novel Fc fusion proteins of the invention as compared to prior art fusion proteins.

SUMMARY OF THE INVENTION

The present invention provides novel, single chain Fc fusion proteins having improved properties. The invention provides single chain fusions of soluble proteins fused to the Fc region of an immunoglobulin via a novel linker comprising a constant region of an immunoglobulin light chain (CL) linked to a CH1 constant region of an immunoglobulin heavy chain (scCLCH1 or scCH1CL linkers). This novel linker confers favorable properties on the Fc fusion proteins of the invention such as improved bioactivity and increased half-life as compared to non-Fc fusion counterparts or as compared to prior art Fc fusion proteins. The novel Fc fusion proteins as described herein may be designed to include soluble proteins of interest capable of binding or interacting with any target of interest with high specificity and affinity.

Preferably, an Fc fusion protein of the invention is a dimer. The dimers may be formed via covalent (e.g. disulfide linkages) or non-covalent interactions between single chain fusion proteins of the invention resulting in a homodimeric or heterodimeric protein complex retaining the advantageous properties of an antibody molecule for use as a therapeutic molecule.

In another aspect, the invention provides nucleic acids encoding the Fc fusion proteins provided herein. Also provided are vectors, including expression vectors, comprise a nucleic acid encoding any of the Fc fusion proteins described herein. Also provided are host cells containing such expression vectors and methods for producing the Fc fusion proteins described herein in the host cells.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Definitions

Figure 1A:
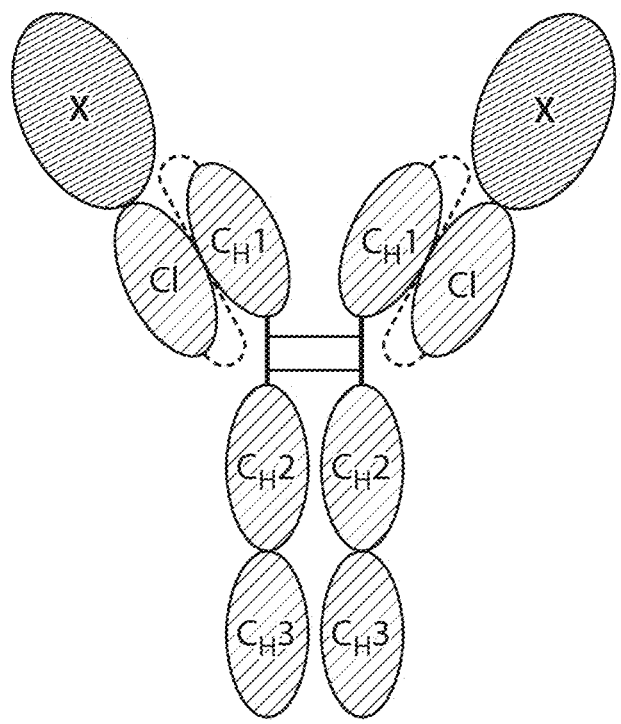
FIG. 1A is a diagram of an Fc fusion protein homodimer comprising X fused to the Fc region of an IgG1 antibody via the novel scCLCH1 linker in accordance with the invention.

By "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

As used herein, "antibody" and "immunoglobulin" are used interchangeably and refer to a polypeptide substantially encoded by an immunoglobulin gene or immunoglobulin genes, or fragments thereof, which specifically bind and recognize an antigen. Identified immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al, Eds., Antibodies: A Laboratory Manual, Chapter 14 (Cold Spring Harbor Laboratory, Cold Spring Harbor, 1988).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

The notations "mg/kg", or "mg per kg" refer to milligrams per kilogram. All notations are used interchangeably throughout the present disclosure.

The "half-life" of a polypeptide can generally be defined as the time taken for the serum concentration of the polypeptide to be reduced by 50%, in vivo, for example due to degradation of the polypeptide and/or clearance or sequestration of the polypeptide by natural mechanisms. The half-life can be determined in any manner known per se, such as by pharmacokinetic analysis. Suitable techniques will be clear to the person skilled in the art, and may, for example, generally involve the steps of administering a suitable dose of a polypeptide to a rodent or primate; collecting blood samples or other samples from a rodent or primate at regular intervals; determining the level or concentration of the polypeptide in said blood sample; and calculating, from (a plot of) the data thus obtained, the time until the level or concentration of the polypeptide has been reduced by 50% compared to the initial level upon dosing. Methods for determining half-life may be found, for example, in Kenneth et al., Chemical Stability of Pharmaceuticals: A Handbook for Pharmacists (1986); Peters et al, Pharmacokinete analysis: A Practical Approach (1996); and "Pharmacokinetics", M Gibaldi & D Perron, published by Marcel Dekker, 2nd Rev. edition (1982).

The half-life of a fusion polypeptide is increased if presence in a biological matrix (blood, serum, plasma, tissue) persists, in vivo, for a longer period as compared to an appropriate control. Half-life may be increased by 10%, 20%, 30%, 40%, 50% or more as compared to an appropriate control.

Half-life can be expressed using parameters such as the $t_{1/2-alpha}$, $t_{1/2-beta}$, and HL_Lambda_z. In the present specification, an "increase in half-life" refers to an increase in any one of these parameters, any two of these parameters, or all three of these parameters. An "increase in half-life" in particular refers to an increase in the $t_{1/2}$-beta and/or HL_Lambda_z, either with or without an increase in the $t_{1/2}$-alpha. Other PK parameters that can be assessed include volume of distribution (VD), clearance (CL), and mean residence time (MRT), and the area under the curve (AUC). In the present specification, a "change in pharmacokinetics" refers to changes in any one of these parameters, any two of these parameters, any three of these parameters, or all four of these parameters, in the presence or absence of changes in the half-life parameters listed above.

"Activity" for the purposes herein refers to an action or effect of a component of a fusion protein consistent with, but not necessarily identical to, that of the corresponding native active protein, wherein "biological activity" or "bioactivity" refers to an in vitro or in vivo biological function or effect, including but not limited to receptor binding, antagonist activity, agonist activity, or a cellular or physiologic response.

As used herein, a "dimer complex" comprises two single chain X-L1-HINGE-Fc fusion proteins of the invention, wherein the two single chain polypeptides are associated together under appropriate conditions via either non-covalent binding or covalent binding, for example, by a disulfide bridge. A "heterodimeric protein", "heterodimerized complex", or "heterodimer" as used interchangeably herein refers to a protein that is made of two single chain X-L1-HINGE-Fc polypeptides forming a dimer complex, wherein said two single chain polypeptides have different amino acid sequences, in particular, X represents different soluble proteins or different portions of the same soluble protein. A "homodimeric protein" "homodimerized complex" or "homodimer" as used interchangeably herein, refers to a protein that is made of two identical or substantially identical polypeptides forming the dimer complex, wherein said two single chain polypeptides share 100% identity, or at least 95% or at least 99% identity, the amino acid differences consisting of amino acid substitution, addition or deletion which does not affect the functional and physical properties of the polypeptide compared to the other one of the homodimer, for example conservative amino acid substitutions.

As used herein, a protein is "soluble" when it lacks any transmembrane domain or protein domain that anchors or integrates the polypeptide into the membrane of a cell expressing such polypeptide.

As used herein, "Fc domain", "Fc region" or "Fc portion" as those terms may be used interchangeably herein to describe an X-L1-HINGE-Fc fusion protein of the invention, encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder.

For prophylactic benefit, the compositions may be administered to a subject at risk of developing a particular disease, or to a subject reporting one or more of the physiological symptoms of a disease, even though a diagnosis of this disease may not have been made.

A "therapeutic effect", as used herein, refers to a physiologic effect, including but not limited to the cure, mitigation, amelioration, or prevention of disease in humans or other animals, or to otherwise enhance physical or mental well-being of humans or animals, caused by a fusion protein of the invention.

The terms "therapeutically effective amount" and "therapeutically effective dose", as used herein, refers to an amount of an active protein, either alone or as a part of a fusion protein composition, that is capable of having any detectable, beneficial effect on any symptom, aspect, measured parameter or characteristics of a disease state or condition when administered in one or repeated doses to a subject. Such effect need not be absolute to be beneficial.

The term "therapeutically effective dose regimen", as used herein, refers to a schedule for consecutively administered doses of an active protein, either alone or as a part of a fusion protein composition, wherein the doses are given in therapeutically effective amounts to result in sustained beneficial effect on any symptom, aspect, measured parameter or characteristics of a disease state or condition.

Single Chain Fc Fusion Proteins

Single chain Fc fusion proteins of the invention have the following arrangement from amino-terminus (N-terminus) to carboxy-terminus (C-terminus):

X-L1-HINGE-Fc wherein, X is a soluble protein;
L1 is a linker having the following arrangement from amino-terminus to carboxy-terminus:

L2-CL-L3-CH1-L4 or L2-CH1-L3-CL-L4 wherein,
L2 and L4 are independently polypeptide linkers or are independently absent,
L3 is a polypeptide linker;
CL is a constant region polypeptide from an immunoglobulin light chain; and
CH1 a constant region polypeptide from a CH1 domain of an immunoglobulin heavy chain;
HINGE is a hinge sequence of an immunoglobulin or is absent with the proviso that if HINGE is absent, L4 is present; and
Fc is the carboxy-terminus of an immunoglobulin or any active fragment or derivative thereof.

In accordance with the invention, a soluble protein of interest is fused to the N-terminal region of an immunoglobulin Fc region via a novel linker (L1) that is derived from the CL and CH1 domains of an immunoglobulin arranged as a single chain (sc) also referred to herein as "scCLCH1 linkers".

The C-terminus of the CL region may be linked to the N-terminal region of a CH1 region via polypeptide linker L3. The N-terminus of the CL region may be fused to the C-terminus of the protein of interest (X) via an optional polypeptide linker L2. The C-terminus of the CH1 domain is linked to the Fc domain via an immunoglobulin hinge region (HINGE) or a polypeptide linker (L4) or both a hinge (HINGE) and a polypeptide linker (L4).

The C-terminus of the CH1 domain may also be linked to the N-terminus of a CL region via polypeptide linker L3. The N-terminus of the CH1 region may be fused to the C-terminus of the protein of interest (X) via an optional polypeptide linker L2. The C-terminus of the CL region is linked to the Fc region via an immunoglobulin hinge region (HINGE) or a polypeptide linker (L4) or both a hinge (HINGE) and a polypeptide linker (L4).

Preferably, L3 is selected from artificial flexible domains comprising amino acids selected from Gly (G), and/or Ser (S). Preferably, the linker is comprised of polypeptide of the general formula (Gly-Gly-Gly-Ser (SEQ ID NO: 21))n or (Gly-Gly-Gly-Gly-Ser (SEQ ID NO: 22))n wherein n is an integer from 1 to 10. Preferably, each linker is a polypeptide comprising from about 1 to about 100 amino acids, preferably about 1-50 amino acids, preferably about 1-25 amino acids, preferably about 1-15 amino acids preferably about 1-10 amino acids, preferably about 4-24 amino acids, preferably about 5-20 amino acids preferably about 5-15 amino acids and preferably about 5-10 amino acids. Preferably, the linker is (Gly-Gly-Gly-Gly-Ser (SEQ ID NO: 26)) n wherein n is 2 or 4.

L2 and L4 are independently selected from artificial flexible domains comprising amino acids selected from, for example, Gly (G), and Ser (S). Preferably, the linker is comprised of polypeptide of the general formula (Gly-Gly-Gly-Ser (SEQ ID NO: 21))n or (Gly-Gly-Gly-Gly-Ser (SEQ ID NO: 22))n wherein n is an integer from 1 to 10. Preferably, each linker is a polypeptide comprising from about 1 to about 100 amino acids, preferably about 1-50 amino acids, preferably about 1-25 amino acids, preferably about 1-15 amino acids preferably about 1-10 amino acids, preferably about 4-24 amino acids, preferably about 5-20 amino acids preferably about 5-15 amino acids and preferably about 5-10 amino acids. Preferably, the linker is (Gly-Gly-Gly-Gly-Ser (SEQ ID NO: 26))n wherein n is 2 or 4.

L2, L3 and L4, may further comprise amino acids such as, for example, Lys (K), Thr (T), Glu (E), and Asp (D).

The CL region of the novel scCLCH1 linker (L1) may be substantially identical to the corresponding CL region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. The CL region (L1) may have amino acid sequence that is at least 50%, 60%, 75%, 80%, 85%, 90%, 95%, 96%, 97%, 98%, or 99% identical to the corresponding CL region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. If the CL region of L1 is a modified derivative or variant of a native CL region such modifications include, but are not limited to, amino acid insertions, deletions, substitutions and rearrangements. Preferably, the amino acid sequence of the CL region in accordance with the invention, is at least 80%, more preferably at least 85%, more preferably at least 90%, and more preferably at least 95% identical to the corresponding CL region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4.

The CH1 region of the novel scCLCH1 linker (L1) may be substantially identical to the corresponding CH1 region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. The CH1 region of L1 may have amino acid sequence that is at least 50%, 60%, 75%, 80%, 85%, 90%, 95%, 96%, 97%, 98%, or 99% identical to the corresponding CH1 region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. If the CH1 region of the L1 linker is a modified derivative or variant of a native CH1 immunoglobulin region such modifications include, but are not limited to, amino acid insertions, deletions, substitutions and rearrangements. Preferably, the amino acid sequence of the CH1 region is at least 80%, more preferably at least 85%, more preferably at least 90%, and more preferably at least 95% identical to the corresponding CH1 region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4.

The CH1 region and CL regions of L1 do not need to be identical to or a variant of, the corresponding regions of the same immunoglobulin class. For example, the CL region may be derived from the corresponding region of IgE and the CH1 region may be derived from the corresponding region of IgG.

Preferably, CL and CH1 of the scCLCH1 linker are derived from the corresponding CL and CH1 regions of IgG1, preferably human IgG1.

An exemplary CL region corresponding to the CL region of a human IgG1 (hIgG1) includes:

```
                                            (SEQ ID NO: 1)
RTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSS

PVTKSFNRGES.
```

An exemplary CH1 region corresponding to the CH1 region of hIgG1 includes:

```
                                            (SEQ ID NO: 2)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRV.
```

The single chain Fc fusion proteins disclosed herein comprise an Fc region that includes at least a portion of the carboxy-terminus of an immunoglobulin heavy chain. For example, the Fc portion may comprise: a CH2 domain, a CH3 domain, a CH4 domain, a CH2-CH3 domain, a CH2-CH4 domain, a CH2-CH3-CH4 domain, a hinge-CH2 domain, a hinge-CH2-CH3 domain, a hinge-CH2-CH4 domain, or a hinge-CH2-CH3-CH4 domain. The Fc domain may be derived from antibodies belonging any of the immunoglobulin classes, i.e., IgA, IgD, IgE, IgG, or IgM or any of the IgG antibody subclasses, i.e., IgG1, IgG2, IgG3, and IgG4. Preferably, the Fc region is derived from IgG1 preferably human IgG1.

The Fc domain may be a naturally occurring Fc sequence belonging any of the immunoglobulin classes, i.e., IgA, IgD, IgE, IgG, or IgM or any of the IgG antibody subclasses, i.e., IgG1, IgG2, IgG3, and IgG4, including natural allelic or splice variants. Alternatively, the Fc domain may be a hybrid domain comprising a portion of an Fc domain from two or more different Ig isotypes, for example, an IgG2/IgG4 hybrid Fc domain. Preferably, the Fc domain is derived from a human immunoglobulin molecule. Alternatively, the Fc domain may be a humanized or deimmunized (removal of T cell epitopes which can activate helper T cells) version of an Fc domain from a non-human animal, including but not limited to mouse, rat, rabbit, and monkey.

The Fc domain may be a variant Fc sequence, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity. For example, one may make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g. of the specific Fc region positions identified herein.

The hinge region of the Fc fusion proteins of the invention may be derived from antibodies belonging to any of the immunoglobulin classes, i.e., IgA, IgD, IgE, IgG, or IgM. The hinge region may be derived from any of the IgG antibody subclasses, i.e., IgG1, IgG2, IgG3, and IgG4. The hinge region may naturally contain a cysteine residue or may be engineered to contain one or more cysteine residues.

Preferably, the hinge region may have an amino acid sequence that is at least 50%, 60%, 75%, 80%, 85%, 90%, 95%, 96%, 97%, 98%, or 99% identical to the corresponding hinge region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. Preferably, the amino acid sequence of the hinge region is at least 80%, more preferably at least 85%, more preferably at least 90%, and more preferably at least 95% identical to the corresponding hinge region of human IgG1.

Shown below is the sequence of a human IgG1 immunoglobulin constant region, and the relative position of the hinge region is indicated by solid underlining:

```
                                            (SEQ ID NO: 3)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

The CH1 region is indicated by underlining with a dotted line, and the CH2 and CH3 regions are indicated by bold lettering. The C-terminal lysine of an IgG sequence may be removed or replaced with a non-lysine amino acid, such as alanine, to further increase the serum half-life of the Fc fusion protein.

The hinge sequence may include substitutions that confer desirable pharmacokinetic, biophysical, and/or biological properties. An exemplary hinge region of the invention comprises an amino acid sequence that is at least 50%, 60%, 75%, 80%, 85%, 90%, 95%, 96%, 97%, 98%, or 99% identical to the following: EPKSSDKTHTCPPCP (SEQ ID NO: 4).

The Fc domain and the hinge region may be derived from one antibody class or subclass. For example, the hinge region and the Fc domain may be derived from IgG1. The Fc domain and hinge region may correspond to different antibody classes or subclasses. For example, the Fc domain may correspond to the Fc region of IgG2 or IgG4 and the hinge region may correspond to IgG1.

Preferably, all immunoglobulin domains of the Fc fusion proteins of the invention are derived from IgG1, preferably human IgG1. Preferably, the combined hinge region and Fc region of the fusion proteins of the invention comprise an amino acid sequence that is at least 50%, 60%, 75%, 80%, 85%, 90%, 95%, 96%, 97%, 98%, or 99% identical to:

```
                                            (SEQ ID NO: 5)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK.
```

Preferably, the combined hinge region and Fc region of the fusion proteins of the invention comprise an amino acid sequence that is at least 50%, 60%, 75%, 80%, 85%, 90%, 95%, 96%, 97%, 98%, or 99% identical to:

```
                                            (SEQ ID NO: 6)
EPKSCDKTHTCPPCPAPELLGGPSVFLFPPKPKDTLMISRTPEVTCVVVD

VSHEDPQVKFNWYVDGVQVHNAKTKPREQQYNSTYRVVSVLTVLHQNWLD

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK.
```

It may be desirable to have a hinge sequence and/or Fc region of the single chain fusion proteins of the invention comprising a free cysteine residue in order to permit the formation of a disulfide bond between the hinge and or Fc regions thereby forming dimers of the Fc fusion proteins of the invention. It may be desirable to alter the hinge and/or Fc region sequences to remove free cysteine residues, e.g., by mutating one or more cysteine residues in a linker to another residue, such as a serine, alanine or glycine. The hinge region of the single chain fusion proteins of the invention may comprise one or more free cysteine residues capable of forming one or more disulfide bonds with a second single chain fusion protein of the invention thereby forming a dimer complex.

The X-L1-HINGE-Fc fusion proteins described herein contain an X portion that may be any soluble protein of interest or any active fragment thereof or any active derivative thereof. Soluble proteins of interest (X) that may be fused to a single chain L1-HINGE-Fc scaffold in accordance with the invention include, but are not limited to: proteins or portions or fragments thereof that that can bind to, or interact with, a target molecule, cell, complex and/or tissue, such targets including enzyme substrates, proteins, nucleic acids, carbohydrates, lipids, low molecular weight compounds, and fragments thereof.

Soluble binding proteins of interest (X) include, but are not limited to, the following list of proteins, as well as active derivatives, active fragments, subunits, domains, motifs and epitopes belonging to the following list of proteins: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR, VEGFR; interferons such as alpha interferon (α-IFN), beta interferon (β-IFN) and gamma interferon (γ-IFN); protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as AFGF and PFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des (1-3)-IGF-I (brain IGF-I), insulin-like growth factor binding proteins; CD proteins such as CD2, CD3, CD4, CD8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), e.g., interleukin-1 (IL-1), IL-2, IL-3, IL-4, IL-5, IL-6, IL-7, IL-8, IL-9, IL-10, IL-1 1. IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35; interleukin receptor antagonists such as IL1Ra; TNFα, superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD 18, CD61, CD104, beta5, beta6, beta7 and beta8; Integrin subunit combinations including but not limited to, αVβ3, αVβ5 and α4β7; a member of an apoptosis pathway; IgE; blood group antigens; flk2/flt3 receptor; obesity (OB) receptor; mp1 receptor; CTLA-4; protein C; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIbα, GPIIb/IIIa and CD200; soluble receptors such as TNFR2.

Preferably, the soluble protein of interest (X) is Factor IX, TNFR2 (also known as TNFRSF1B) or IL1Ra. Preferably the soluble protein of interest (X) is IL-10, IL-2, IL-2Rα or fusions thereof, or IFNβ. Preferably the soluble protein of interest (X is IL-10, IL-2, IL-2Rα (or fusions thereof), IFNβ, Factor IX, TNFR2 (also known as TNFRSF1B) or IL1Ra.

Figure 1B:
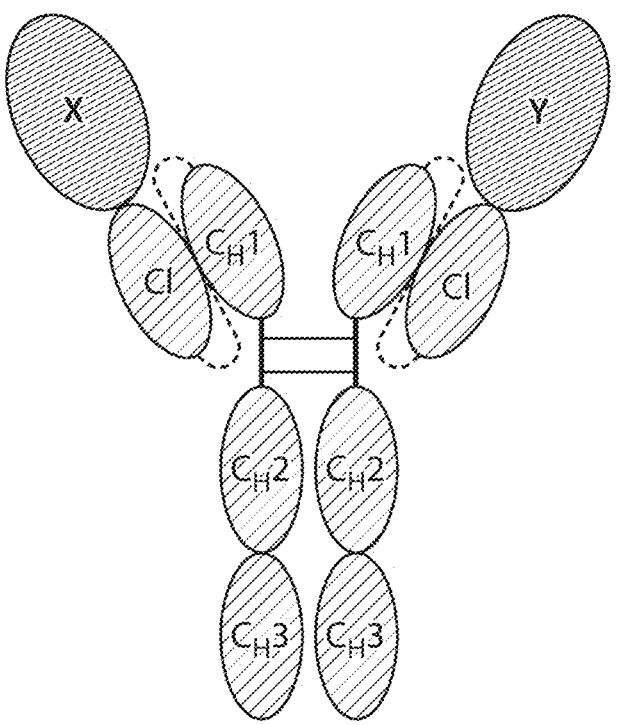
FIG. 1B is a diagram of an Fc fusion protein heterodimer of two polypeptide chains, where the first comprises X fused to the Fc region of an IgG1 antibody via the novel scCLCH1 linker, and the second comprises Y, where Y is different from X, fused to the Fc region of an IgG1 antibody via the novel scCLCH1 linker in accordance with the invention.
Figure 1C:
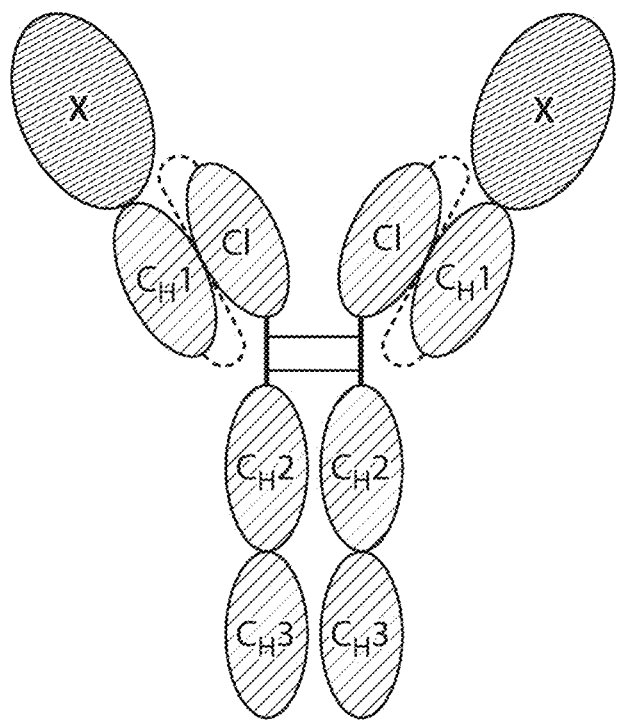
FIG. 1C is a diagram of an Fc fusion protein homodimer comprising X fused to the Fc region of an IgG1 antibody via the novel scCH1CL linker in accordance with the invention.
Figure 1D:
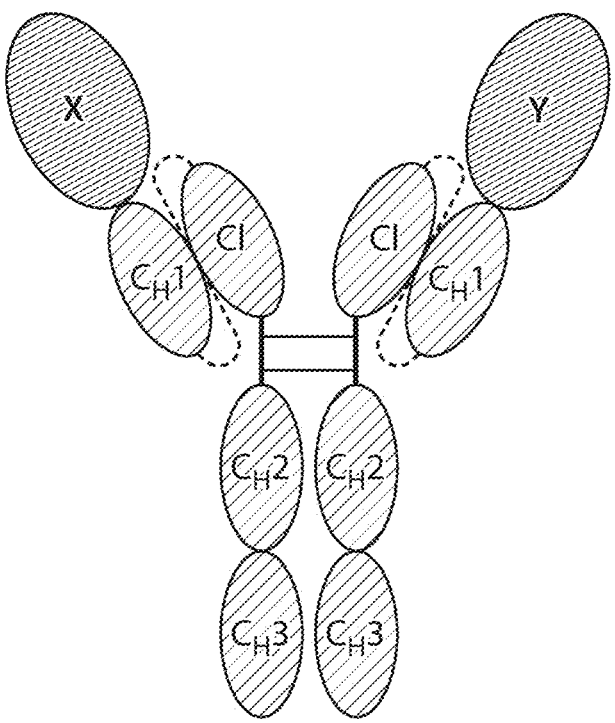
FIG. 1D is a diagram of an Fc fusion protein heterodimer of two polypeptide chains, where the first comprises X fused to the Fc region of an IgG1 antibody via the novel scCH1CL linker, and the second comprises Y, where Y is different from X, fused to the Fc region of an IgG1 antibody via the novel scCH1CL linker in accordance with the invention.

Preferably, the fusion protein has the structure of the homodimer shown in FIG. 1A where X is Factor IX, TNF-R2, or IL-1Ra or any active fragment or derivative thereof of any of the foregoing proteins. Preferably the fusion protein has the structure of the homodimers shown in FIG. 1A where X is IL-10, IL-2, IL-2Rα (or fusions thereof), or IFNβ or any active fragment or derivative of any of the foregoing proteins. Preferably, the fusion protein has the structure of the heterodimer shown in FIG. 1B where X is Factor IX, TNF-R2, or IL-1Ra and Y is different from X and is Factor IX, TNF-R2, or IL-1Ra. Preferably, the fusion protein has the structure of the heterodimer shown in FIG. 1B where X is IL-10, Factor IX, TNFR, 11-2, IL-2Rα (or fusions thereof), IFNβ or IL-1Ra and Y is different from X and is IL-10, Factor IX, TNF-R2, 11-2, IL-2Rα (or fusions thereof), IFNβ or IL-1Ra. Preferably, the fusion protein has the structure of the homodimer shown in FIG. 1C where X is Factor IX, TNF-R2, or IL-1Ra. Preferably, the fusion protein has the structure of the homodimer shown in FIG. 1C where X is IL-10, IL-2, IL-2Rα (or fusions thereof), or IFNβ. Preferably, the fusion protein has the structure of the heterodimer shown in FIG. 1D where X is Factor IX, TNF-R2, or IL-1Ra and Y is different from X and is Factor IX, TNF-R2, or IL-1Ra. Preferably, the fusion protein has the structure of the heterodimer shown in FIG. 1D where X is IL-10, Factor IX, TNF-R2, 11-2, IL-2Rα (or fusions thereof), IFNβ or IL-1Ra and Y is different from X and is IL-10, Factor IX, TNF-R2, 11-2, IL-2Rα (or fusions thereof), IFNβ or IL-1Ra.

Preferably, the soluble protein X of the formula X-L1-HINGE-Fc is factor IX and a single chain fusion protein of the invention having the formula X-L1-HINGE-Fc comprising an amino acid sequence that is 50%, 60%, 75%, 80%, 85%, 90%, 95%, 96%, 97%, 98%, or 99% identical to:

```
                                            (SEQ ID NO: 7)
TVFLDHENANKILNRPKRYNSGKLEEFVQGNLERECMEEKCSFEEAREV

FENTERTTEFWKQYVDGDQCESNPCLNGGSCKDDINSYECWCPFGFEGK

NCELDVTCNIKNGRCEQFCKNSADNKVVCSCTEGYRLAENQKSCEPAVP

FPCGRVSVSQTSKLTRAETVFPDVDYVNSTEAETILDNITQSTQSFNDF

TRVVGGEDAKPGQFPWQVVLNGKVDAFCGGSIVNEKWIVTAAHCVETGV

KITVVAGEHNIEETEHTEQKRNVIRIIPHHNYNAAINKYNHDIALLELD

EPLVLNSYVTPICIADKEYTNIFLKFGSGYVSGWGRVFHKGRSALVLQY

LRVPLVDRATCLRSTKFTIYNNMFCAGFHEGGRDSCQGDSGGPHVTEVE

GTSFLTGIISWGEECAMKGKYGIYTKVSRYVNWIKEKTKLTGGGSGGG

GSRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSS

PVTKSFNRGESGGGGSGGGGSGGGGSGGGGSASTKGPSVFPLAPSSKST

SGGTAALGCLVKDYFPEPVTVSWNSGALTSGVHTFPAVLQSSGLYSLSS

VVTVPSSSLGTQTYICNVNHKPSNTKVDKRVEPKSSDKTHTCPPCPAPE

LLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAP
```

-continued
```
IEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMH

EALHNHYTQKSLSLSPGK.
```

Preferably, the soluble protein X of the formula X-L1-HINGE-Fc is TNFR2 and a single chain fusion protein of the invention having the formula X-L1-HINGE-Fc comprising an amino acid sequence that is 50%, 60%, 75%, 80%, 85%, 90%, 95%, 96%, 97%, 98%, or 99% identical to:

```
                                            (SEQ ID NO: 8)
LPAQVAFTPYAPEPGSTCRLREYYDQTAQMCCSKCSPGQHAKVFCTKTSD

TVCDSCEDSTYTQLWNWVPECLSCGSRCSSDQVETQACTREQNRICTCRP

GWYCALSKQEGCRLCAPLRKCRPGFGVARPGTETSDVVCKPCAPGTFSNT

TSSTDICRPHQICNVVAIPGNASMDAVCTSTSPTRSMAPGAVHLPQPVST

RSQHTQPTPEPSTAPSTSFLLPMGPSPPAEGSTGDGGGGSGGGGSRTVAA

PSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRG

ESGGGGSGGGGSGGGGSGGGGSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPQVKFNWYVDGVQVHNAKTKPREQQ

YNSTYRVVSVLTVLHQNWLDGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK.
```

Preferably, the soluble protein X of the formula X-L1-HINGE-Fc is IL1Ra and a single fusion protein of the invention having the formula X-L1-HINGE-Fc comprises an amino acid sequence that is 50%, 60%, 75%, 80%, 85%, 90%, 95%, 96%, 97%, 98%, or 99% identical to:

```
                                            (SEQ ID NO: 9)
RPSGRKSSKMQAFRIWDVNQKTFYLRNNQLVAGYLQGPNVNLEEKIDVVP

IEPHALFLGIHGGKMCLSCVKSGDETRLQLEAVNITDLSENRKQDKRFAF

IRSDSGPTTSFESAACPGWFLCTAMEADQPVSLTNMPDEGVMVTKFYFQE

DEGGGGSGGGGSRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGESGGGSGGGGSGGGGSGGGGSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKRVEPKSSDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK.
```

Preferably, the soluble protein X of the formula X-L1-HINGE-Fc is IFNβ and a single fusion protein of the invention having the formula X-L1-HINGE-Fc comprising an amino acid sequence that is 50%, 60%, 75%, 80%, 85%, 90%, 95%, 96%, 97%, 98%, or 99% identical to:

(SEQ ID NO: 18)
MSYNLLGFLQRSSNFQSQKLLWQLNGRLEYCLKDRMNFDIPEEIKQLQQF

QKEDAALTIYEMLQNIFAIFRQDSSSTGWNETIVENLLANVYHQINHLKT

VLEEKLEKEDFTRGKLMSSLHLKRYYGRILHYLKAKEYSHCAWTIVRVEI

LRNFYFINRLTGYLRNGGGGSGGGGSRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGECGGGGSGGGGSGGGGSGG

GGSASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVDKR

VEPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVDK

SRWQGNVFSCSVMHEALHNHYTQKSLSLSPGK..

Preferably, the soluble protein X of the formula X-L1-HINGE-Fc comprises a protein that has been modified by circular permutation as is described in International Publication Number WO 2013/184942. Circular permutation involves the linking of the native amino and carboxy ends of a protein, generally with a linker, and creating new amino and carboxy termini by cleaving at a new site within the protein sequence, generally a loop; such that the primary sequence of the resulting protein is reordered, while the secondary structure (and activity) is retained. Thus, creation of the new termini may provide better locations for attachment of a fusion partner relative to the native termini. Circular permutation of a protein ligand provides a means by which a protein may be altered to produce new carboxyl and amino termini without diminishing the specificity and binding affinity of the altered protein ligand for its target relative to its native form. Additionally, the new termini can be preferentially moved to a location preferential for incorporating the circularly permuted ligand into a fusion polypeptide, and demonstrate better activity compared with a fusion polypeptide containing the native (non-circularly permuted) ligand.

Preferably, the soluble protein X of formula X-L1-HINGE-Fc comprises a fusion of two different proteins designated as Q-R and wherein Q and R may be fused via an optional linker L5. Preferably Q is a soluble ligand which can form a signaling complex with a membrane associated receptor and R is the extracellular domain of one receptor chain from the membrane associated receptor. Preferably, Q-L5-R is IL-2 or circularly permuted IL-2 fused to the extracellular domain of IL-2Rα via an optional linker.

Preferably, the soluble protein X of the formula X-L1-HINGE-Fc is a fusion of IL-2/IL-2Rα wherein the single chain protein comprises an amino acid sequence that is 50%, 60%, 75%, 80%, 85%, 90%, 95%, 96%, 97%, 98%, or 99% identical to:

(SEQ ID NO: 19)
SKNFHLRPRDLISNINVIVELKGSETTFMCEYADETATIVEFLNRWITFS

QSIISTLTGGSSSTKKTQLQLEHLLLDLQMILNGINNYKNPKLTRMLTFK

FYMPKKATELKHLQCLEEELKPLEEVLNLAQGSGGGSELCDDDPPEIPHA

TFKAMAYKEGTMLNCECKRGFRRIKSGSLYMLCTGNSSHSSWDNQCQCTS

SATRNTTKQVTPQPEEQKERKTTEMQSPMQPVDQASLPGHCREPPPWENE

ATERIYHFVVGQMVYYQCVQGYRALHRGPAESVCKMTHGKTRWTQPQLIC

TGGGGGSGGGSRTVAAPSVFIFPPSDEQLKSGTASVVCLLNNFYPREAKV

QWKVDNALSGNSQESVTEQDSKDSTYSLSSTLTLSKADYEKHKVYACEVT

HQGLSSPVTKSFNRGECGGGGSGGGGSGGGGSGGGGSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKRVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK.

Preferably, the soluble protein X of the formula X-L1-HINGE-Fc is a fusion of IL-2/IL-2Rα wherein the single chain protein comprises an amino acid sequence that is 50%, 60%, 75%, 80%, 85%, 90%, 95%, 96%, 97%, 98%, or 99% identical to:

(SEQ ID NO: 20)
SKNFHLRPRDLISNINVIVELKGSETTFMCEYADETATIVEFLNRWITF

SQSIISTLTGGSSSTKKTQLQLEHLLLDLQMILNGINNYKNPKLTRMLTF

KFYMPKKATELKHLQCLEEELKPLEEVLNLAQGSGGGSELCDDDPPEIPH

ATFKAMAYKEGTMLNCECKRGFRRIKSGSLYMLCTGNSSHSSWDNQCQCT

SSATRNTTKQVTPQPEEQKERKTTEMQSPMQPVDQASLPGHCREPPPWEN

EATERIYHFVVGQMVYYQCVQGYRALHRGPAESVCKMTHGKTRWTQPQLI

CTGGGGGSGGGGSASTKGPSVFPLAPSSKSTSGGTAALGCLVKDYFPEPV

TVSWNSGALTSGVHTFPAVLQSSGLYSLSSVVTVPSSSLGTQTYICNVNH

KPSNTKVDKRVGGGGSGGGGSGGGGSRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGECGGSGGEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGK..

Preferably, the soluble protein X of the formula X-L1-HINGE-Fc is IL-10 wherein the single chain protein comprises an amino acid sequence that is 50%, 60%, 75%, 80%, 85%, 90%, 95%. 96%. 97%. 98%. or 99% identical to:

(SEQ ID NO: 23)
MYRMQLLSCIALSLALVTNSSPGQGTQSENSCTHFPGNLPNMLRDLRDAF
SRVKTFFQMKDQLDNLLLKESLLEDFKGYLGCQALSEMIQFYLEEVMPQA
ENQDPDIKAHVNSLGENLKTLRLRLRRCHRFLPCENKSKAVEQVKNAFNK
LQEKGIYKAMSEFDIFINYIEAYMTMKIRNGGSGGGGSGGSPGQGTQSEN
SCTHFPGNLPNMLRDLRDAFSRVKTFFQMKDQLDNLLLKESLLEDFKGYL
GCQALSEMIQFYLEEVMPQAENQDPDIKAHVNSLGENLKTLRLRLRRCHR
FLPCENKSKAVEQVKNAFNKLQEKGIYKAMSEFDIFINYIEAYMTMKIRN
GGGGSGGGGSRTVAAPSVFIFPPSDEQLKSGTASVVCLLNNFYPREAKVQ
WKVDNALQSGNSQESVTEQDSKDSTYSLSSTLTLSKADYEKHKVYACEVT
HQGLSSPVTKSFNRGECGGGGSGGGGSGGGGSGGGGSASTKGPSVFPLAP
SSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCP
APELLGGPSVFLEPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHE
ALHNHYTQKSLSLSPGK.

Preferably, the soluble protein X of the formula X-L1-HINGE-Fc is IL-10 wherein the single chain protein comprises an amino acid sequence that is 50%, 60%, 75%, 80%, 85%, 90%, 95%, 96%, 97%, 98%, or 99% identical to:

(SEQ ID NO: 24)
MYRMQLLSCIALSLALVTNSSPGQGTQSENSCTHFPGNLPNMLRDLRDAF
SRVKTFFQMKDQLDNLLLKESLLEDFKGYLGCQALSEMIQFYLEEVMPQA
ENQDPDIKAHVNSLGENLKTLRLRLRRCHRFLPCENKSKAVEQVKNAFNK
LQEKGIYKAMSEFDIFINYIEAYMTMKIRNGGSGGGGSGGSPGQGTQSEN
SCTHFPGNLPNMLRDLRDAFSRVKTFFQMKDQLDNLLLKESLLEDFKGYL
GCQALSEMIQFYLEEVMPQAENQDPDIKAHVNSLGENLKTLRLRLRRCHR
FLPCENKSKAVEQVKNAFNKLQEKGIYKAMSEFDIFINYIEAYMTMKIRN
GGGGSGGGGSASTKGPSVFPLAPSSKSTSGGTAALGCLVKDYFPEPVTVS
WNSGALTSGVHTFPAVLQSSGLYSLSSVVTVPSSSLGTQTYICNVNHKPS
NTKVDKRVGGGSGGGGSGGGGSGGGGSRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSFNRGECGGSSGGEPKSCDKTHT
CPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSC
SVMHEALHNHYTQKSLSLSPGK.

Preferably, the X-L1-HINGE-Fc fusion proteins of the invention are dimer complexes comprising two monomeric single chain X-L1-HINGE-Fc fusion proteins of the invention linked via a disulfide bond to the hinge region or in the Fc region of the other monomer. The dimer complexes may be homodimeric (e.g. both monomeric fusion proteins are identical) or heterodimeric (e.g. the protein of interest (X) may be different for each monomeric fusion protein). Preferably, the dimer complexes are homodimers thereby forming a homodimeric complex that provides an antibody configuration that resembles that of a native antibody.

Without being limited to any one theory, it is believed that the homodimeric fusion proteins of the invention increase half-life due to the presence of a dimerized Fc region which more closely resembles the native antibody structure as compared to traditional Fc fusion proteins. A more native Fc domain antibody configuration is believed to enable better binding to the FcRn receptor and therefore increase the circulating half-life of the of the X-L1-HINGE-Fc dimer complex.

Another improved property associated with X-L1-HINGE-Fc dimer complexes is that bioactivity is increased versus a traditional Fc fusion proteins based on the use of the scCLCH1 linker which imparts flexibility to relieve steric hindrance caused by the dimerization through the Fc in the hinge region.

Recombinant Production of X-L1-HINGE-Fc Fusion Proteins

The invention also provides nucleic acids encoding any of the various Fc fusion proteins disclosed herein. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*, 100(2):438-442 (Jan. 21, 2003); Sinclair et al., *Protein Expr. Purif.*, 26(I):96-105 (October 2002); Connell, N. D., *Curr. Opin. Biotechnol.*, 12(5):446-449 (October 2001); Makrides et al., *Microbiol Rev.*, 60(3): 512-538 (September 1996); and Sharp et al., *Yeast*, 7(7): 657-678 (October 1991).

General techniques for nucleic acid manipulation are described for example in Sambrook et al., *Molecular Cloning: A Laboratory Manual*, 2nd Edition, Vols. 1-3, Cold Spring Harbor Laboratory Press (1989), or Ausubel, F. et al., *Current Protocols in Molecular Biology*, Green Publishing and Wiley-Interscience, New York (1987) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The Fc fusion proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. An exemplary N-terminal leader sequence for production of polypeptides in a mammalian system is MYRMQLLSCIALSLALVTNS (SEQ ID NO: 10), which is removed by the host cell following expression.

For prokaryotic host cells that do not recognize and process a native signal sequence, the signal sequence is substituted by a prokaryotic signal sequence selected, for example, from the group of the alkaline phosphatase, penicillinase, or heat-stable enterotoxin II leaders.

For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein disclosed herein, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein disclosed herein. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO: 16) region where N may be any nucleotide. At the 3' end of most eukaryotic genes is an AATAAA (SEQ ID NO: 17) sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding proteins disclosed herein by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature,* 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein disclosed herein. One useful transcription termination component is the bovine growth hormone polyadenylation region. See WO 94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual,* (Elsevier, New York (1985)), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae,* may also be used for production of polypeptides. Various mammalian or insect cell culture systems can also be employed to express recombinant proteins. Baculovirus systems for production of heterologous proteins in insect cells are reviewed by Luckow et al. (*Bio/Technology,* 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

In other aspects, the invention provides host cells containing vectors encoding the Fc fusion proteins described herein, as well as methods for producing the Fc fusion proteins described herein. Host cells may be transformed with the herein-described expression or cloning vectors for protein production and cultured in conventional nutrient media modified as appropriate for inducing promoters, selecting transformants, or amplifying the genes encoding the desired sequences. Host cells useful for high-throughput protein production (HTPP) and mid-scale production include the HMS 174-bacterial strain. The host cells used to produce the proteins disclosed herein may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), Sigma)) are suitable for culturing the host cells. In addition, many of the media described in various scientific literature may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The Fc fusion proteins provided herein can also be produced using cell-translation systems. For such purposes the nucleic acids encoding the fusion protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

The Fc fusion proteins disclosed herein can also be produced by chemical synthesis (e.g., by the methods described in *Solid Phase Peptide Synthesis,* 2nd Edition, The Pierce Chemical Co., Rockford, Ill. (1984)). Modifications to the Fc fusion proteins can also be produced by chemical synthesis.

The Fc fusion proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified Fc fusion protein is preferably at least 85% pure, or preferably at least 95% pure, and most preferably at least 98% pure. Regardless of the exact numerical value of the purity, the Fc fusion protein is sufficiently pure for use as a pharmaceutical product.

Uses of X-L1-HINGE-Fc Fusion Proteins

In one aspect, the invention provides Fc fusion proteins that are useful as diagnostic or therapeutic agents. In one aspect, the invention provides Fc fusion proteins useful in the treatment of disorders. The diseases or disorders that may be treated will be dictated by the identity of the protein (X) fused to the Fc domain via the novel L1 linker of the invention and include, but are not limited to: cancer, inflammatory diseases, arthritis, osteoporosis, infections in particular hepatitis, bacterial infections, viral infections, genetic diseases, pulmonary diseases, diabetes, hormone-related disease, Alzheimer's disease, cardiac diseases, myocardial infarction, deep vein thrombosis, diseases of the circulatory system, hypertension, hypotension, allergies, pain relief, dwarfism and other growth disorders, intoxications, blot clotting diseases, diseases of the innate immune system, embolism, wound healing, healing of burns, Crohn's disease, asthma, ulcer, sepsis, glaucoma, cerebrovascular ischemia, respiratory distress syndrome, corneal ulcers, renal disease, diabetic foot ulcer, anemia, factor IX deficiency, factor VIII deficiency, factor VII deficiency, mucositis, dysphagia, thrombocyte disorder, lung embolism, infertility, hypogonadism, leucopenia, neutropenia, endometriosis, Gaucher disease, obesity, lysosome storage disease, AIDS, premenstrual syndrome, Turners syndrome, cachexia, muscular dystrophy, Huntington's disease, colitis, SARS, Kaposi sarcoma, liver tumor, breast tumor, glioma, Non-Hodgkin lymphoma, Chronic myelocytic leukemia; Hairy cell leukemia; Renal cell carcinoma; Liver tumor; Lymphoma; Melanoma, multiple sclerosis, Kaposis sarcoma, papilloma virus, emphysema, bronchitis, periodontal disease, dementia, parturition, non-small cell lung cancer, pancreas tumor, prostate tumor, acromegaly, psoriasis, ovary tumor, Fabry disease, lysosome storage disease.

Exemplary therapeutic soluble proteins (X) that may be bound to an Fc domain include, for example, factor IX, IL1Ra, and TNFR. Exemplary therapeutic soluble proteins (X) that may be bound to an Fc domain include, for example, IL-10, IL-2, IL-2Rα or fusions thereof, or IFNβ. Exemplary therapeutic soluble proteins (X) that may be bound to an Fc domain include, for example, IL-10, IL-2, IL-2Ra or fusions thereof, IFNβ, factor IX, IL1Ra, and TNFR2.

The invention also provides a method for achieving a beneficial effect in a subject comprising the step of administering to the subject a therapeutically or prophylactically-effective amount of a fusion protein. The effective amount can produce a beneficial effect in helping to treat a disease or disorder. In some cases, the method for achieving a beneficial effect can include administering a therapeutically effective amount of a fusion protein composition to treat a subject for diseases and disease categories wherein a therapeutic protein or peptide does not exist.

Preferably, the invention provides a fusion protein X-L1-HINGE-Fc wherein X is factor IX. Preferably, the invention provides a dimer complex of X-L1-HINGE-Fc wherein X is factor IX. Preferably the dimer complex is a homodimer complex. Factor IX fusion proteins in accordance with the invention may be used to treat patients who are deficient in factor IX and suffer from hemophilia B for e.g., control and prevention of bleeding episodes, routine prophylaxis to prevent or reduce the frequency of bleeding episodes, and perioperative management (surgical prophylaxis).

A patient in need of control or prevention of bleeding or bleeding episodes is preferably a human patient. The patient can be bleeding at the time of administration or be expected to be bleeding, or can be susceptible to bleeding in minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Such patients also include those in need of perioperative management, such as management of bleeding associated with surgery or dental extraction. The patient is preferably in need of prophylaxis of one or more bleeding episodes. The patient is preferably in need of individualized interval prophylaxis. The patient is preferably in need of on-demand treatment of one or more bleeding episodes. The patient is preferably in need of perioperative management of one or more bleeding episodes.

When treating hemophilia with a fusion protein of the invention comprising factor IX, an "effective dose" reduces or decreases frequency of bleeding or bleeding disorder. An "effective dose" preferably stops on-going, uncontrollable bleeding or bleeding episodes. Preferably an "effective dose" prevents spontaneous bleeding or bleeding episodes in a subject susceptible to such spontaneous bleeding or bleeding episodes. A "therapeutic dose" need not cure hemophilia.

Preferably, the invention provides a fusion protein X-L1-HINGE-Fc wherein X is IL-10. Preferably, the invention provides a dimer complex of X-L1-HINGE-Fc wherein X is IL-10. Preferably the dimer complex is a homodimer complex. An IL-10 fusion protein and/or a dimerized complex thereof in accordance with the invention may be used to treat patients who suffer from, for example, autoimmune disorders, fibrotic diseases, inflammatory diseases, ischemic diseases, neurodegenerative diseases, neuropathic diseases, pain disorders, auditory disorders, psychiatric disorders, cancer and trauma and injury.

Examples of autoimmune disorders which may be treated by the IL-10 fusion proteins of the invention include, but are not limited to: acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune lymphoproliferative syndrome (ALPS), autoimmune myocarditis, autoimmune oophoritis, autoimmune pancreatitis, autoimmune retinopathy, autoimmune thrombocytopenic purpura (ATP), autoimmune thyroiditis, autoimmune urticaria, axonal & neuronal neuropathies, Balo disease, Behcet's disease, cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), cicatricial pemphigoid/benign mucosal pemphigoid, Cogans syndrome, cold agglutinin disease, congenital heart block, Coxsackie myocarditis, CREST disease, Crohn's disease, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, essential mixed cryoglobulinemia, Evans syndrome, experimental allergic encephalomyelitis, fibromyalgia, fibrosing alveolitis, giant cell arteritis (temporal arteritis), giant cell myocarditis, glomerulonephritis, Goodpasture's syndrome, granulomatosis with Polyangiitis (GPA) (formerly called Wegener's Granulomatosis), Grave's disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic pulmonary fibrosis, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile diabetes (Type 1 diabetes), juvenile myositis, Kawasaki disease, Lambert-Eaton syndrome, leukocytoclastic vasculitis, lichen planus, lichen sclerosus, ligneous conjunctivitis, linear IgA disease (LAD), Lupus (systemic lupus erythematosus), Lyme disease, chronic, Meniere's disease, microscopic polyangiitis, mixed connective tissue disease (MCTD), Mooren's ulcer, Mucha-Habermann disease, multiple sclerosis (MS), myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paroxysmal nocturnal hemoglobinuria (PNH), Parry Romberg syndrome, Pars planitis (peripheral uveitis), Parsonnage-Turner syndrome, pemphigus, peripheral neuropathy, perivenous encephalomyelitis, pernicious anemia, POEMS syndrome, polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynauds phenomenon, reactive Arthritis, reflex sympathetic dystrophy, Reiter's syndrome, relapsing polychondritis, restless legs syndrome, retroperitoneal fibrosis, rheumatic fever, rheumatoid arthritis (RA), rheumatoid arthritis, sarcoidosis, Schmidt syndrome, scleritis, scleroderma, Sjogren's syndrome, sperm & testicular autoimmunity, stiff person syndrome, subacute bacterial endocarditis, Susac's syndrome, sympathetic ophthalmia, Takayasu's arteritis, Temporal arteritis/Giant cell arteritis, thrombocytopenic purpura, Tolosa-Hunt syndrome, transverse myelitis, type 1 diabetes, type I, II, & III autoimmune polyglandular syndromes, ulcerative colitis, undifferentiated connective tissue disease (UCTD), uveitis, vasculitis, vesiculobullous dermatosis, vitiligo, and Wegener's granulomatosis.

Examples of fibrotic diseases which may be treated by the IL-10 fusion proteins of the invention include, but are not limited to: adhesive capsulitis, arthrofibrosis, atrial fibrosis, chronic kidney disease, cirrhosis of the liver, cystic fibrosis (CF), Dupuytren's contracture, endomyocardial fibrosis, glial scar, idiopathic pulmonary fibrosis, keloid, macular degeneration, mediastinal fibrosis, myelofibrosis, NAFLD/NASH, nephrogenic systemic fibrosis, Peyronie's disease, progressive massive fibrosis (lungs), proliferative vitreoretinopathy, pulmonary fibrosis, retroperitoneal fibrosis, scar tissue formation resulting from strokes, scleroderma, systemic sclerosis, tissue adhesion.

Examples of inflammatory diseases which may be treated by the IL-10 fusion proteins of the invention include, but are not limited to: allergic enteritis, alpha-1-antitrypsin deficiency, ankylosing spondylitis, asthma, Barrett's esophagus, Behcet's disease, chronic fatigue syndrome (CFS/CFIDS/ME), chronic Lyme disease (borreliosis), cocaine-associated vasculitis, Crohn's disease, deficiency of the Interleukin-1 Receptor Antagonist (DIRA), depression, diabetes, Familial Mediterranean Fever (FMF), fibromyalgia (FM), gastroesophageal reflux disease (GERD), glomerulonephritis, graft versus host disease, granulomatous angiitis, Hashimoto's thyroiditis, hypertension, hyperthyroidism, hypothyroidism, inflammatory bowel disease (IBD), inflammatory myopathies (polymyositis, inclusion body myositis, dermatomyositis), interstitial cystitis (IC), irritable bowel syndrome (IBS), ischemic colitis, kidney stones, Löfgren's syndrome, Lupus erythematosis, methamphetamine-associated vasculitis, migraine headache, Morgellon's, multiple chemical sensitivity (MCS), multiple sclerosis (MS), neonatal onset multisystem inflammatory disease (NOMID), optic neuritis, osteoarthritis, pemphigus vulgaris, polymyalgia rheumatica, prostatitis, psoriasis, psoriatic arthritis, radiation colitis, Raynaud's syndrome/phenomenon, reactive arthritis (Reiter syndrome), reflex sympathetic dystrophy (RSD), restless leg syndrome, rheumatoid arthritis (RA), sarcoidosis, scleroderma, seasonal affective disorder (SAD), septic shock, sinusitis, Sjögren's syndrome, temporal arteritis, tumor necrosis factor (TNF) receptor-associated periodic syndrome (TRAPS), ulcerative colitis, uveitis, vasculitis, and vertigo.

Examples of ischemic diseases which may be treated by the IL-10 fusion proteins of the invention include, but are not limited to: acute coronary syndrome, angina pectoris, angor animi, copeptin, coronary artery disease, coronary ischemia, hibernating myocardium, ischemic stroke, management of acute coronary syndrome, meldonium, myocardial infarction, myocardial infarction complications, myocardial infarction diagnosis, myocytolysis, post-anoxic encephalopathy, Prinzmetal's angina, Sgarbossa's criteria, stroke, TIMI, transient ischemic attack (TIA) and unstable angina.

Examples of neurodegenerative diseases which may be treated by the IL-10 fusion proteins of the invention include, but are not limited to: ataxia telangiectasia, autosomal dominant cerebellar ataxia, Baggio-Yoshinari syndrome, Batten disease, estrogen and neurodegenerative diseases, hereditary motor and sensory neuropathy with proximal dominance, Infantile Refsum disease, JUNQ and IPOD, locomotor ataxia, Lyme disease, Machado-Joseph disease, mental retardation and microcephaly with pontine and cerebellar hypoplasia, multiple system atrophy, neuroacanthocytosis, neuronal ceroid lipofuscinosis, Niemann-Pick disease, pontocerebellar hypoplasia, protein aggregation, pyruvate dehydrogenase deficiency, radiation myelopathy, Refsum disease, retinitis pigmentosa, Sandhoff disease, Shy-Drager syndrome, spinal muscular atrophy, spinocerebellar ataxia, subacute combined degeneration of spinal cord, subacute sclerosing panencephalitis, Tabes dorsalis, Tay-Sachs disease, toxic encephalopathy, toxic leukoencephalopathy and Wobbly Hedgehog Syndrome.

Examples of neuropathic diseases which may be treated by the IL-10 fusion proteins of the invention include, but are not limited to: Bell's Palsy, *campylobacter*-associated motor axonopathies, Charcot-Marie-Tooth, chronic inflammatory demyelinating polyneuropathy, diabetic amyotrophy avulsion, diabetic neuropathies, Guillain Barre Syndrome and vasculitis.

Examples of pain disorders which may be treated by the IL-10 fusion proteins of the invention include, but are not limited to: Amplified musculoskeletal pain syndromes, Anterior cutaneous nerve entrapment syndrome, central pain syndrome, chronic functional abdominal pain, chronic pain, chronic prostatitis/chronic pelvic pain syndrome, chronic wound pain, degenerative disc disease, dentomandibular sensorimotor dysfunction, failed back syndrome, fibromyalgia, interstitial cystitis, irritable bowel syndrome (IBS), myofascial pain syndrome, pelvic pain, post-vasectomy pain syndrome, reflex neurovascular dystrophy, sickle-cell disease, theramine, and vulvodynia.

Examples of auditory disorders which may be treated by the IL-10 fusion proteins of the invention include, but are not limited to: conductive hearing loss, sensorineural hearing loss (SNHL), mixed hearing loss.

Examples of psychiatric disorders which may be treated by the IL-10 fusion proteins of the invention include, but are not limited to: major depressive disorder, treatment-refractory depression, treatment-resistant depression.

Examples of trauma and injury which may be treated by the IL-10 fusion proteins of the invention include, but are not limited to: including central nervous system (CNS) injuries, traumatic brain injury, spinal cord injury, crush injuries, shock, tendon damage, wounds to the cornea, wounds to the eye, skin wounds.

Preferably, an IL-10 dimerized complex in accordance with the invention may be used to treat patients who suffer from, for example, autoimmune disorders including autoimmune lymphoproliferative syndrome (ALPS), autoimmune thyroiditis, Crohn's disease, Grave's disease, Hashimoto's thyroiditis, Kawasaki disease, Lupus (systemic lupus erythematosus), multiple sclerosis (MS), myasthenia gravis, psoriasis, rheumatoid arthritis, Sjogren's syndrome, type 1 diabetes, ulcerative colitis; fibrotic diseases including Chronic Kidney Disease, cirrhosis of the liver, macular degeneration, NAFLD/NASH, proliferative vitreoretinopathy, pulmonary fibrosis, scar tissue formation resulting from strokes, tissue adhesion; including inflammatory diseases including allergic enteritis, alpha-1-antitrypsin deficiency, asthma, Behcet's disease, cocaine-associated vasculitis, glomerulonephritis, Graft Versus Host Disease, granulomatous angiitis, inflammatory bowel disease, inflammatory myopathies (polymyositis, inclusion body myositis, dermatomyositis), ischemic colitis, methamphetamine-associated vasculitis, optic neuritis, pemphigus vulgaris, radiation colitis, sarcoidosis, Septic Shock, temporal arteritis, vasculitis; ischemic diseases including myocardial infarction, post-anoxic encephalopathy, stroke; neurodegenerative diseases including neuronal ceroid lipofuscinosis, radiation myelopathy, retinitis pigmentosa, spinal muscular atrophy; neuropathic diseases including *campylobacter*-associated motor axonopathies, Charcot-Marie-Tooth, chronic inflammatory demyelinating polyneuropathy, diabetic amyotrophy avulsion, diabetic neuropathies, Guillain Barre Syndrome; auditory disorders including Conductive hearing loss, Sensorineural hearing loss (SNHL), Mixed hearing loss; psychiatric disorders including major depressive disorder, treatment-refractory depression, treatment-resistant depression; trauma and injury including central nervous system (CNS) injuries, traumatic brain injury, spinal cord injury, crush injuries, shock, tendon damage, wounds to the cornea, wounds to the eye, skin wounds.

Most preferably, an IL-10 dimerized complex in accordance with the invention may be used to treat patients who suffer from, for example, autoimmune disorders including autoimmune lymphoproliferative syndrome (ALPS), autoimmune thyroiditis, Crohn's disease, Grave's disease, Hashimoto's thyroiditis, Kawasaki disease, Lupus (systemic lupus erythematosus), multiple sclerosis (MS), myasthenia gravis, psoriasis, rheumatoid arthritis, Sjogren's syndrome, type 1 diabetes, ulcerative colitis; fibrotic diseases including Chronic Kidney Disease, cirrhosis of the liver, macular degeneration, NAFLD/NASH, proliferative vitreoretinopathy, pulmonary fibrosis, scar tissue formation resulting from strokes, tissue adhesion; inflammatory diseases including allergic enteritis, alpha-1-antitrypsin deficiency, asthma, Behcet's disease, cocaine-associated vasculitis, glomerulonephritis, Graft Versus Host Disease, granulomatous angiitis, inflammatory bowel disease, inflammatory myopathies (polymyositis, inclusion body myositis, dermatomyositis), ischemic colitis, methamphetamine-associated vasculitis, optic neuritis, pemphigus vulgaris, radiation colitis, sarcoidosis, Septic Shock, temporal arteritis, vasculitis; ischemic diseases including myocardial infarction, post-anoxic encephalopathy, stroke; neurodegenerative diseases including neuronal ceroid lipofuscinosis, radiation myelopathy, retinitis pigmentosa, spinal muscular atrophy; neuropathic diseases including campylobacter-associated motor axonopathies, Charcot-Marie-Tooth, chronic inflammatory demyelinating polyneuropathy, diabetic amyotrophy avulsion, diabetic neuropathies, Guillain Barre Syndrome; auditory disorders including Conductive hearing loss, Sensorineural hearing loss (SNHL), Mixed hearing loss; psychiatric disorders including major depressive disorder, treatment-refractory depression, treatment-resistant depression; trauma and injury including central nervous system (CNS) injuries, traumatic brain injury, spinal cord injury, crush injuries, shock, tendon damage, wounds to the cornea, wounds to the eye, skin wounds.

Preferably an IL-10 fusion protein or dimerized complex thereof in accordance with the invention may be used to treat patients who suffer from, for example cancer of the uterus, cervix, breast, ovaries, prostate, testes, penis, gastrointestinal tract, esophagus, oropharynx, stomach, small or large intestines, colon, or rectum, kidney, renal cell, bladder, bone, bone marrow, skin, head or neck, skin, liver, gall bladder, heart, lung, pancreas, salivary gland, adrenal gland, thyroid, brain, gliomas, ganglia, central nervous system (CNS) and peripheral nervous system (PNS), and immune system, spleen or thymus, papilloma virus-induced cancers, epithelial cell cancers, endothelial cell cancers, squamous cell carcinomas, adenocarcinomas, carcinomas, melanomas, sarcomas, teratocarcinomas, immunogenic tumors, non-immunogenic tumors, dormant tumors, lymphomas, leukemias, myelomas, chemically-induced cancers, metastasis, and angiogenesis, and Tuberous sclerosis.

Preferably, an IL-10 fusion protein or dimerized complex thereof in accordance with the invention may be used to treat patients who suffer from, for example cancer of the uterus, cervix, breast, ovaries, prostate, testes, penis, gastrointestinal tract, esophagus, oropharynx, stomach, small or large intestines, colon, or rectum, kidney, renal cell, bladder, bone, bone marrow, skin, head or neck, skin, liver, gall bladder, heart, lung, pancreas, salivary gland, adrenal gland, thyroid, brain, gliomas, ganglia, central nervous system (CNS) and peripheral nervous system (PNS), and immune system, spleen or thymus, papilloma virus-induced cancers, epithelial cell cancers, endothelial cell cancers, squamous cell carcinomas, adenocarcinomas, carcinomas, melanomas, sarcomas, teratocarcinomas, immunogenic tumors, non-immunogenic tumors, dormant tumors, lymphomas, leukemias, myelomas, chemically-induced cancers, metastasis, and angiogenesis, and Tuberous sclerosis.

Preferably, an IL-10 fusion protein or dimerized complex thereof in accordance with the invention may be used to treat patients who suffer from, for example cancer of the uterus, cervix, breast, ovaries, prostate, testes, penis, gastrointestinal tract, esophagus, oropharynx, stomach, small or large intestines, colon, or rectum, kidney, renal cell, bladder, bone, bone marrow, skin, head or neck, skin, liver, gall bladder, heart, lung, pancreas, salivary gland, adrenal gland, thyroid, brain, gliomas, ganglia, central nervous system (CNS) and peripheral nervous system (PNS), and immune system, spleen or thymus, papilloma virus-induced cancers, epithelial cell cancers, endothelial cell cancers, squamous cell carcinomas, adenocarcinomas, carcinomas, melanomas, sarcomas, teratocarcinomas, immunogenic tumors, non-immunogenic tumors, dormant tumors, lymphomas, leukemias, myelomas, chemically-induced cancers, metastasis, and angiogenesis, and Tuberous sclerosis.

Preferably, an IL-10 fusion protein or dimerized complex thereof in accordance with the invention may be used to treat patients who suffer from auditory disorders, renal cell carcinoma, melanoma, psoriasis, fibrosis, depression, and inflammatory bowel disease (IBD).

The invention also provides Fc fusion proteins of the inventions for use as a medicament. Preferably, the invention provides a fusion protein X-L1-HINGE-Fc wherein X is a soluble protein of interest as described earlier for use as a medicament. Preferably X is factor IX, IL1Ra, or TNFR. Preferably X is IL-10, IL-2, IL-2Rα (or fusions thereof), or IFNβ for use as a medicament. Preferably the invention provides a dimer complex of X-L1-HINGE-Fc wherein X is a soluble protein of interest as described earlier for use as a medicament.

The invention also provides Fc fusion proteins of the inventions for use as a medicament to treat disease. Preferably, the invention provides a fusion protein X-L1-HINGE-Fc wherein X is a soluble protein of interest as described earlier for use as a medicament to treat diseases as described earlier. Preferably X is factor IX, for use as a medicament to treat bleeding. Preferably X is IL-10 for treatment of Crohn's disease (CD), rheumatoid arthritis (RA), psoriasis, viral infections such as chronic hepatitis C and human immunodeficiency virus (HIV).

Preferably the invention provides a dimer complex of X-L1-HINGE-Fc wherein X is a soluble protein of interest as described earlier for use as a medicament to treat disease. Preferably X is factor IX, IL1Ra, or TNFR, for use as a medicament to treat cancer, autoimmune disease and bleeding disorders. Preferably X is IL-10, IL-2, IL-2Rα or fusions thereof, or IFNβ for use in treating, for example, auditory disorders, renal cell carcinoma, melanoma, psoriasis, fibrosis, depression, and inflammatory bowel disease (IBD).

A factor IX dimerized fusion protein complex in accordance with the invention may also be used in the manufacture of a medicament to treat patients who are deficient in factor IX and suffer from hemophilia B for e.g., control and prevention of bleeding episodes, routine prophylaxis to prevent or reduce the frequency of bleeding episodes, and perioperative management (surgical prophylaxis).

An IL-10 fusion protein or dimerized complex thereof in accordance with the invention may also be used in the manufacture of a medicament to treat patients to diseases as set forth above, auditory disorders, auditory disorders, renal cell carcinoma, melanoma, psoriasis, fibrosis, depression, and inflammatory bowel disease (IBD).

The application further provides pharmaceutically acceptable compositions comprising the Fc fusion proteins described herein. Therapeutic formulations comprising Fc fusion proteins are prepared for storage by mixing the described proteins having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations herein may also contain more than one active compounds as necessary for the particular indication being treated, preferably those with complementary activities that do not adversely affect each other. Such molecules are suitably present in combination in amounts that are effective for the purpose intended.

The Fc fusion proteins may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the fibronectin based scaffold proteins described herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides, copolymers of lactide and glycolide, copolymers of L-glutamic acid and y ethyl-L-glutamate, non-degradable ethylene-vinyl acetate, degradable lactic acid-glycolic acid copolymers. While polymers such as ethylene-vinyl acetate and lactic acid-glycolic acid enable sustained release of, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

While the skilled artisan will understand that the dosage of each Fc fusion protein will be dependent on the identity of the soluble protein (X), the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-30 mg/kg. An exemplary treatment regime entails administration once per week, once every two weeks, once every three weeks, once every four weeks, once a month, once every 3 months or once every three to 6 months. Dosage regimens include 1 mg/kg body weight or 3 mg/kg body weight by intravenous administration, with the protein being given using one of the following dosing schedules: every four weeks for six dosages, then every three months; every three weeks; 3 mg/kg body weight once followed by 1 mg/kg body weight every three weeks. A fusion protein of the invention is usually administered on multiple occasions. Intervals between single dosages can be, for example, weekly, monthly, every three months or yearly. Intervals can also be irregular as indicated by measuring blood levels of the soluble protein in the patient. In some methods, dosage is adjusted to achieve a plasma concentration of soluble protein of about 0.1-1000 pg/ml and in some methods about 5-300 mg/ml.

For therapeutic applications, the Fc fusion proteins are administered to a subject, in a pharmaceutically acceptable dosage form. They can be administered intravenously as a bolus or by continuous infusion over a period of time, by intramuscular, subcutaneous, intra-ocular, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The methods of the present invention can be practiced in vitro, in vivo, or ex vivo.

Administration of Fc fusion proteins, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, the Fc fusion protein typically will be formulated at a concentration of about 0.1 mg/ml to 100 mg/ml, although wide variation outside of these ranges is permitted. For the treatment of disease, the appropriate dosage of Fc fusion proteins will depend on the type of disease to be treated, the severity and course of the disease, whether the Fc fusion proteins are administered for preventive or therapeutic purposes, the course of previous therapy, the patient's clinical history and response to the Fc fusion protein, and the discretion of the attending physician. The Fc fusion protein is suitably administered to the patient at one time or over a series of treatments.

EXAMPLES

Example 1: Factor IX
Design of Factor IX scC$_L$C$_H$1-Fc
The single chain factor IX molecule contains the factor IX sequence followed by a 10 residue linker having the amino acid sequence: GGGGSGGGGS (SEQ ID NO: 11), the CL domain of IgG1 followed by a 20 residue linker having the amino acid sequence: GGGGSGGGGSGGGGSGGGGS (SEQ ID NO: 12) followed by the CH1, hinge and Fc portions of human IgG1.
Expression and Characterization of Factor IX scC$_L$C$_H$1-Fc
The gene, having the following DNA sequence:

```
                                    (SEQ ID NO: 13)
ATGTACCGGATGCAGCTGCTGAGCTGTATCGCCCTGTCTCTGGCCCTCGT

GACCAACAGCACCGTGTTTCTGGACCACGAGAACGCCAACAAGATCCTGA

ACCGGCCCAAGCGGTACAACAGCGGCAAGCTGGAAGAGTTCGTGCAGGGC

AACCTGGAACGCGAGTGCATGGAAGAGAAGTGCAGCTTCGAAGAGGCCAG

AGAGGTGTTCGAGAACACCGAGCGGACCACCGAGTTCTGGAAGCAGTACG

TGGACGGCGACCAGTGCGAGAGCAACCCCTGTCTGAATGGCGGCAGCTGC

AAGGACGACATCAACAGCTACGAGTGCTGGTGCCCCTTCGGCTTCGAGGG

CAAGAACTGCGAGCTGGACGTGACCTGCAACATCAAGAACGGCAGATGCG

AGCAGTTCTGCAAGAACAGCGCCGACAACAAGGTCGTGTGCTCCTGCACC

GAGGGCTACAGACTGGCCGAGAACCAGAAGTCCTGCGAGCCCGCCGTGCC

TTTCCCATGTGGAAGAGTGTCCGTGTCCCAGACCAGCAAGCTGACCAGAG

CCGAGACAGTGTTCCCCGACGTGGACTACGTGAACTCCACCGAGGCCGAG

ACAATCCTGGACAACATCACCCAGAGCACCCAGTCCTTCAACGACTTCAC

CAGAGTCGTGGGCGGCGAGGATGCCAAGCCTGGACAGTTCCCGTGGCAGG

TGGTGCTGAACGGAAAGGTGGACGCCTTTTGCGGCGGCAGCATCGTGAAC

GAGAAGTGGATCGTGACAGCCGCCCACTGCGTGGAAACCGGCGTGAAGAT

TACAGTGGTGGCCGGCGAGCACAACATCGAGGAAACCGAGCACACAGAGC

AGAAACGGAACGTGATCAGAATCATCCCCCACCACAACTACAACGCCGCC

ATCAACAAGTACAACCACGACATTGCCCTGCTGGAACTGGACGAGCCCCT

GGTGCTGAATAGCTACGTGACCCCCATCTGCATTGCCGACAAAGAGTACA

CCAACATCTTTCTGAAGTTCGGCAGCGGCTACGTGTCCGGCTGGGGCAGA

GTGTTTCACAAGGGCAGATCCGCTCTGGTGCTGCAGTACCTGAGAGTGCC

TCTGGTGGACCGGGCCACCTGTCTGAGAAGCACCAAGTTCACCATCTACA

ACAACATGTTCTGCGCCGGCTTCCATGAGGGCGGCAGAGATAGCTGTCAG

GGCGATTCTGGCGGCCCTCACGTGACAGAAGTGGAAGGCACCAGCTTTCT

GACCGGCATCATCAGCTGGGGCGAGGAATGCGCCATGAAGGGGAAGTACG

GCATCTACACCAAGGTGTCCAGATATGTGAACTGGATCAAAGAAAAGACC
```

-continued
```
AAGCTGACAGGCGGCGGAGGCTCTGGCGGAGGCGGATCTAGAACAGTGGC

CGCTCCCAGCGTGTTCATCTTCCCACCTAGCGACGAGCAGCTGAAGTCCG

GCACAGCCTCTGTCGTGTGCCTGCTGAACAACTTCTACCCCCGCGAGGCC

AAGGTGCAGTGGAAGGTGGACAATGCCCTGCAGAGCGGCAACAGCCAGGA

AAGCGTGACCGAGCAGGACAGCAAGGACTCCACCTACAGCCTGAGCAGCA

CCCTGACCCTGAGCAAGGCCGACTACGAGAAGCACAAGGTGTACGCCTGC

GAAGTGACCCACCAGGGCCTGTCTAGCCCAGTGACCAAGAGCTTCAACCG

GGGCGAATCTGGGGCGGAGGATCAGGCGGGGAGGAAGTGGGGGAGGGG

GAAGCGGAGGGGAGGATCTGCCTCTACAAAGGGCCCTAGCGTGTTCCCC

CTGGCCCCTAGCAGCAAGTCTACAAGCGGAGGCACAGCTGCCCTGGGCTG

CCTCGTGAAGGACTACTTCCCTGAGCCCGTGACCGTGTCCTGGAACAGCG

GAGCACTGACAAGCGGCGTGCACACCTTTCCAGCCGTGCTGCAGAGCAGC

GGCCTGTACTCTCTGAGCAGCGTCGTGACAGTGCCCAGCAGCTCTCTGGG

CACCCAGACCTACATCTGCAACGTGAACCACAAGCCCAGCAATACCAAAG

TGGACAAGCGGGTGGAACCCAAGAGCAGCGACAAGACCCACACCTGTCCC

CCTTGTCCTGCCCCCGAACTGCTGGGAGGCCCTTCCGTGTTCCTGTTCCC

CCCAAAGCCCAAGGACACCCTGATGATCAGCCGGACCCCTGAAGTGACCT

GCGTGGTGGTGGATGTGTCCCACGAGGACCCAGAAGTGAAGTTCAATTGG

TATGTGGACGGGGTGGAAGTGCACAACGCCAAGACCAAACCCAGAGAGGA

ACAGTACAATAGCACCTACCGGGTGGTGTCCGTGCTGACAGTGCTGCACC

AGGACTGGCTGAATGGCAAGGAGTATAAGTGCAAAGTGTCCAACAAGGCC

CTGCCTGCCCCCATCGAGAAAACCATCAGCAAGGCCAAGGGCCAGCCCCG

CGAACCCCAGGTGTACACACTGCCCCCAAGCCGGGAAGAGATGACCAAGA

ACCAGGTGTCCCTGACCTGTCTCGTGAAAGGCTTCTACCCTTCCGATATC

GCCGTGGAATGGGAGAGCAACGGCCAGCCCGAGAACAATTACAAGACCAC

CCCCCCTGTGCTGGACTCCGACGGCTCATTCTTCCTGTACAGCAAACTGA

CCGTGGACAAGAGCCGGTGGCAGCAGGGAAACGTGTTCAGCTGCAGCGTG

ATGCACGAGGCCCTGCACAACCACTACACCCAGAAAAGCCTGAGCCTGTC

CCCTGGCAAG;
``` was synthesized (Genewiz), cloned into pcDNA/UCOE and transiently expressed in HEK293 cells using the Expi293 expression system (Life Technologies). Proteins were purified first using Protein A (GE Healthcare) with low pH elution and dialyzed against 2 L 25 mM TRIS pH 7.5, 150 mM NaCl 3 times. Following dialysis, the protein was loaded onto a Q sepharose FF column and eluted with step gradients of CaCl$_2$ in 25 mM TRIS pH 7.5, 150 mM NaCl. The most active fractions were pooled and dialyzed against 1×PBS for further analysis.

Figure 2:
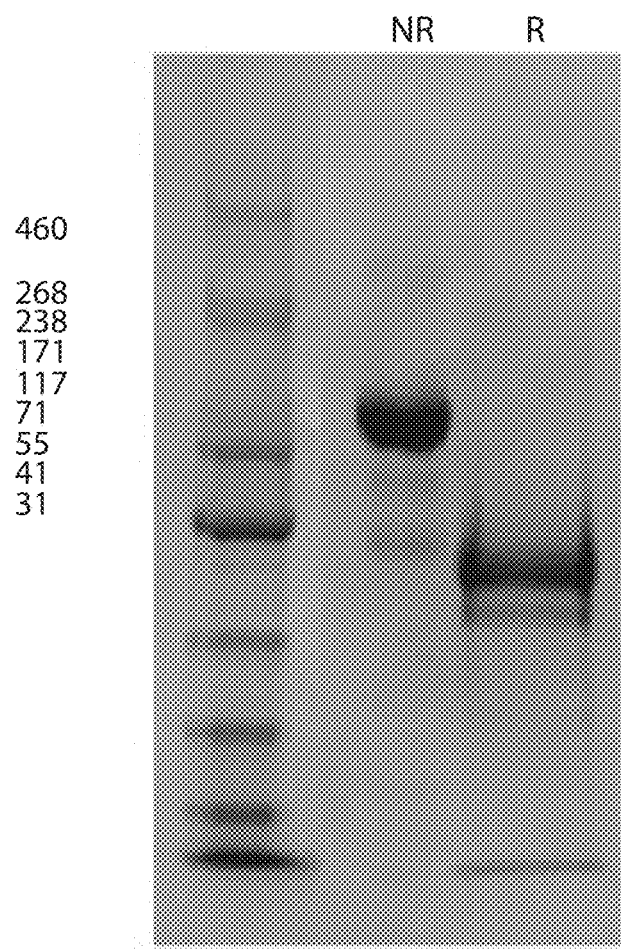
FIG. 2 is an SDS-PAGE showing expression of an Fc fusion protein comprising Factor IX fused to the Fc region of an IgG1 antibody via the novel scCLCH1 linker in accordance with the invention.

The molecule was analyzed by SDS PAGE gel under reducing and non-reducing conditions (FIG. 2). For non-reducing conditions, 5 ug of purified protein was loaded onto a NuPAGE® NOVEX® 3-8% TRIS-Acetate gel (Invitrogen) with a HIMARK™ pre-stained protein standard (Invitrogen) (MW range 31 kD-460 kD). For reducing conditions, 5 ug of protein was loaded onto an any kD™ gel (Invitrogen) with a PRECISION PLUS PROTEIN™ Kaleidoscope standard (Invitrogen) (MW range 10 kD-250 kD).

Bioactivity of Factor IX scC$_L$C$_H$1-Fc (APTT Assay)

Figure 3:
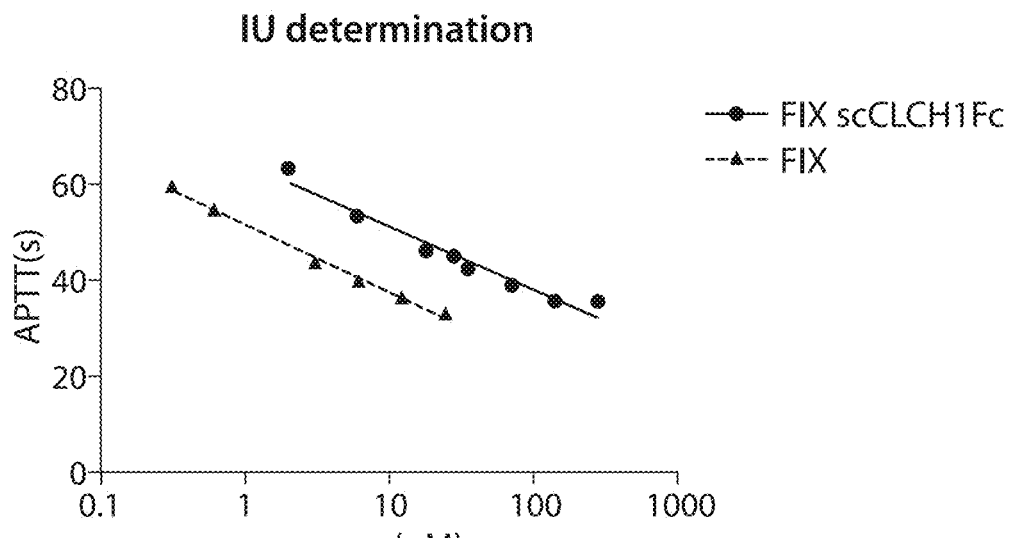
FIG. 3 is graph showing the clotting activity of an Fc fusion protein comprising Factor IX fused to the Fc region of an IgG1 antibody via the novel scCLCH1 linker in accordance with the invention.

An automated Factor IX activity assay was performed using the KC-1 Delta™ instrument (Tcoag, Wicklow, IRE) to quantify the ability of the FIX component of the Factor IX scC$_L$C$_H$1-Fc protein to restore the clotting activity of FIX-deficient plasma. Test samples were mixed with equal volumes of human FIX-deficient plasma (George King Bio-Medical Inc, Overland Park, Kans.) and cephalin-containing ellagic acid activator (aPTT-soluble activator, Helena Laboratories, cat. #5389), and after 4 min incubation, 5 mM calcium chloride (25 mM stock, VWR) was added and the time to clot measured. Activity was calculated based on a calibration curve of clotting times versus activity unit concentration (IU/mL) of serial dilutions of rHuman Factor IX (FIX) (Haematologic Technologies Inc. Essex Junction, Vt.) standard for purified proteins. Factors of intrinsic coagulation systems are activated by incubating the plasma with the optimal amount of phospholipids and a surface activator at 37° C. The addition of calcium ions triggers the coagulation process, and the clotting time is them measured. The APTT is the time taken for a fibrin clot to form (FIG. 3).

Rat PK of Factor IX scC$_L$C$_H$1-Fc

Figure 4:
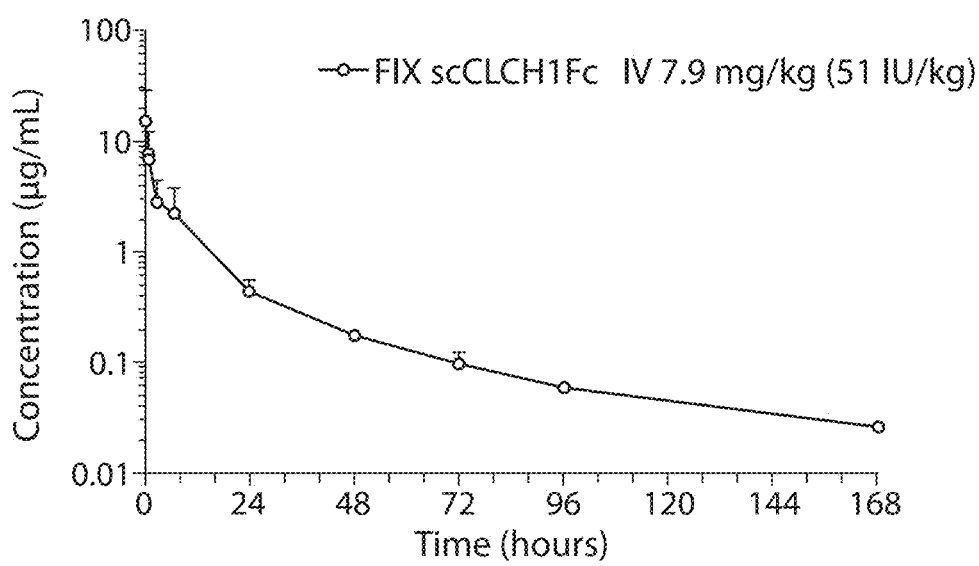
FIG. 4 is a graph showing the in vivo half-life in rats when intravenously administered an Fc fusion protein comprising Factor IX fused to the Fc region of an IgG1 antibody via the novel scCLCH1 linker.

Single intravenous doses of 51 IU/kg factor IX scC$_L$C$_H$1-Fc were administered into the lateral tail vein of 3 rats. Blood samples were collected at 0.25, 4, 8, 24, 48, 72, 96, and 168 hours after administration of factor IX scC$_L$C$_H$1-Fc, and citrated plasma (0.32% final) prepared. Concentrations were measured using standard MSD techniques with Goat anti-Human factor IX Affinity purified IgG (Enzyme Research Laboratories, South Bend, Ind.) as the capture antibody and Goat anti-Human IgG Fc cross-adsorbed antibody biotinylated (Bethyl Laboratories, Montgomery, Tex.) as the detection antibody. Pharmacokinetic analysis was performed using non-compartmental modeling with WIN-NONLIN® software (Pharsight Corporation, Mountain View, Calif.). The pharmacokinetic parameter estimates derived from MSD data included maximum concentration (Cmax), area under the time versus concentration curve (AUC), and elimination half-life (t$_{1/2}$) (FIG. 4 and Table 1).

```
CCGGAAGCACCTGCAGGCTCAGGGAGTACTACGATCAGACCGCCCAAATG
TGTTGCAGCAAGTGCTCCCCTGGCCAGCACGCCAAGGTGTTCTGCACCAA
GACAAGCGATACCGTGTGCGATAGCTGTGAGGACAGCACCTACACCCAGC
TGTGGAATTGGGTGCCCGAGTGCCTGAGCTGTGGCAGCAGGTGCAGCAGC
GATCAGGTGGAGACACAGGCCTGCACCAGAGAGCAGAACAGGATTTGTAC
CTGCAGGCCCGGCTGGTATTGCGCCCTGAGCAAGCAGGAGGGATGTAGGC
TGTGCGCCCCTCTGAGGAAATGCAGACCTGGCTTTGGAGTGGCTAGGCCC
GGCACCGAGACATCCGACGTGGTGTGCAAGCCTTGTGCCCCTGGCACCTT
TTCCAACACCACCAGCTCCACCGACATCTGCAGGCCCCATCAGATTTGCA
ACGTGGTGGCCATCCCCGGAAACGCTAGCATGGATGCCGTGTGCACCTCC
ACCTCCCCTACCAGGAGCATGGCCCCTGGAGCCGTGCATCTGCCTCAACC
CGTCAGCACCAGAAGCCAGCACACACAGCCCACCCCCGAACCTAGCACCG
CTCCCTCCACCAGCTTCCTGCTGCCTATGGGACCCTCCCCTCCTGCCGAA
GGGAGCACCGGAGATGGAGGAGGAGGAAGCGGCGGAGGAGGCTCCAGAAC
AGTGGCTGCCCCTAGCGTGTTCATTTTCCCTCCCTCCGACGAGCAGCTCA
AGTCCGGAACCGCTTCCGTGGTCTGCCTGCTGAACAACTTCTACCCCAGA
GAGGCCAAGGTGCAGTGGAAAGTCGACAATGCTCTGCAGAGCGGAAACTC
CCAGGAGTCCGTCACCGAGCAGGACAGCAAGGACTCCACATATAGCCTGT
CCTCCACCCTGACCCTGAGCAAGGCCGACTATGAGAAACACAAGGTGTAT
GCCTGCGAAGTGACCCACCAGGGCCTGTCCAGCCCCGTCACCAAGTCCTT
CAATAGGGGCGAGAGCGGAGGCGGCGGGAGCGGCGGCGGCGGGAGCGGAG
GAGGAGGGAGCGGAGGAGGCGGAAGCGCTTCCACCAAGGGACCTAGCGTG
TTTCCCCTCGCCCCAGCTCCAAGAGCACAAGCGGAGGCACAGCCGCTCT
```

TABLE 1

| Test Article | Testing Animal | Dosing Route | Dose (mg/kg) | Dose (IU/kg) | C$_{max}$ (ug/mL) | AUC$_{0-\infty}$ (ug-h/mL) | t$_{1/2}$ (h) |
|---|---|---|---|---|---|---|---|
| FIXscLCLCH1Fc | rat | IV | 7.9 | 51 | 17.0 ± 11.4 | 69.6 ± 7.78 | 53.7 ± 12.5 |
| Mono* FIXFc | rat | IV |  | 200 |  |  | 34.8 ± 5.3 |
| rhFIX** | rat | IV |  | 50 | 2.6 | 8.2 | 5.0 |

*Peters, R. T. et al. Prolonged activity of factor IX as a monomeric Fc fusion protein. Blood. (2013).
**Keith, J. C. et al. *Evaluation of Recombinant Human Factor IX: Pharmacokinetic Studies in the Rat and the Dog. Thrombosis and Haemostasis* 73(1): 101-105 (1994).

Example 2: TNF-R2

Design of TNF-R2 scC$_L$C$_H$1-Fc

The single chain TNFR2 molecule contains the TNFR2 sequence followed by a 10 residue linker, GGGGSGGGGS (SEQ ID NO: 11), the CL domain of IgG1 followed by a 20 residue linker GGGGSGGGGSGGGGSGGGGS (SEQ ID NO: 12) followed by the CH1, hinge and Fc portions of human IgG1.

Expression of TNF-R2 scC$_L$C$_H$1-Fc

The gene, having the following DNA sequence:

(SEQ ID NO: 14)
```
ATGTATAGGATGCAGCTCCTCAGCTGCATCGCTCTGTCCCTCGCCCTGGT
GACCAACAGCCTCCCTGCCCAGGTGGCCTTTACACCCTACGCTCCTGAGC
GGGCTGTCTGGTGAAGGATTACTTCCCCGAGCCCGTCACAGTGAGCTGGA
ACTCCGGAGCCCTGACCTCCGGAGTGCACACCTTTCCTGCCGTGCTGCAG
AGCAGCGGACTGTACAGCCTGTCCAGCGTGGTCACAGTGCCCTCCAGCTC
CCTGGGCACCCAGACCTACATCTGCAACGTGAACCACAAGCCCAGCAACA
CAAAGGTGGACAAGAGAGTGGAACCTAAGTCCTGTGACAAAACCCATACC
TGCCCTCCCTGCCCTGCCCCTGAGCTGCTGGGAGGACCTAGCGTGTTTCT
GTTTCCCCCCAAACCCAAGGATACCCTGATGATCAGCAGGACCCCTGAGG
TGACATGCGTGGTGGTGGACGTGTCCCACGAGGACCCTCAGGTCAAGTTC
```

-continued
```
AACTGGTACGTGGATGGCGTCCAGGTGCACAATGCTAAGACCAAGCCCAG

GGAGCAGCAATACAATTCCACCTACAGGGTGGTGTCCGTGCTCACCGTCC

TCCACCAGAACTGGCTCGACGGCAAAGAATACAAGTGCAAAGTGAGCAAC

AAGGCTCTCCCCGCCCCTATCGAGAAGACCATTTCCAAAGCCAAGGGCCA

GCCCAGAGAACCTCAAGTCTACACCCTGCCCCCCAGCAGGGAGGAGATGA

CCAAGAACCAGGTGAGCCTGACCTGCCTCGTCAAGGGATTCTATCCCAGC

GACATCGCCGTGGAATGGGAGTCCAATGGCCAGCCCGAGAATAACTACAA

GACCACACCCCCCGTGCTGGATTCCGATGGCAGCTTTTTCCTGTACAGCA

AGCTGACAGTGGATAAGAGCAGGTGGCAGCAGGGCAACGTGTTCAGCTGC

TCCGTCATGCACGAAGCCCTGCACAATCACTACACCCAGAAGAGCCTGTC

CCTCAGCCCCGGCAAG;
``` was synthesized (Genewiz), cloned into pcDNA/UCOE and transiently expressed in HEK293 cells using the Expi293 expression system (Life Technologies). Proteins were purified first using Protein A (GE Healthcare) with low pH elution and dialyzed against 2 L 1×PBS 3 times.

Figure 5A:
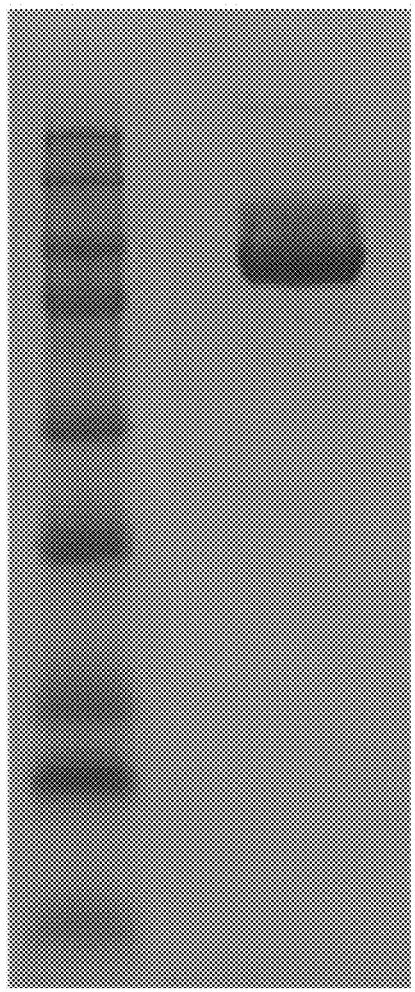
FIG. 5A is an SDS-PAGE showing expression of an Fc fusion protein comprising TNFR2 fused to the Fc region of an IgG1 antibody via the novel scCLCH1 linker under reducing conditions.
Figure 5B:
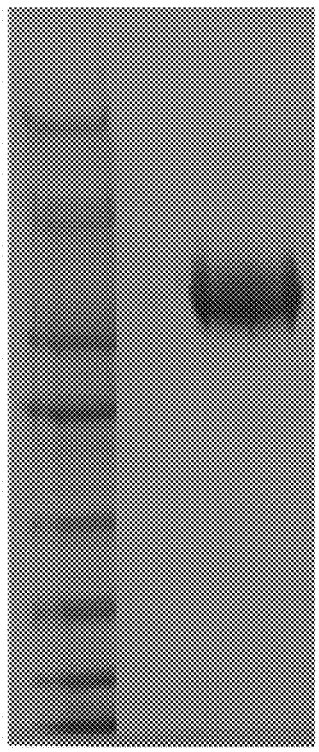
FIG. 5B is an SDS-PAGE showing expression of an Fc fusion protein comprising TNFR2 fused to the Fc region of an IgG1 antibody via the novel scCLCH1 linker under non-reducing conditions.

The molecule was analyzed by SDS PAGE gel under reducing and non-reducing conditions (FIGS. 5A and 5B). For non-reducing conditions, 5 ug of purified protein was loaded onto a NuPAGE® Novex® 3-8% TRIS-Acetate gel (Invitrogen) with a HiMark™ Pre-stained protein standard (Invitrogen) (MW range 31 kD-460 kD). For reducing conditions, 5 ug of protein was loaded onto Any kD™ gel (Invitrogen) with a PRECISION PLUS PROTEIN™ Kaleidoscope standard (Invitrogen) (MW range 10 kD-250 kD).

Bioactivity of TNF-R2 $scC_LC_H1$-Fc

Figure 6:
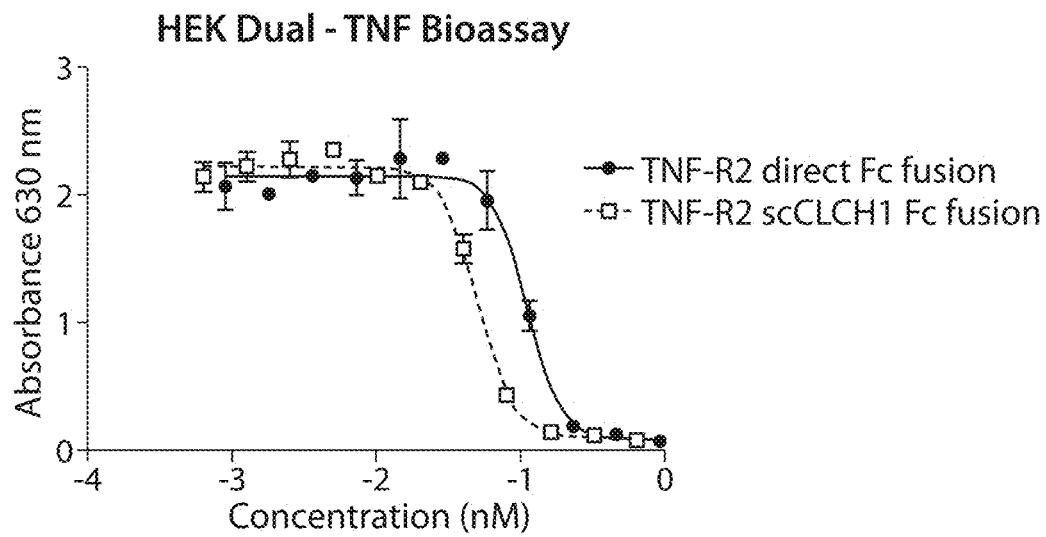
FIG. 6 is a graph showing the inhibition of the activation of a reporter gene by the TNFR2 fusion protein of the invention as compared to a standard TNF direct fusion protein.

HEK-Blue™ TNF-α cells (InvivoGen) are human embryonic kidney cells specifically designed to detect bioactive TNF-α in vitro by monitoring the activation of the NF-κB/AP-1 pathways. The cell line expresses an inducible secreted embryonic alkaline phosphatase (SEAP) reporter gene under control of the IFN-β minimal promoter fused to five NFκb and five AP-1 binding sites. For the TNF-α antagonist assay, HEK-Blue TNF-α cells were plated at 50,000 cells/well in DMEM media containing 2 mM L-glutamine, 4.5 g/l glucose and 10% heat inactivated FBS (Gibco) and 235 pM TNF-α 1a (InvivoGen). Cells were incubated for 20 hours at 37° C., 5% $CO_2$ with varying concentrations of TNF-R2 direct fusion or TNF-R2 single chain fusion body (TNF-R2 $scC_LC_H1$-Fc). SEAP production was detected by adding QUANTI-Blue and incubating for 3 hours at 37° C., 5% $CO_2$ and read on a plate reader at 630 nm. Activation of the SEAP gene can be inhibited by the TNF-α antagonist TNF-R2 in a dose dependent manner. The TNF-R2 single chain fusion body molecule inhibited activation of the SEAP gene with an $IC_{50}$ of 51 pM vs the direct fusion of TNF-R2 with an $IC_{50}$ of 112 pM (FIG. 6).

Rat PK of TNF-R2 $scC_LC_H1$-Fc

Figure 7:
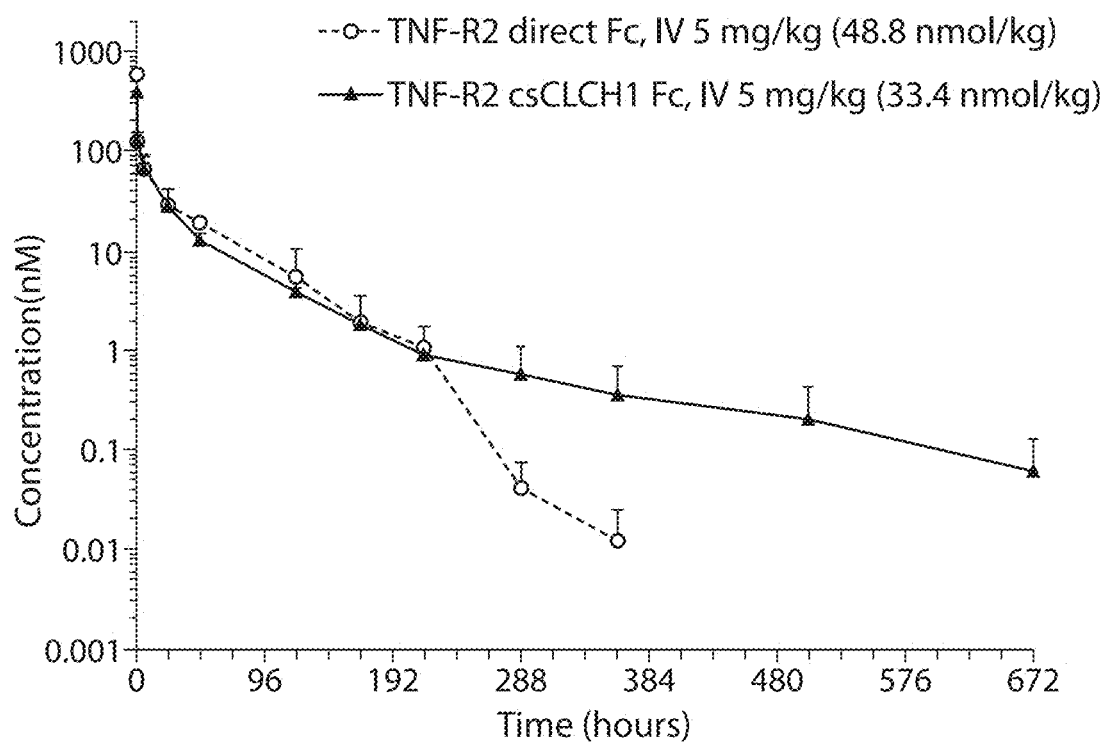
FIG. 7 is a graph showing the in vivo half-life in rats when intravenously administered an Fc fusion protein comprising TNFR2 fused to the Fc region of an IgG1 antibody via the novel scCLCH1 linker as compared to a standard TNF direct fusion protein.

Single intravenous doses of 5 mg/kg TNF-R2 $scC_LC_H1$-Fc were administered into the lateral tail vein of 3 rats. Blood samples were collected at 0.083, 1, 6, 24, 48 hr, 5, 7, 9, 12, 15, 21, 28 days after administration of TNF-R2 $scC_LC_H1$-Fc. Concentrations were measured using standard MSD techniques with Goat anti-Human F(ab')2 IgG Fc (Thermo Scientific, Rockford, Ill.) as the capture antibody and Goat anti-Human IgG Fc cross-adsorbed antibody biotinylated (Bethyl Laboratories, Montgomery, Tex.) as the detection antibody. Pharmacokinetic analysis was performed using non-compartmental modeling with WinNonlin® software (Pharsight Corporation, Mountain View, Calif.). The pharmacokinetic parameter estimates derived from MSD data included maximum concentration (Cmax), area under the time versus concentration curve (AUC), and elimination half-life ($t_{1/2}$) (FIG. 7 and Table 2).

TABLE 2

| Test Article | Testing Animal | Dosing Route | Dose (mg/kg) | $C_{max}$ (nM) | $AUC_{0-\infty}$ (nM-h) | $t_{1/2}$ (h) |
|---|---|---|---|---|---|---|
| TNF-R2 direct fusion | rat | IV | 5 | 584 ± 59.2 | 3445 ± 967 | 24 ± 6.5 |
| TNF-R2 $scC_LC_H1$-Fc | rat | IV | 5 | 412 ± 109 | 3207 ± 157 | 102 ± 33 |

Example 3: IL1Ra

Design of IL1Ra $scC_LC_H1$-Fc

The single chain IL1Ra molecule contains the IL1Ra sequence followed by a 10 residue linker, GGGGSGGGGS (SEQ ID NO: 11), the CL domain of IgG1 followed by a 20 residue linker, GGGGSGGGGSGGGGSGGGGS (SEQ ID NO: 12) followed by the CH1, hinge and Fc portions of human IgG1.

Expression of IL1Ra $scC_LC_H1$-Fc

The gene having the following DNA sequence:

```
                                         (SEQ ID NO: 15)
ATGTACCGGATGCAGCTGCTGTCCTGTATCGCCCTGTCTCTGGCCCTGGT

CACCAACTCCAGACCCTCTGGCCGGAAGTCCTCCAAGATGCAGGCCTTCC

GGATCTGGGACGTGAACCAGAAAACCTTCTACCTGCGGAACAACCAGCTG

GTGGCCGGCTATCTGCAGGGCCCCAACGTGAACCTGGAAGAGAAGATCGA

CGTGGTGCCCATCGAGCCCCACGCCCTGTTTCTGGGAATCCACGGCGGCA

AGATGTGCCTGTCCTGCGTGAAGTCCGGCGACGAGACACGGCTGCAGCTG

GAAGCCGTGAACATCACCGACCTGTCCGAGAACCGGAAGCAGGACAAGAG

ATTCGCCTTCATCAGATCCGACTCCGGCCCTACCACCTCCTTCGAGTCTG

CTGCTTGCCCCGGCTGGTTCCTGTGCACCGCCATGGAAGCTGACCAGCCC

GTGTCCCTGACCAACATGCCTGACGAGGGCGTGATGGTCACCAAGTTCTA

TTTTCAGGAAGATGAGGGCGGAGGCGGCTCTGGCGGCGGAGGATCTAGAA

CAGTGGCCGCTCCCTCCGTGTTCATCTTCCCACCTTCCGACGAGCAGCTG

AAGTCTGGCACCGCCTCTGTCGTGTGCCTGCTGAACAACTTCTACCCTCG

CGAGGCCAAGGTGCAGTGGAAGGTGGACAACGCCCTGCAGTCCGGCAACT

CCCAGGAATCCGTCACCGAGCAGGACTCCAAGGACAGCACCTACTCCCTG
```

-continued
```
TCCTCCACCCTGACCCTGTCCAAGGCCGACTACGAGAAGCACAAGGTGTA

CGCCTGCGAAGTGACCCACCAGGGCCTGTCTAGCCCCGTGACCAAGTCTT

TCAACCGGGGCGAAAGCGGAGGCGGAGGTTCAGGTGGTGGTGGATCAGGT

GGCGGCGGATCTGGCGGTGGTGGCTCTGCTTCTACCAAGGGCCCTTCCGT

GTTCCCTCTGGCCCCTTCCAGCAAGTCTACCTCTGGCGGCACAGCCGCTC

TGGGCTGCCTGGTCAAGGACTACTTCCCCGAGCCTGTGACCGTGTCCTGG

AACTCTGGCGCTCTGACATCCGGCGTGCACACCTTCCCTGCTGTGCTGCA

GTCCTCCGGCCTGTACAGCCTGTCCTCCGTCGTGACCGTGCCTTCCAGCT

CTCTGGGCACCCAGACCTACATCTGTAACGTGAACCACAAGCCCTCCAAC

ACCAAAGTGGACAAGCGGGTGGAACCCAAGTCCTCCGACAAGACCCACAC

CTGTCCTCCCTGCCCTGCTCCTGAACTGCTGGGCGGACCTAGCGTGTTCC

TGTTCCCTCCAAAGCCCAAGGACACCCTGATGATCTCCCGGACCCCTGAA

GTGACCTGCGTGGTGGTCGATGTGTCCCACGAGGACCCAGAAGTGAAGTT

CAATTGGTACGTGGACGGCGTGGAAGTGCACAATGCCAAGACCAAGCCCA

GAGAGGAACAGTACAACTCCACCTACCGGGTGGTGTCCGTGCTGACCGTG

CTGCACCAGGATTGGCTGAACGGCAAAGAGTACAAGTGCAAGGTGTCCAA

CAAGGCCCTGCCTGCCCCTATCGAAAAGACCATCTCCAAGGCCAAGGGCC

AGCCCCGGGAACCTCAGGTGTACACCCTGCCTCCCAGCCGGGAAGAGATG

ACCAAGAACCAGGTGTCACTGACCTGTCTGGTCAAGGGCTTCTACCCCTC

CGACATTGCCGTGGAATGGGAGTCCAACGGCCAGCCCGAGAACAACTACA

AGACCACCCCTCCCGTGCTGGACTCCGACGGCTCATTCTTCCTGTACTCC

AAGCTGACCGTGGACAAGTCCCGGTGGCAGCAGGGCAACGTGTTCTCCTG

CTCCGTGATGCACGAGGCCCTGCACAACCACTACACCCAGAAGTCCCTGT

Figure 8A:
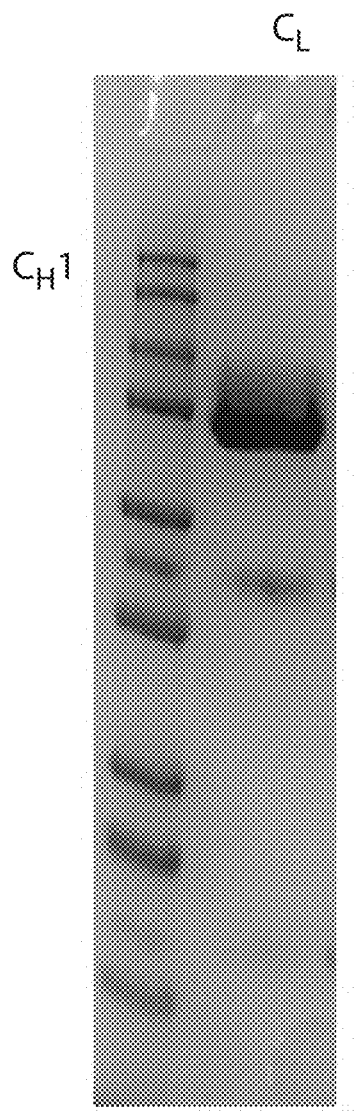
FIG. 8A is an SDS-PAGE showing expression of an Fc fusion protein comprising IL1Ra fused to the Fc region of an IgG1 antibody via the novel scCLCH1 linker under reducing conditions.
Figure 8B:
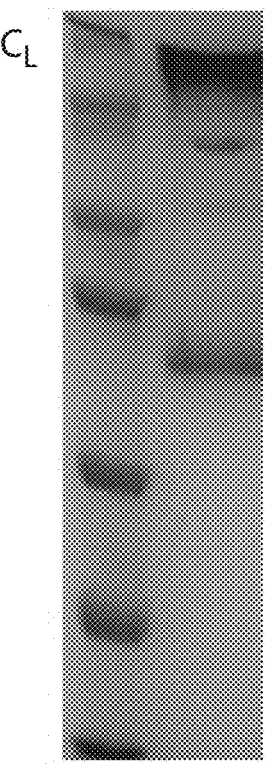
FIG. 8B is an SDS-PAGE showing expression of an Fc fusion protein comprising IL1Ra fused to the Fc region of an IgG1 antibody via the novel scCLCH1 linker under non-reducing conditions.

CCCTGAGCCCCGGCAAG;
``` was synthesized (Genewiz, Inc.), cloned into pcDNA/UCOE and transiently expressed in HEK293 cells using the Expi293 expression system (Life Technologies). Proteins were purified first using Protein A (GE Healthcare) with low pH elution and dialyzed against 2 L 1×PBS 3 times. The molecule was analyzed by SDS PAGE gel under reducing and non-reducing conditions (FIGS. 8A and 8B). For non-reducing conditions, 5 ug of purified protein was loaded onto a NuPAGE® NOVEX® 3-8% TRIS-Acetate gel (Invitrogen) with a HIMARK™ Pre-stained protein standard (Invitrogen) (MW range 31 kD-460 kD). For reducing conditions, 5 ug of protein was loaded onto an Any kD™ gel (Invitrogen) with a PRECISION PLUS PROTEIN™ Kaleidoscope standard (Invitrogen) (MW range 10 kD-250 kD).

Bioactivity of IL1Ra scC$_L$C$_H$1-Fc

Figure 9:
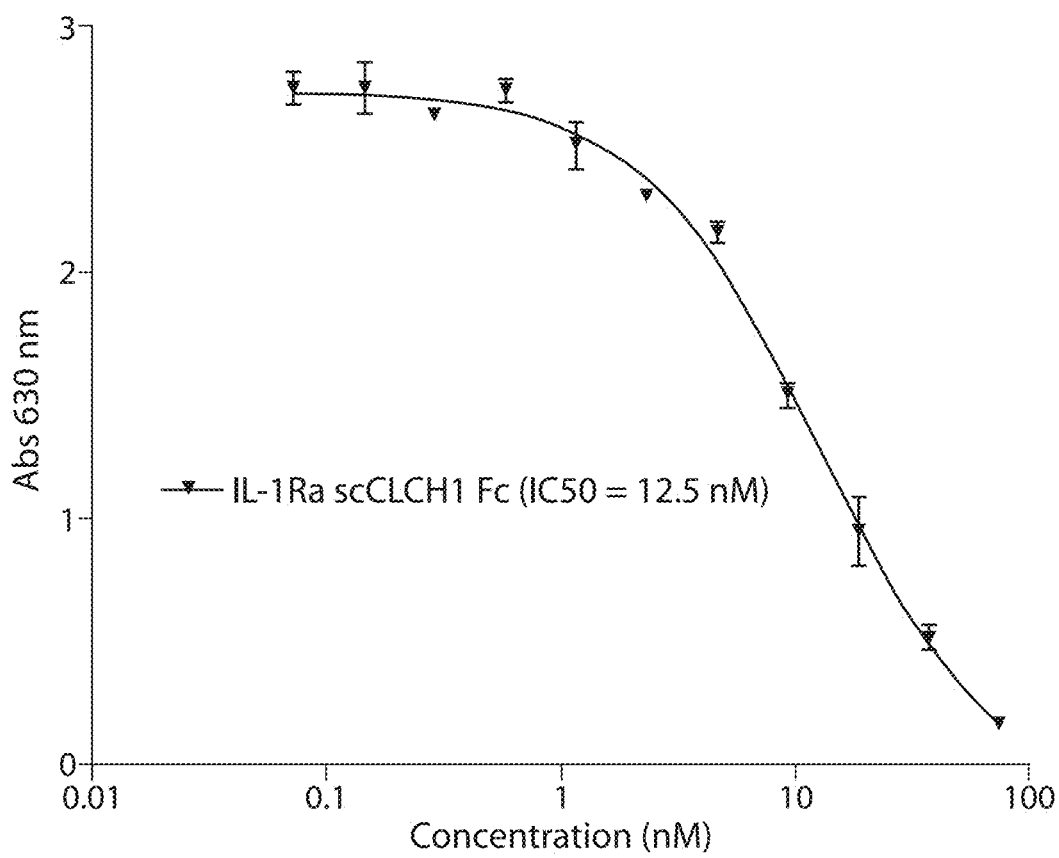
FIG. 9 is a graph showing the inhibition of the activation of a reporter gene by the IL1Ra fusion protein of the invention.

HEK-Blue™ IL-1β cells (InvivoGen) are human embryonic kidney cells specifically designed to detect bioactive IL-1β in vitro by monitoring the IL-1β-induced activation of the NF-κB/AP-1 pathways. The cell line expresses an inducible secreted embryonic alkaline phosphatase (SEAP) reporter gene under control of the IFN-β minimal promoter fused to five NFκb and five AP-1 binding sites. For the IL-1β antagonist assay, HEK-Blue IL-1β cells were plated at 50,000 cells/well in DMEM media containing 2 mM L-glu and 10% heat inactivated FBS (Gibco) and 57 pM IL-1β (R&D systems). Cells were incubated for 20 hours at 37° C., 5% $CO_2$ with varying concentrations of IL1RascC$_L$C$_H$1-Fc. SEAP production was detected by adding QUANTI-Blue and incubating for 3 hours at 37° C., 5% $CO_2$ and read on a plate reader at 630 nm. IL-1β activation of the SEAP gene can be inhibited by the IL-1β antagonist IL-1Ra in a dose dependent manner. The IL-1Ra single chain molecule inhibited IL-1β activation of the SEAP gene with an $IC_{50}$ of 12.5 Nm (FIG. 9).

Rat PK of IL1Ra scC$_L$C$_H$1-Fc

Figure 10:
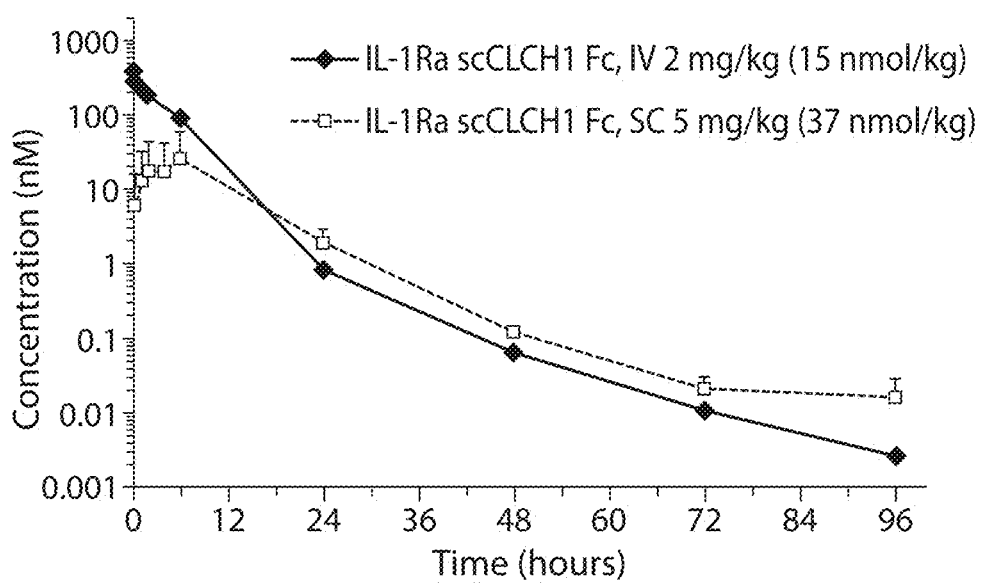
FIG. 10 is a graph showing the in vivo half-life in rats when intravenously administered an Fc fusion protein comprising IL1Ra fused to the Fc region of an IgG1 antibody via the novel scCLCH1 linker.

Single intravenous doses of 2 mg/kg IL1Ra scC$_L$CH$_1$-Fc were administered into a jugular vein catheter of 3 rats. Blood samples were collected at 0.083, 0.25, 1, 2, 6, 24, 48, 72, 96 and 168 hours after administration of IL1Ra scC$_L$C$_H$1-Fc. Single subcutaneous doses of 5 mg/kg IL1Ra scC$_L$C$_H$1-Fc were administered into the interscapular region of 3 rats. Blood samples were collected at 0.25, 1, 2, 4, 6, 24, 48, 72, 96 and 168 hours after administration of IL1Ra scC$_L$C$_H$1-Fc. Concentrations were measured using standard MSD techniques with Goat anti-Human F(ab')2 IgG Fc (Thermo Scientific, Rockford, Ill.) as the capture antibody and Mouse anti-Human IL1Ra biotin conjugate (Invitrogen, Grand Island, N.Y.) as the detection antibody. Pharmacokinetic analysis was performed using non-compartmental modeling with WINNONLIN® software (Pharsight Corporation, Mountain View, Calif.). The pharmacokinetic parameter estimates derived from MSD data included maximum concentration (Cmax), area under the time versus concentration curve (AUC), and elimination half-life ($t_{1/2}$) (FIG. 10 and Table 3).

TABLE 3

| Test Article | Testing Animal | Dosing Route | Dose (mg/kg) | $C_{max}$ (nM) | $AUC_{0-\infty}$ (nM-h) | $t_{1/2}$ (h) |
| --- | --- | --- | --- | --- | --- | --- |
| IL1Ra-scC$_L$C$_H$1-Fc | rat | IV | 2 | 375 ± 7.6 | 1828 ± 139 | 9.8 ± 0.9 |
| IL1Ra-scC$_L$C$_H$1-Fc | rat | SC | 5 | 24.7 ± 34.1 | 363 ± 476 | 9.4 ± 1.6 |
| rhIL-1Ra* | rat | IV | 1 | 448.5 ± 134 | 98.5 ± 5.8 | 1.15 ± 0.5 |
| rhIL-1Ra* | rat | SC | 1 | 25.3 ± 3.5 | 74.1 ± 9.3 | 0.85 ± 0.08 |

Figure 11:
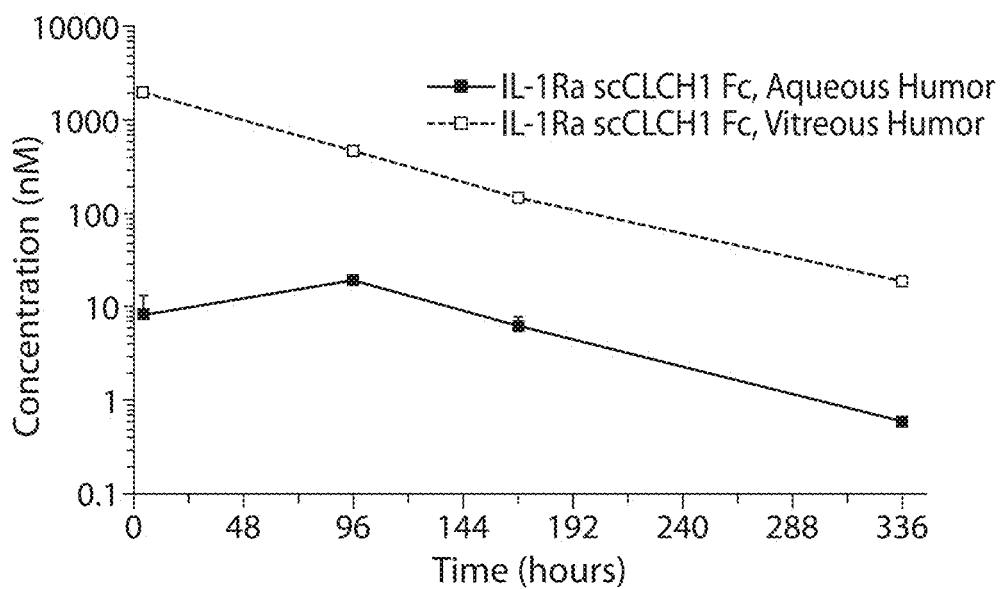
FIG. 11 is a graph showing the in vivo half-life in rats when intraocularly administered an Fc fusion protein comprising IL1Ra fused to the Fc region of an IgG1 antibody via the novel scCLCH1 linker.

*Source: FDA document BLA: 103950/0. PK parameters were converted to nM concentrations using a MW of 17257.6 g/mole for rhIL-1Ra Intra-Ocular PK of IL1Ra scC$_L$C$_H$1-Fc A bolus intravitreal injection of 0.5 mg IL1Ra scC$_L$C$_H$1-Fc was administered into each eye of 8 male rabbits. Blood samples from two animals were collected at 4, 96, 168 and 336 hours after administration of IL1Ra scC$_L$C$_H$1-Fc. At the time of sacrifice, both eyes from each animal were collected and flash frozen in liquid nitrogen. Concentrations were measured using standard MSD techniques. Pharmacokinetic analysis was performed using non-compartmental modeling with WINNONLIN® software (Pharsight Corporation, Mountain View, Calif.). The pharmacokinetic parameter estimates derived from MSD data included maximum concentration (Cmax), area under the time versus concentration curve (AUC), and elimination half-life ($t_{1/2}$) (Table 4 and FIG. 11).

TABLE 4

| Test Article | Testing Animal | Matrix | $C_{max}$ (ug/mL) | $AUC_{0-\infty}$ (ug/mL·h) | $t_{1/2}$ (h) |
|---|---|---|---|---|---|
| IL1Ra scC$_L$C$_H$1-Fc | rabbit | Aqueous | 2.53 | 369 | 83 |
| IL1Ra scC$_L$C$_H$1-Fc | rabbit | Vitreous | 265 | 2904 | 129 |

Example 4: IL-2/IL2Ra

Design of IL-2/IL-2Rα scC$_L$C$_H$1-Fc and IL-2/IL-2Rα scC$_{H1}$C$_L$-Fc

Figure 12A:
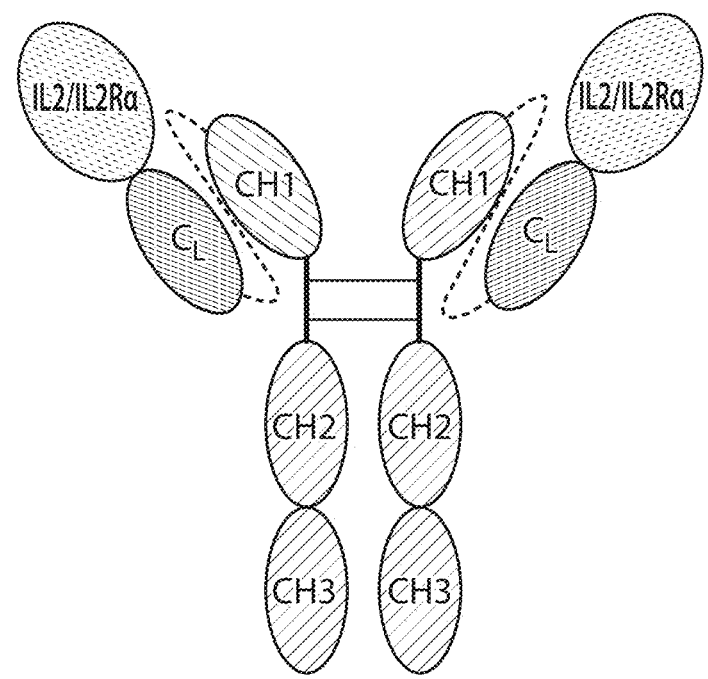
FIG. 12A is a diagram of an Fc fusion protein homodimer of two polypeptide chains, wherein in each polypeptide chain comprises as X, a fusion of IL-2/IL-2Rα which is then fused to the Fc region of an IgG1 antibody via the novel scCLCH1linker.
Figure 12B:
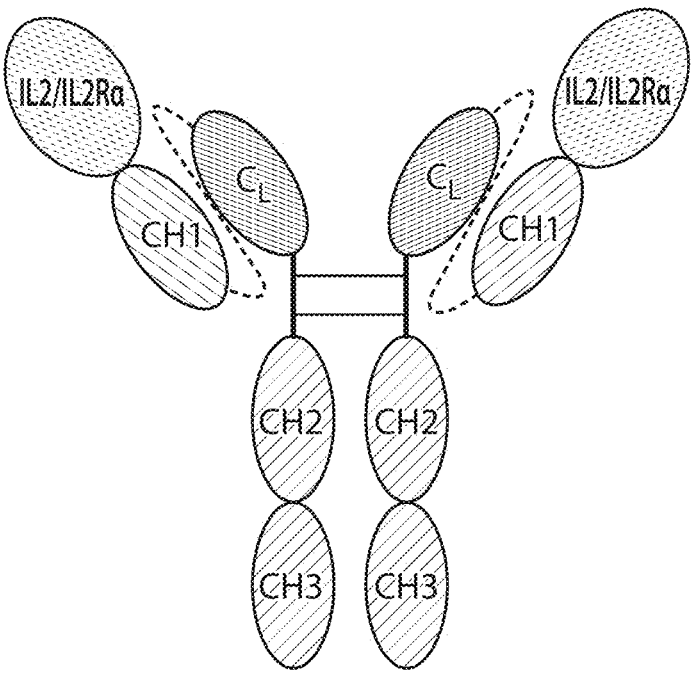
FIG. 12B is a diagram of an Fc fusion protein homodimer of two polypeptide chains, wherein in each polypeptide chain comprises as X, a fusion of IL-2/IL-2Rα which is then fused to the Fc region of an IgG1 antibody via the novel scCH1CLlinker.

The IL-2/IL-2Rα single chain fusion body molecule contains a circularly permuted human IL-2 linked to the extracellular domain of IL-2Rα fusion protein linked to the CL-CH1-Fc domain (SEQ ID NO: 19) or the CH1-CL-Fc (SEQ ID NO: 20) of the IgG1 heavy chain (FIGS. 12A and 12B) referred to herein as IL-2/IL-2Rα scC$_L$C$_H$1-Fc and IL-2/IL-2Rα scC$_H$1C$_L$-Fc, respectively. For expression in mammalian cells, the N-terminal leader sequence of SEQ ID NO: 10 was added to the protein of SEQ ID NO: 19 and SEQ ID NO: 20).

Expression of IL-2/IL-2Rα scC$_L$C$_H$1-Fc and IL-2/IL-2Rα scC$_{H1}$C$_L$-Fc

The genes were synthetically synthesized and supplied in pcDNA3.1 expression vector (GeneArt), and transiently expressed in HEK293 cells using the Expi293 expression system (Life Technologies). Proteins were purified using Protein A (GE Healthcare) with low pH elution and dialyzed against 2 L 1×PBS 2 times.

Figure 13:
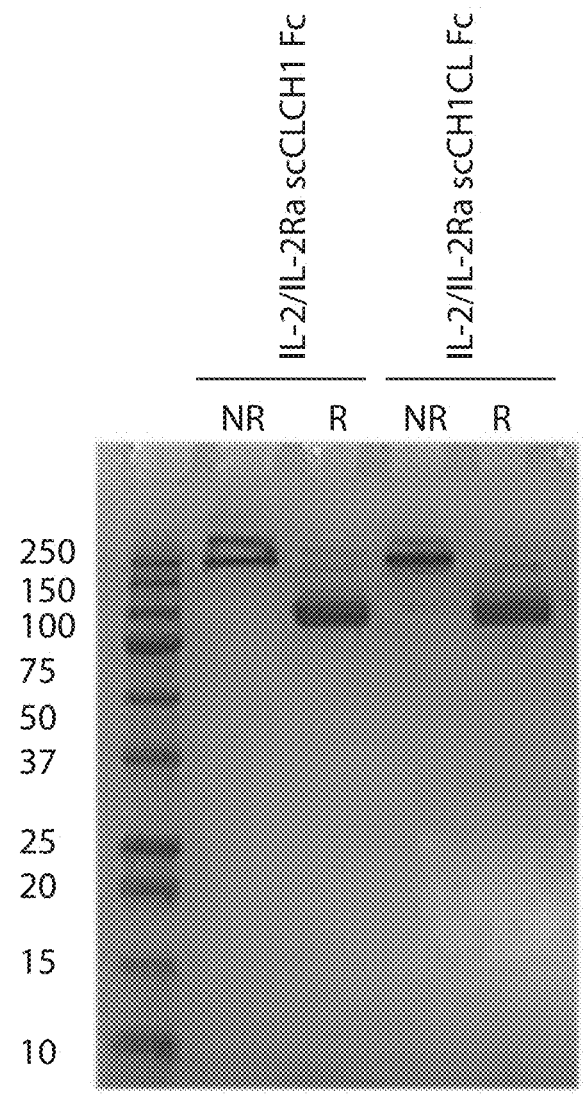
FIG. 13 is an SDS-PAGE showing expression of an Fc fusion protein comprising IL-2/IL-2Rα fused to the Fc region of an IgG1 antibody via the novel scCLCH1 linker (left) or via the novel scCH1CL linker (right) under reducing and non-reducing conditions.
Figure 14A:
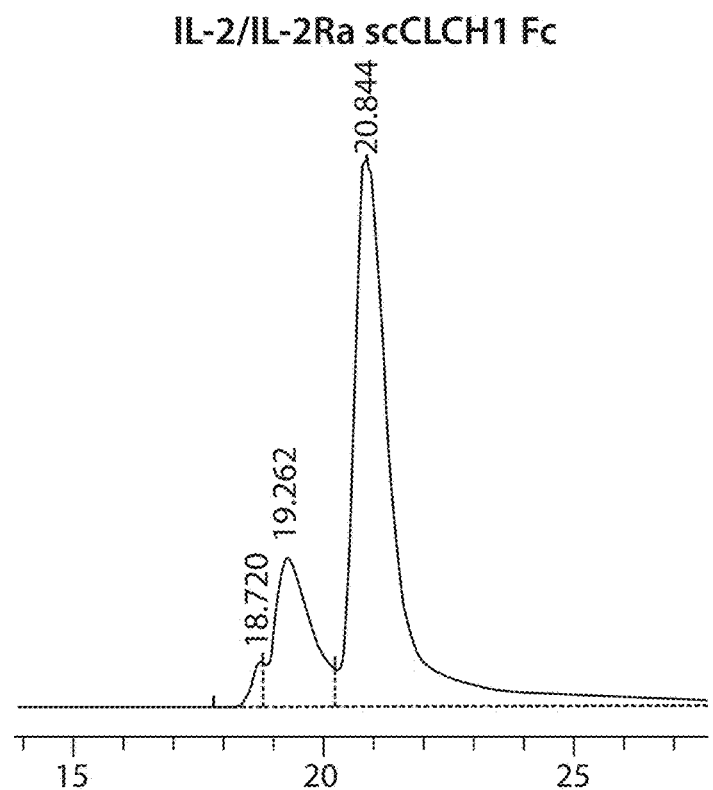
FIG. 14A is a chromatogram showing the characterization of the IL-2/IL-2Rα fused to the Fc region of an IgG1 antibody via the novel scCLCH1 linker by analytical gel filtration.
Figure 14B:
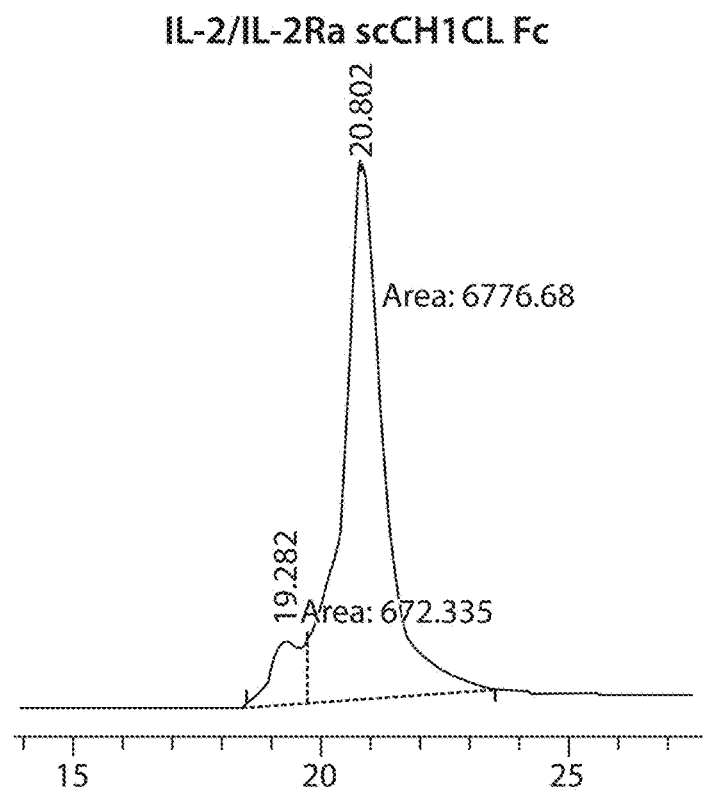
FIG. 14B is a chromatogram showing the characterization of the IL-2/IL-2Rα fused to the Fc region of an IgG1 antibody via the novel scCH1CL linker by analytical gel filtration.
Figure 15:
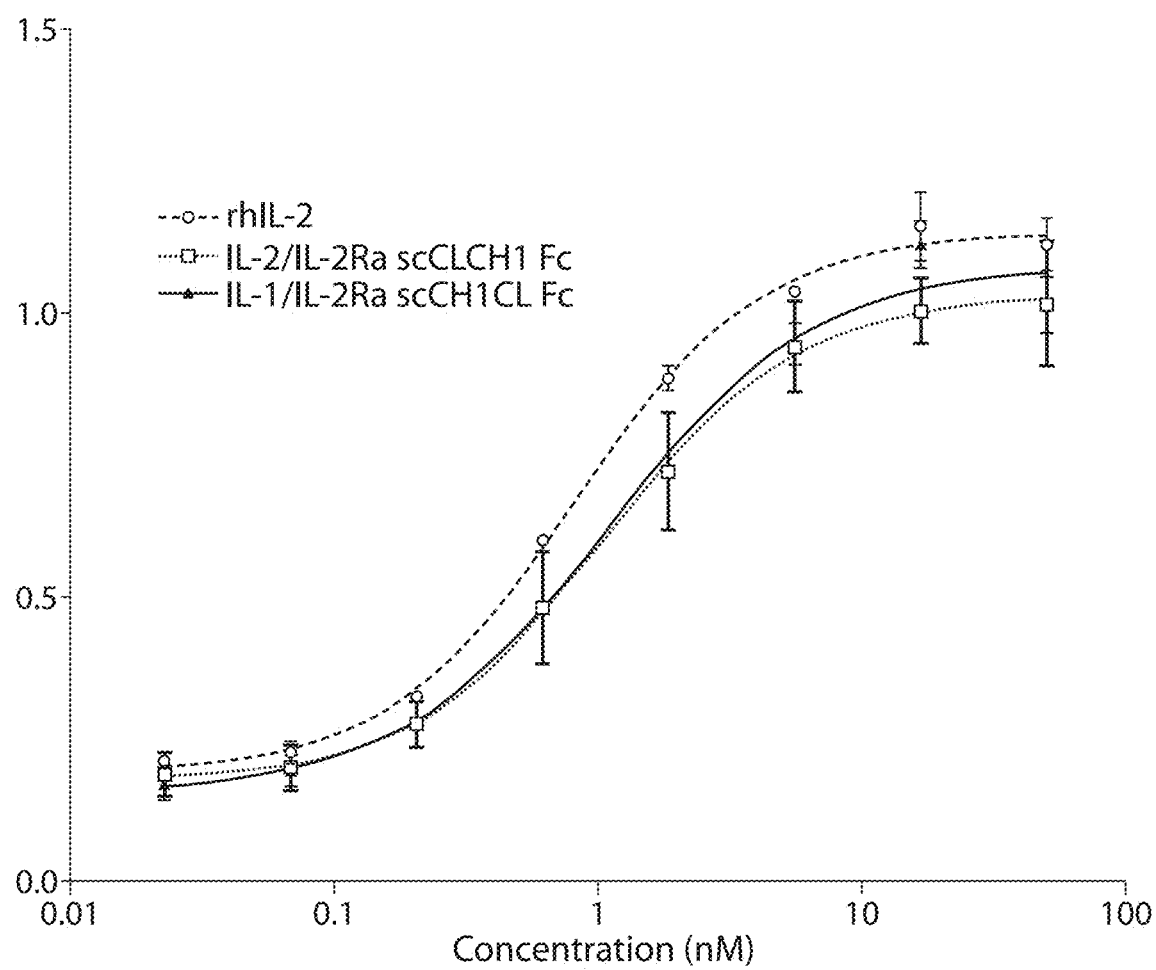
FIG. 15 is a graph showing activation of pSTAT5 by the IL-2/IL-2Rα single chain fusion proteins of the invention as compared to rhIL-2.

The molecules were analyzed by SDS PAGE gel under reducing and non-reducing conditions (FIG. 13). For reducing and non-reducing conditions, 5 ug of protein was loaded onto an Any kD gel (Invitrogen) with a Precision Plus Protein Kaleidoscope standard (Invitrogen) (MW range 10 kD-250 kD). The molecule was characterized by analytical gel filtration on a BioSuite Ultra High Resolution SEC column, 250 Å, 4 μm, 4.6 mm×300 mm (Waters). The column was equilibrated and run at 0.3 ml/min with 150 mM sodium phosphate pH 7.0 as a running buffer for all analyses. Purified samples (0.5 mg/ml) were injected (15 ul) and eluted with a run time of 25 min (FIGS. 14A and 14B). Bioactivity of IL-2/IL-2Rα scC$_L$C$_H$1-Fc and IL-2/IL-2Rα scC$_{H1}$C$_L$-Fc In vitro bioactivity was assessed by evaluating the ability of IL-2/IL-2Rα scC$_L$C$_H$1-Fc and IL-2/IL-2Rα scC$_{H1}$C$_L$-Fc to activate pSTAT5 in the human HH T-cell lymphoma cell line (ATCC CRL-2105) using the Phospho-STAT5A/B (Tyr694/Tyr699) InstantOne™ ELISA kit from eBioscience. For the assay, HH cells were plated at 2×10$^5$ cells/well in RPMI1640 media containing 10% FBS. Samples were incubated with decreasing concentrations of wild-type IL-2 (wtIL-2), IL-2/IL-2Ra scClCH1 Fc or IL-2/IL-2Ra scCH2Cl Fc from approximately 50 nM, or unstimulated, for approximately 25±5 minutes in a 37° C., 5% CO$_2$ incubator. Stimulation reaction was terminated by prompt addition of 25 μL of cell lysis mix (provided in kit) and incubated at room temperature for 10 minutes with constant shaking at 300 rpm on a titer plate shaker. 50 μL aliquots of resulting lysates were added to each well in the assay plate (provided in kit). After adding 50 μL of antibody cocktail to each well, the plate was covered and incubated at room temperature for 1 hour with constant shaking at 300 rpm on a titer plate shaker. Plate was subsequently washed three times with 300 μL/well of 1× wash buffer. 100 μL of detection reagent was added to each well and incubated at room temperature for 30 minutes with constant shaking at 300 rpm. Detection reaction was stopped by addition of 100 μL of stop solution and the absorbance at 450 nM was measured using a SynergyMx plate reader. IL-2/IL-2Ra scClCH1 Fc (EC$_{50}$=0.97 nM), or IL-2/IL-2Ra scCH2Cl Fc (EC$_{50}$=1.1 nM) and wtIL-2 (EC$_{50}$=0.80 nM) were active in a dose dependent fashion (FIG. 15).

Rat PK of IL-2/IL-2Rα scC$_L$C$_H$1-Fc and IL-2/IL-2Rα scC$_{H1}$C$_L$-Fc

Figure 16:
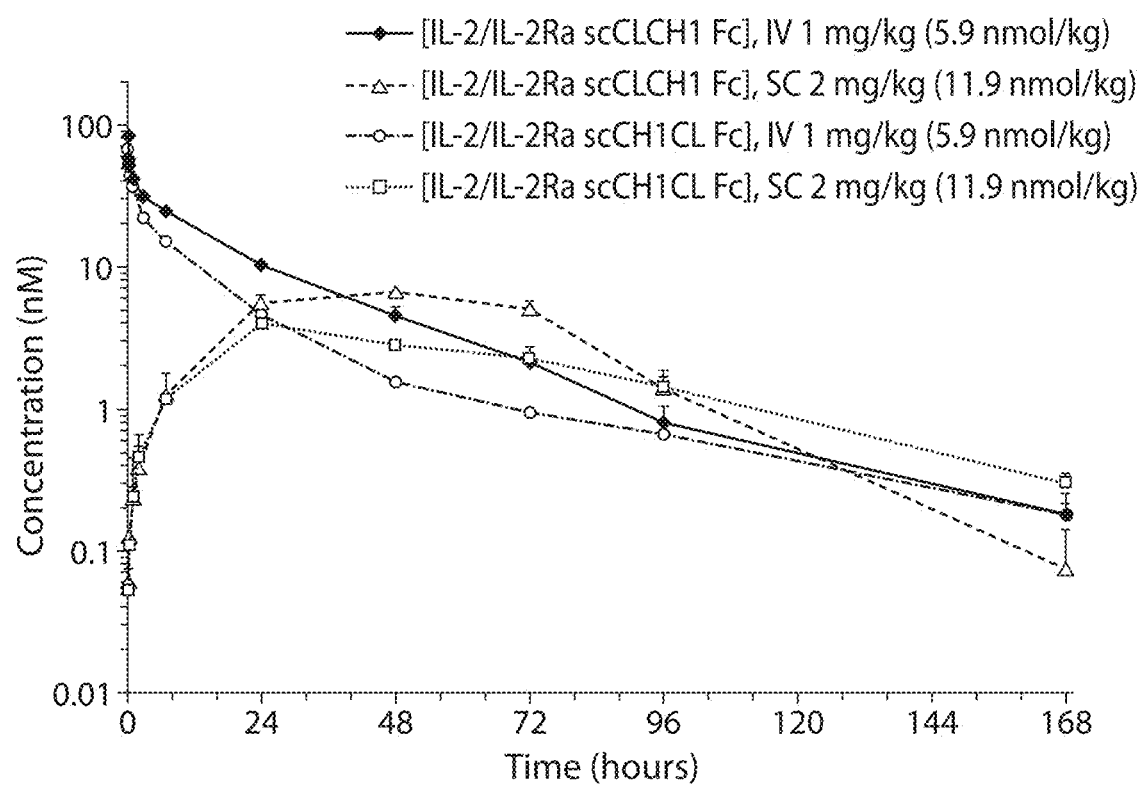
FIG. 16 is a graph showing the in vivo half-life in rats when intravenously and subcutaneously administered the IL-2/IL-2Rα single chain fusion proteins of the invention.

Single intravenous doses of 1 mg/kg IL-2/IL-2Rα scC$_L$C$_H$1-Fc and IL-2/IL-2Rα scC$_{H1}$C$_L$-Fc were administered into a tail vein of 3 rats. Blood samples were collected at 0.083, 0.25, 0.5, 1, 3, 8, 24, 48, 72, 96 and 168 hrs after administration of IL-2/IL-2Rα scC$_L$C$_H$1-Fc and IL-2/IL-2Rα scC$_{H1}$C$_L$-Fc. Single subcutaneous doses of 2 mg/kg IL-2/IL-2Rα scC$_L$C$_H$1-Fc and IL-2/IL-2Rα scC$_{H1}$C$_L$-Fc were administered into the interscapular region of 3 rats. Blood samples were collected at 0.25, 0.5, 1, 2, 6, 8, 24, 48, 72, 96 and 168 hrs after administration of IL-2/IL-2Rα scC$_L$C$_H$1-Fc and IL-2/IL-2Rα scC$_{H1}$C$_L$-Fc. Concentrations were measured using standard MSD techniques. Pharmacokinetic analysis was performed using non-compartmental modeling with WinNonlin software (Pharsight Corporation, Mountain View, Calif.). The pharmacokinetic parameter estimates derived from MSD data included maximum concentration (Cmax), area under the time versus concentration curve (AUC), and elimination half-life ($t_{1/2}$) (FIG. 16 and Table 5).

TABLE 5

| Test Article | Dosing Route | Dose (nmol/kg) | $T_{max}$ (h) | $C_{max}$ (nM) | $AUC_{0-\infty}$ (nM·h) | $t_{1/2}$ (h) | MRT (h) | CL (mL/h/kg) | Vd (mL/kg) | F (%) |
|---|---|---|---|---|---|---|---|---|---|---|
| IL-2/IL-2Ra scCLCH1 Fc | IV | 6 | 0.083 | 82.9 ± 12.0 | 876 ± 16.2 | 23.4 ± 4.4 | 25.6 ± 4.2 | 6.78 ± 0.125 | 174 ± 31.5 | |
| IL-2/IL-2Ra scCLCH1 Fc | SC | 12 | 48 | 6.67 ± 0.35 | 483 ± 56.9 | 15.3 ± 3.6 | 55.0 ± 1.7 | | | 28 |
| IL-2/IL-2Ra scCH1CL Fc | IV | 6 | 0.083 | 65.5 ± 7.6 | 505 ± 66.4 | 39.5 ± 4.7 | 26.3 ± 1.7 | 11.9 ± 1.6 | 313 ± 47.7 | |
| IL-2/IL-2Ra scCH1CL Fc | SC | 12 | (24, 48) | 3.36 ± 0.84 | 290 ± 1.0 | 32.9 ± 0.3 | 70.2 ± 8.8 | | | 29 |

Figure 17:
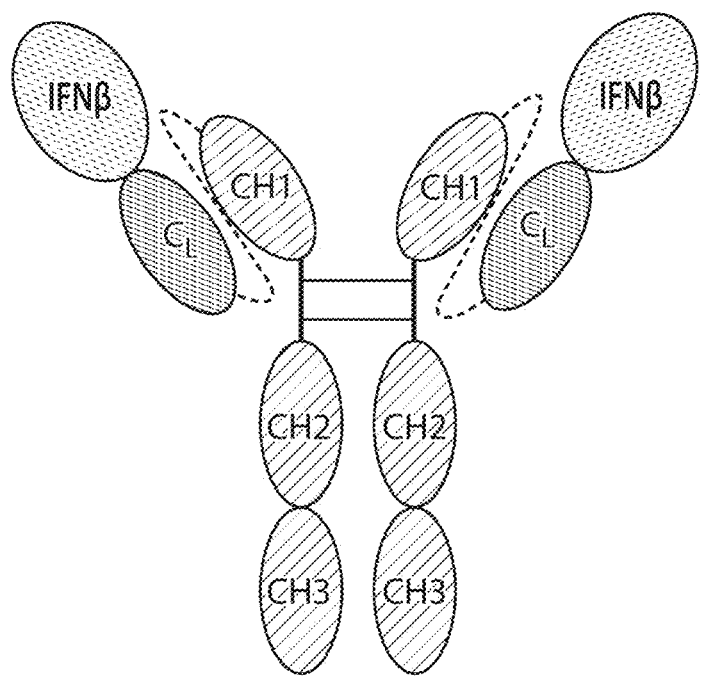
FIG. 17 is a diagram of an Fc fusion protein homodimer of two polypeptide chains, wherein in each polypeptide chain comprises as X, IFNβ which is then fused to the Fc region of an IgG1 antibody via the novel scCLCH1 linker of the invention.

Note:
mean ± SD for all parameters except median (min, max) for Tmax, n = 3 unless otherwise noted;
F = % ratio of dose normalized $AUC_{0-\infty}$ after SC vs IV Example 5: IFNβ
Design of IFNβ scC$_L$C$_H$1-Fc The IFNβ single chain fusion body molecule contains IFNβ (C17S) linked to the CL-CH1-Fc domain of the IgG1 heavy chain (FIG. 17). For expression in mammalian cells, the N-terminal leader sequence of SEQ ID NO: 10 was added to the protein of SEQ ID NO: 18.

Expression of IFNβ scC$_L$C$_H$1-Fc

The gene was synthetically synthesized and supplied in pcDNA3.1 expression vector (GeneArt), and transiently expressed in HEK293 cells using the Expi293 expression system (Life Technologies). The protein was purified using Protein A (GE Healthcare) with low pH elution and dialyzed against 2 L 1×PBS 2 times.

Figure 18:
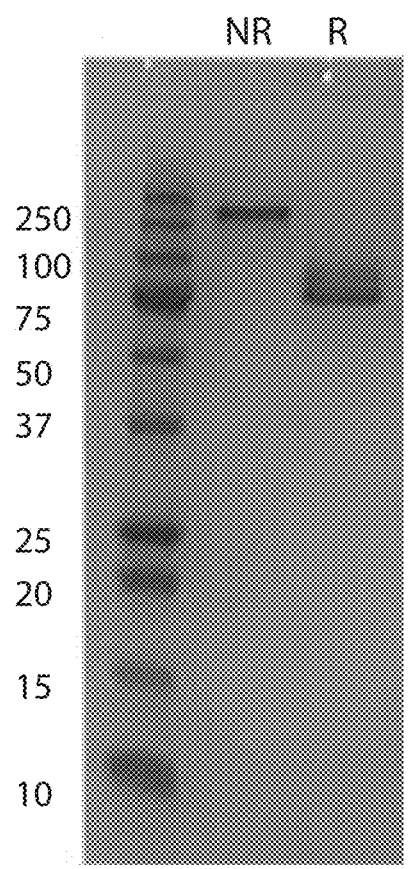
FIG. 18 is an SDS-PAGE showing expression of an Fc fusion protein comprising IFNβ fused to the Fc region of an IgG1 antibody via the novel scCLCH1 linker under reducing and non-reducing conditions.
Figure 19:
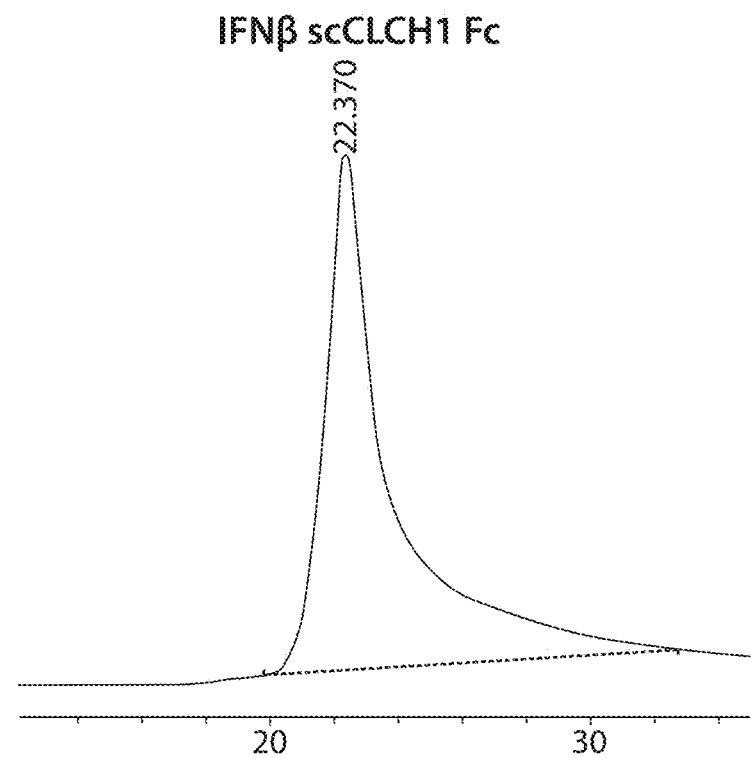
FIG. 19 is a chromatogram showing the characterization of IFNβ fused to the Fc region of an IgG1 antibody via the novel scCLCH1 linker by analytical gel filtration.

The molecule was analyzed by SDS PAGE gel under reducing and non-reducing conditions (FIG. 18). For reducing and non-reducing conditions, 5 ug of protein was loaded onto an Any kD gel (Invitrogen) with a Precision Plus Protein Kaleidoscope standard (Invitrogen) (MW range 10 kD-250 kD). The molecule was characterized by analytical gel filtration on a BioSuite Ultra High Resolution SEC column, 250 Å, 4 μm, 4.6 mm×300 mm (Waters). The column was equilibrated and run at 0.3 ml/min with 150 mM sodium phosphate pH 7.0 as a running buffer for all analyses. Purified samples (0.5 mg/ml) were injected (15 ul) and eluted with a run time of 60 min (FIG. 19).

Bioactivity of IFNβ scC$_L$C$_H$1-Fc

Figure 20:
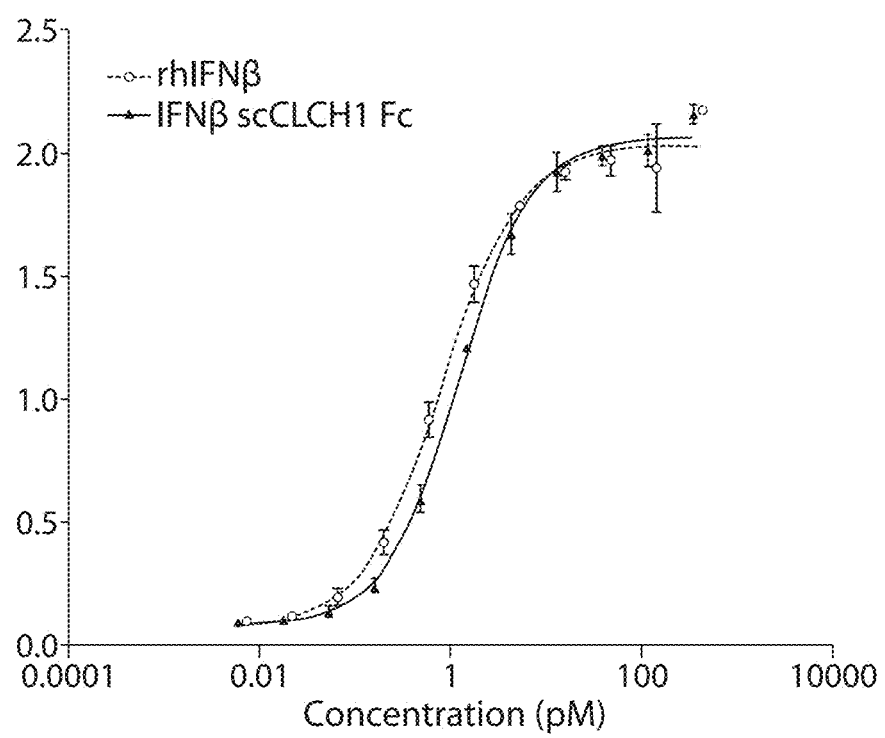
FIG. 20 is graph showing the activation of a reporter gene by the IFNβ fusion protein of the invention.

HEK-Blue™ IFNα/β cells (InvivoGen) are human embryonic kidney cells specifically designed to detect bioactive Type I IFNs in vitro by monitoring the activation of the ISGF3 pathway. The cell line expresses an inducible secreted embryonic alkaline phosphatase (SEAP) reporter gene under control of the IFNα/β inducible IFNα/β promoter. For the IFNβ agonist assay, HEK-Blue IFNα/β cells were plated at 50,000 cells/well in DMEM media containing 2 mM L-glutamine, 4.5 g/l glucose and 10% heat inactivated FBS (Gibco). Cells were incubated for 20 hours at 37° C., 5% $CO_2$ with varying concentrations of IFNβ scC$_L$C$_H$1-Fc or wtIFNβ (Peprotech). SEAP production was detected by adding QUANTI-Blue and incubating for 3 hours at 37° C., 5% $CO_2$ and read on a plate reader at 630 nm. IFNβ scC$_L$C$_H$1-Fc ($EC_{50}$=0.9 pM) and wtIFNβ ($EC_{50}$=0.6 pM) were active in a dose dependent fashion (FIG. 20).

Rat PK of IFNβ scC$_L$C$_H$1-Fc

Figure 21:
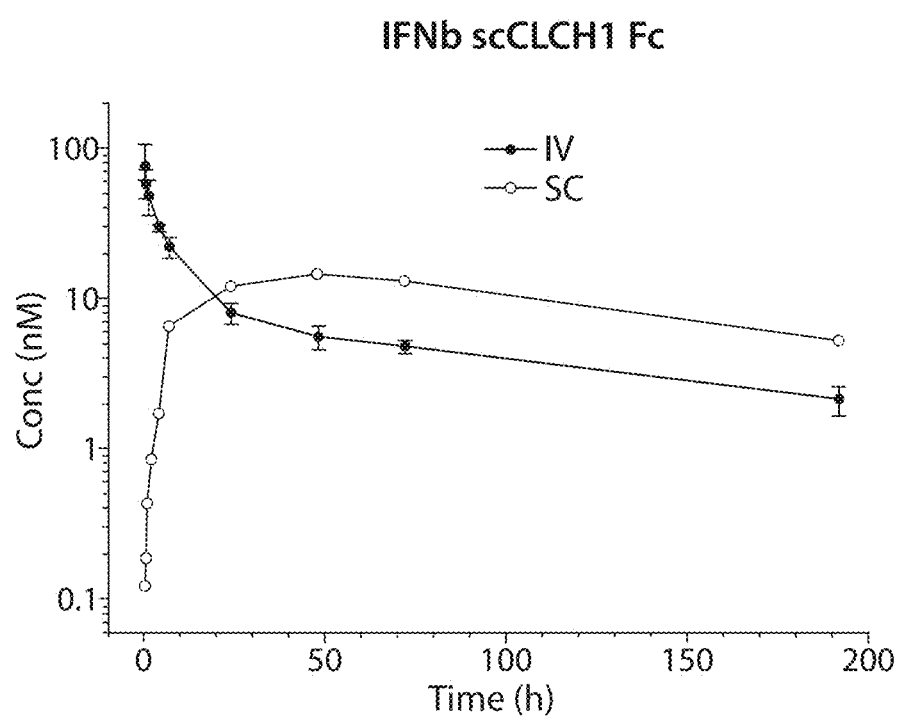
FIG. 21 is graph showing the mean concentration-time profile after IV (1.4 nMole/Kg and SC (3.6 nMole/kg) administration of the IFNβ fusion protein of the invention.

A single intravenous dose of 0.5 mg/kg IFNβ scC$_L$C$_H$1-Fc was administered into a surgically implanted jugular vein catheter of 3 rats. Blood samples were collected at 0.083, 0.25, 0.5, 1, 3, 8, 24, 48, 72, 96 and 168 hrs after administration of IFNβ scC$_L$C$_H$1-Fc. A Single subcutaneous dose of 1 mg/kg IFNβ scC$_L$C$_H$1-Fc was administered into the interscapular region of 3 rats. Blood samples were collected at 0.25, 0.5, 1, 2, 6, 8, 24, 48, 72, 96 and 168 hrs after administration of IFNβ scC$_L$C$_H$1-Fc. Concentrations were measured using standard MSD techniques. Pharmacokinetic analysis was performed using non-compartmental modeling with WinNonlin software (Pharsight Corporation, Mountain View, Calif.). The pharmacokinetic parameter estimates derived from MSD data included maximum concentration (Cmax), area under the time versus concentration curve (AUC), and elimination half-life ($t_{1/2}$) (FIG. 21 and Table 6).

TABLE 6

| Route | Dose (nMole/kg) | Animal ID | Cmax (nM) | Tmax (h) | Cmax/D (kg*nM/nmol) | $AUC_\infty$ (h*nM) | $AUC_\infty$/D (h*kg*nM/nmol) | CL (mL/h/kg) | $V_{ss}$ (mL/kg) | $t_{1/2}$ (h) | MRT (h) | % F (%) |
|---|---|---|---|---|---|---|---|---|---|---|---|---|
| IV | 1.4 | 67363 | 61.1 | 0.083 | 42.7 | 1320 | 921 | 1.09 | 111 | 87 | 100 | |
| | | 67364 | 54.7 | 0.083 | 38.2 | 1320 | 924 | 1.08 | 129 | 110 | 120 | |
| | | 67366 | 109 | 0.083 | 76.6 | 1790 | 1250 | 0.801 | 106 | 120 | 130 | |
| | | Mean | 75.1 | 0.083 | 52.5 | 1480 | 1030 | 0.991 | 115 | 100 | 120 | |
| | | SD | 30 | NA | 21 | 272 | 190 | 0.164 | 12.3 | 14 | 15 | |
| SC | 3.6 | 67367 | 16.4 | 48 | 4.57 | ND | ND | NA | NA | ND | ND | |
| | | 67369 | 12.8 | 24 | 3.57 | 2150 | 600 | NA | NA | 87 | 140 | |
| | | Mean | 14.6 | 36 | 4.07 | 2150 | 600 | NA | NA | 87 | 140 | 58.3 |
| | | SD | NA | NA | NA | NA | NA | NA | NA | NA | NA | |

Example 6: IL-10

Design of scIL-10:C$_L$:C$_H$1:Fc and scIL-10:C$_{H1}$:C$_L$:Fc

Figure 22A:
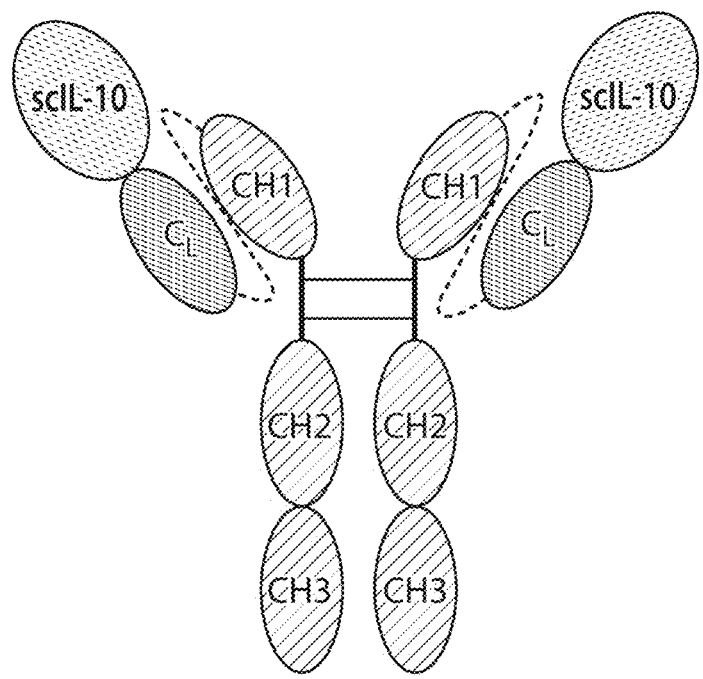
FIG. 22A is a diagram of an Fc fusion protein homodimer of two polypeptide chains, wherein in each polypeptide chain comprises as X, IL-10 which is then fused to the Fc region of an IgG1 antibody via the novel scCLCH1 linker.
Figure 22B:
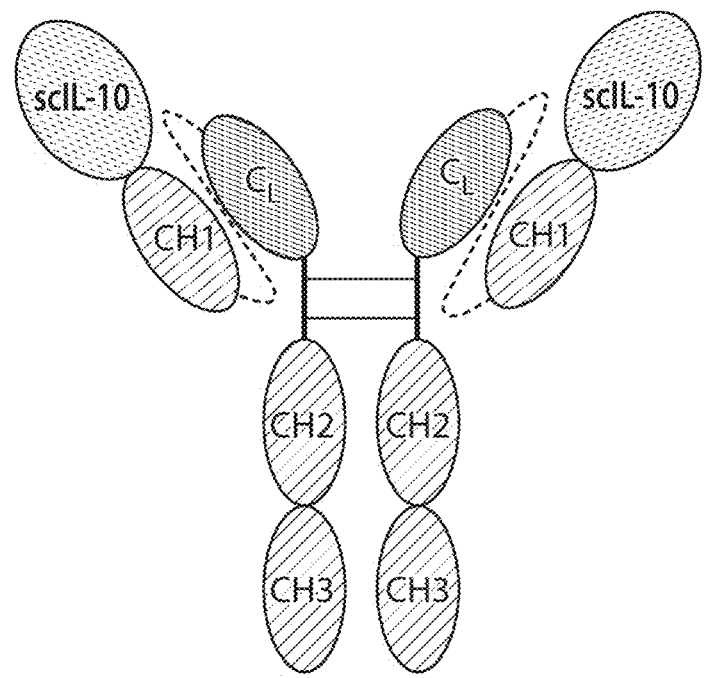
FIG. 22B is a diagram of an Fc fusion protein homodimer of two polypeptide chains, wherein in each polypeptide chain comprises as X, IL-10 which is then fused to the Fc region of an IgG1 antibody via the novel scCH1CL linker.

The scIL-10 single chain fusion body molecule contains a covalently linked IL-10 homodimer fusion protein linked to the CL-CH1-Fc domain or the CH1-CL-Fc of the IgG1 heavy chain (FIGS. 22A and 22B). The amino acid sequences of each molecule synthesized is found in Table 7.

TABLE 7

| Protein | Sequence |
|---|---|
| scIL-10:CL:CH1:Fc | MYRMQLLSCIALSLALVTNSSPGQGTQSENSCTHFPGNLPNMLRDLRDAFSRVKTFFQMKDQLDNL<br>LLKESLLEDFKGYLGCQALSEMIQFYLEEVMPQAENQDPDIKAHVNSLGENLKTLRLRLRRCHRFL<br>PCENKSKAVEQVKNAFNKLQEKGIYKAMSEFDIFINYIEAYMTMKIRNGGSGGGGSGGSPGQGTQS<br>ENSCTHFPGNLPNMLRDLRDAFSRVKTFFQMKDQLDNLLLKESLLEDFKGYLGCQALSEMIQFYLE<br>EVMPQAENQDPDIKAHVNSLGENLKTLRLRLRRCHRFLPCENKSKAVEQVKNAFNKLQEKGIYKAM<br>SEFDIFINYIEAYMTMKIRNGGGGSGGGGSRTVAAPSVFIFPPSDEQLKSGTASVVCLLNNFYPRE<br>AKVQWKVDNALQSGNSQESVTEQDKDSTYSLSSTLTLSKADYEKHKVYACEVTHQGLSSPVTKSFN<br>RGECGGGSGGGGSGGGGSGGGGSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKRVEPKSCDKTHT<br>CPPCPAPELLGGPSVFLFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLVTVDKSRWQQGNV<br>FSCSVMHEALHNHYTQKSLSLSPGK (SEQ ID NO: 23) |
| scIL-10:CH1:CL:Fc | MYRMQLLSCIALSLALVTNSSPGQGTQSENSCTHFPGNLPNMLRDLRDAFSRVKTFFQMKDQLDNL<br>LLKESLLEDFKGYLGCQALSEMIQFYLEEVMPQAENQDPDIKAHVNSLGENLKTLRLRLRRCHRFL<br>PCENKSKAVEQVKNAFNKLQEKGIYKAMSEFDIFINYIEAYMTMKIRNGGSGGGGSGGSPGQGTQS<br>ENSCTHFPGNLPNMLRDLRDAFSRVKTFFQMKDQLDNLLLKESLLEDFKGYLGCQALSEMIQFYLE<br>EVMPQAENQDPDIKAHVNSLGENLKTLRLRLRRCHRFLPCENKSKAVEQVKNAFNKLQEKGIYKAM |

TABLE 7-continued

| Protein | Sequence |
| --- | --- |
| | SEFDIFNINYIEAYMTMKIRNGGGGSGGGGSASTKGPSVFPLAPSSKSTSGGTAALGCLVKDYFPE<br>PVTVSWNSGALTSGVHTFPAVLQSSGLYSLSSVVTVPSSSLGTQTYICNVNHKPSNTKVDKRVGGG<br>GSGGGGSGGGGSGGGGSRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKSFNRGECGGSGGEPK<br>SCDKTHTCPPCPAPELLGGPSVFLFPPKPKDTLMISRTPEVTCVVVDVSHEDPEVKFNWYDGVEVH<br>NAKTKPREEQYNSTYRVVSVLTVLHQDWLNGKEYKCKVSNKALPAPIEKTISKAKGQPREPQVYTL<br>PPSREEMTKNQVSLTCLVKGFYPSDIAVEWESNGQPENNYKTTPPVLDSDGSFFLYSKLTVDKSRW<br>QQGNVFSCSVMHEALHNHYTQKSLSLSPGK (SEQ ID NO: 24) |
| scIL-10:Fc<br>(Control) | MYRMQLLSCIALSLALVTNSSPGQGTQSENSCTHFPGNLPNMLRDLRDAFSRVKTFFQMKDQLDNL<br>LLKESLLEDFKGYLGCQALSEMIQFYLEEVMPQAENQDPDIKAHVNSLGENLKTLRLRLRRCHRFL<br>PCENKSKAVEQVKNAFNKLQEKGIYKAMSEFDIFINYIEAYMTNKIRNGGSGGSPGQGTQSENSCT<br>HFPGNLPNMLRDLRDAFSRVKTFFQMKDQLDNLLLKESLLEDFKGYLGCQALSEMIQFYLEEVMPQ<br>AENQDPDIKAHVNSLGENLKTLRLRLRRCHRFLPCENKSKAVEQVKNAFNKLQEKGIYKAMSEFDI<br>FINYIEAYMTMKIRNEPKSSDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYKCKVSNKALPAPI<br>EKTISKAKGQPREPQVYTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPGK (SEQ ID NO: 25) |

Expression of scIL-10:$C_L$:$C_H1$:Fc and scIL-10:$C_{H1}$:$C_L$:Fc

The genes were synthetically synthesized and supplied in pcDNA3.1 expression vector (GeneArt), and transiently expressed in HEK293 cells using the Expi293 expression system (Life Technologies). Proteins were purified using Protein A (GE Healthcare) with low pH elution and dialyzed against 2 L 1×PBS 2 times.

Figure 23:
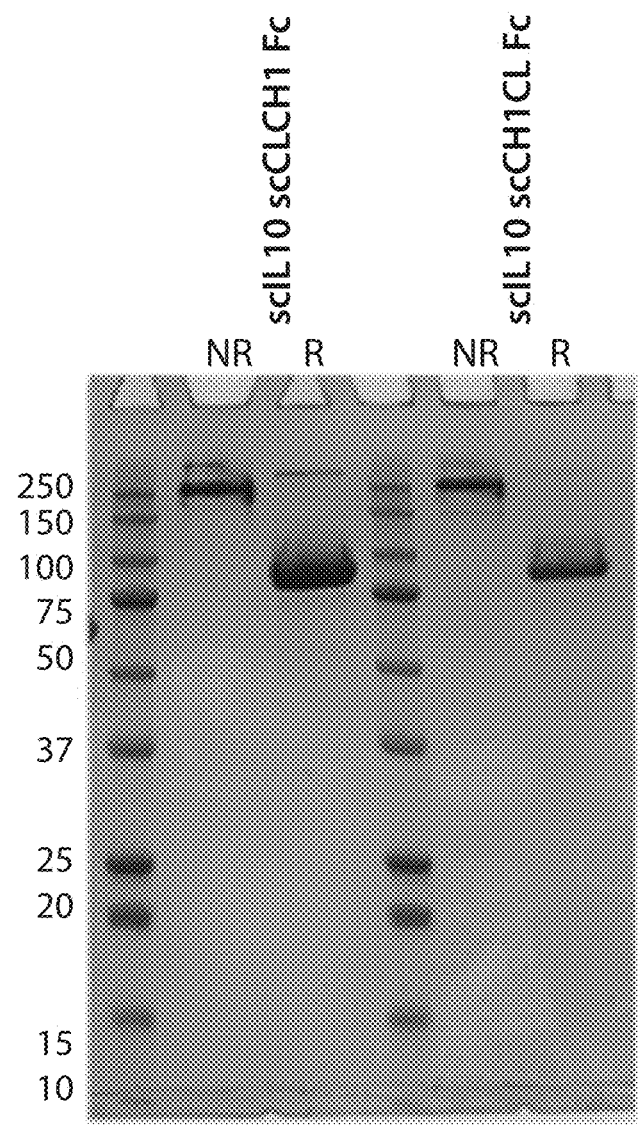
FIG. 23 is an SDS-PAGE showing expression of an Fc fusion protein comprising IL-10 fused to the Fc region of an IgG1 antibody via the novel scCLCH1 linker (left) or via the novel scCH1CL linker (right) under reducing and non-reducing conditions.
Figure 24A:
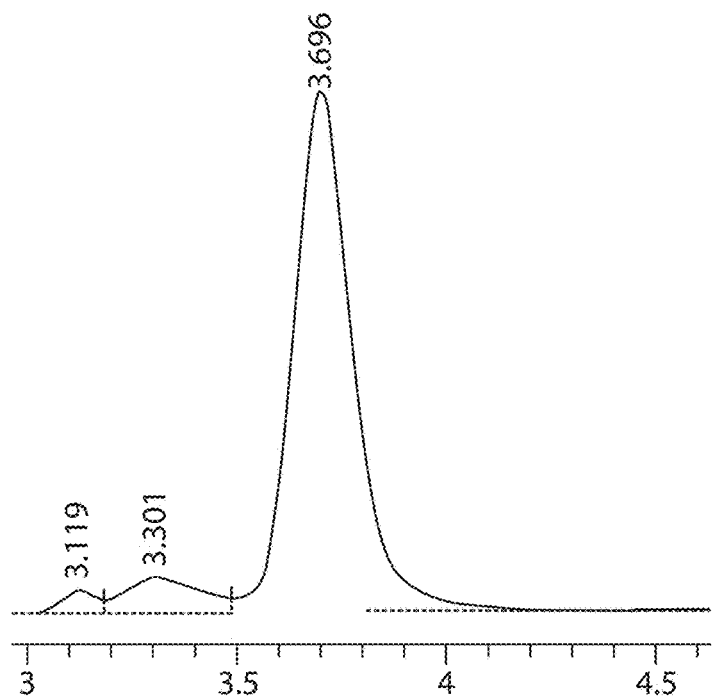
FIG. 24A is a chromatogram showing the characterization of the IL-10 fused to the Fc region of an IgG1 antibody via the novel scCLCH1 linker by analytical gel filtration.
Figure 24B:
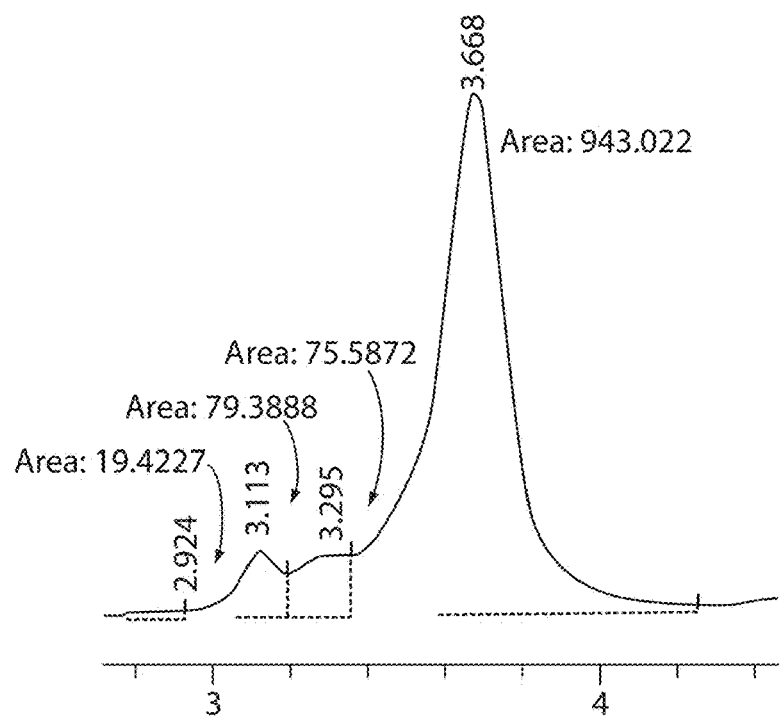
FIG. 24B is a chromatogram showing the characterization of the IL-10 fused to the Fc region of an IgG1 antibody via the novel scCH1CL linker by analytical gel filtration.

The molecules were analyzed by SDS PAGE gel under reducing and non-reducing conditions (FIG. 23). For reducing and non-reducing conditions, 2.5 ug of protein was loaded onto an Any kD gel (Invitrogen) with a Precision Plus Protein Kaleidoscope standard (Invitrogen) (MW range 10 kD-250 kD). The molecule was characterized by analytical gel filtration on an)(Bridge Protein BEH SEC column, 200 Å, 3.5 μm, 7.8 mm×150 mm (Waters). The column was equilibrated and run at 0.9 ml/min with 100 mM sodium phosphate pH 7.0 as a running buffer for all analyses. Purified samples (0.5 mg/ml) were injected (15 ul) and eluted with a run time of 15 min (FIGS. 24A and 24B).

Bioactivity of scIL-10:$C_L$:$C_H1$:Fc and scIL-10:$C_{H1}$:$C_L$:Fc

Figure 25:
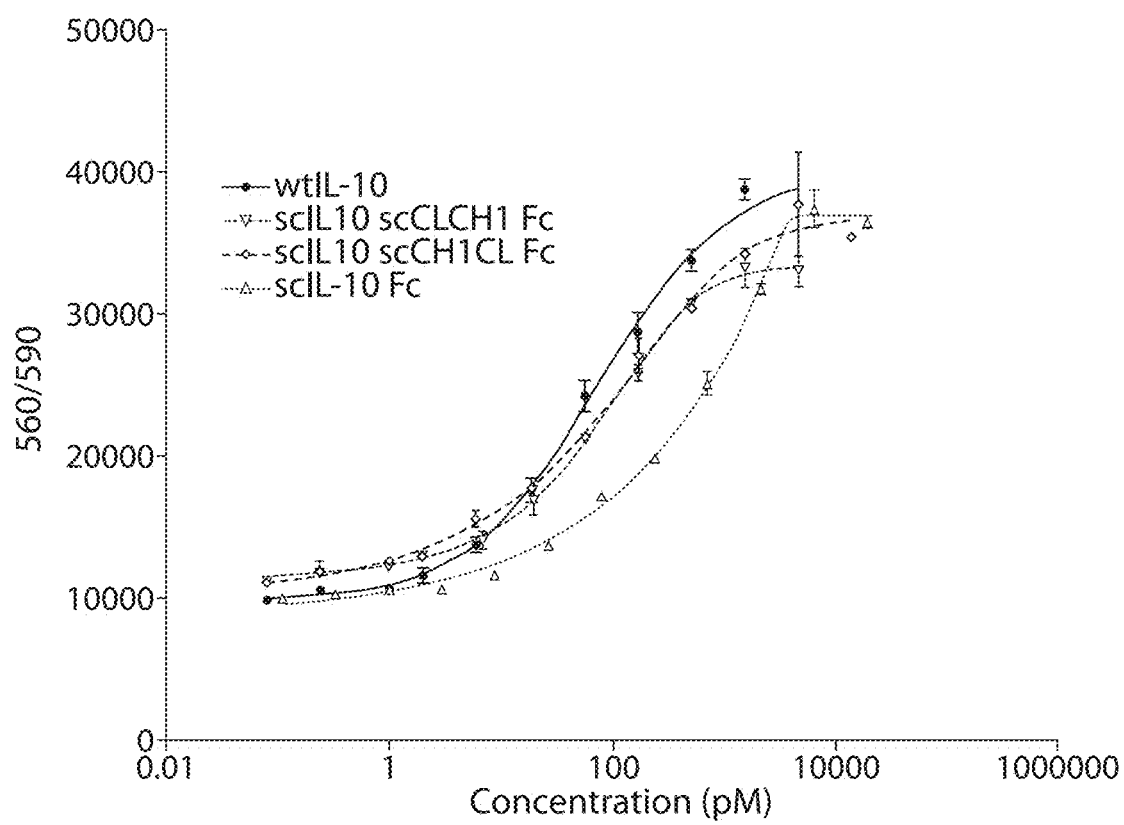
FIG. 25 is a graph showing stimulation of mouse mast cell line MC/9 by the IL-10 single chain fusion proteins of the invention as compared to the scIL-10 direct Fc fusion protein used as a control.

In vitro bioactivity was assessed by evaluating the ability of scIL-10:$C_L$:$C_H1$:Fc and scIL-10:$C_{H1}$:$C_L$:Fc to stimulate proliferation of the mouse mast cell line MC/9 (ATCC CRL-8306). The scIL-10 direct Fc fusion protein (scIL-10:Fc) was used as a control. For the assay, MC/9 cells were plated at 10,000 cells/well in DMEM media containing 10% heat inactivated fetal bovine serum, 2 mM glutamine and 0.05 mM 2-mercaptoethanol. Cells were incubated for 72 hours at 37° C., 5% $CO_2$ with varying concentrations of human IL-10 (R&D Systems), scIL-10:$C_L$:$C_H1$:Fc, scIL-10:$C_{H1}$:$C_L$:Fc or scIL-10:Fc. After 72 hours, the cells were stained with CellTiter-Blue (Promega) for 4 hours at 37° C., 5% $CO_2$ according to the manufacturer's protocol. Fluorescent measurements were taken at 560/590 nm. IL-10 ($EC_{50}$=75 pM), scIL-10:$C_L$:$C_H1$:Fc ($EC_{50}$=79 pM), scIL-10:$C_{H1}$:$C_L$:Fc ($EC_{50}$=93 pM) and scIL-10:Fc ($EC_{50}$=493 pM) were active in a dose dependent fashion (FIG. 25).

Mouse PK of scIL-10:$C_L$:$C_H1$:Fc and scIL-10:$C_{H1}$:$C_L$:Fc scIL-10:$C_L$:$C_H1$:Fc, scIL-10:$C_{H1}$:$C_L$:Fc, and scIL-10:Fc pharmacokinetics in mice were evaluated at a single intravenous doses of 0.5 mg/kg administered into tail vein and a single subcutaneous doses of 2.5 mg/kg administered into the interscapular region. Blood samples (n=3 samples/time point/fusion protein) were collected at 0.083, 0.5, 1, 4, 6, 24, 48, 96, 168, 192 and 216 hours after administration of scIL-10:$C_L$:$C_H1$:Fc, scIL-10:$C_{H1}$:$C_L$:Fc and scIL-10:Fc. For each time point/fusion protein/route of administration, serum was pooled and concentrations were measured using standard MSD techniques. Bioanalytical data was subjected to non-compartmental pharmacokinetic analysis using Phoenix WinNonlin 6.4 software. The pharmacokinetic parameter included standard pharmacokinetic parameters of maximum concentration ($C_{max}$), time to maximum concentration ($T_{max}$), area under the time versus concentration curve (AUC), mean residence time (MRT), elimination half-life (t1/2), clearance (CL), distribution volume at steady state ($V_{ss}$), and bioavailability (% F) were determined and reported in Tables 8 and 9.

TABLE 8

| Row ID | Compound | Dose (mg/kg) | Dose (~nMole/kg) | ROA | Cmax (nM) | Tmax (h) | Cmax/D (nM/D) | AUClast (h*nM) |
| --- | --- | --- | --- | --- | --- | --- | --- | --- |
| 1 | scIL-10:Fc | 0.5 | 3.93 | IV | 94.9 | 0.083 | 24.2 | 2080 |
| 2 | scIL-10:Fc | 2.5 | 19.63 | SC | 221 | 24 | 11.3 | 12700 |
| 3 | scIL-10:$C_L$:$C_H1$:Fc | 0.5 | 2.85 | IV | 140 | 0.083 | 49.2 | 2850 |
| 4 | scIL-10:$C_L$:$C_H1$:Fc | 2.5 | 14.25 | SC | 227 | 24 | 15.9 | 19500 |
| 5 | scIL-10:$C_{H1}$:$C_L$:Fc | 0.5 | 2.84 | IV | 115 | 0.083 | 40.5 | 1300 |
| 6 | scIL-10:$C_{H1}$:$C_L$:Fc | 2.5 | 14.2 | SC | 120 | 24 | 8.48 | 7570 |

TABLE 9

| Row ID | AUCinf (h*nM) | AUCinf/D (h*nM) | MRTinf (h) | t½ (h) | CL (mL/hr/kg) | Vss (mL/kg) | % F |
| --- | --- | --- | --- | --- | --- | --- | --- |
| 1 | 2170 | 552 | 33 | 21 | 1.811 | 59.57 | NA |
| 2 | 12700 | 649 | 46 | 11 | NA | NA | ~100 |
| 3 | 2850 | 999 | 30 | 7.8 | 1.001 | 29.56 | NA |
| 4 | 19500 | 1370 | 56 | 8.5 | NA | NA | ~100 |

TABLE 9-continued

| Row ID | AUCinf (h*nM) | AUCinf/D (h*nM) | MRTinf (h) | t½ (h) | CL (mL/hr/kg) | Vss (mL/kg) | % F |
|---|---|---|---|---|---|---|---|
| 5 | 1300 | 458 | 16 | 9.3 | 2.183 | 35.44 | NA |
| 6 | 7570 | 533 | 41 | 9.1 | NA | NA | ~100 |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred features thereof, it will be understood by those skilled in the art that various changes in form and details may be made therein without departing from the scope of the invention encompassed by the appended claims. It should also be understood that the various features of the invention described herein are not mutually exclusive and that features may be combined in whole or in part in accordance with the invention.

The invention claimed is:

1. A single chain fusion protein comprising amino acids 21-817 of SEQ ID NO: 23.

2. A homodimeric complex of the fusion protein of claim 1.

3. A single chain fusion protein comprising an amino acid sequence that is 99% identical to amino acids 21-817 of SEQ ID NO: 23.

4. A homodimeric complex of the fusion protein of claim 3.

5. A pharmaceutical composition comprising the fusion protein of claim 1.

6. A single chain fusion protein comprising amino acids 21-822 of SEQ ID NO: 24.

7. A homodimeric complex of the fusion protein of claim 6.

8. A single chain fusion protein comprising an amino acid sequence that is 99% identical to amino acids 21-822 of SEQ ID NO: 24.

9. A pharmaceutical composition comprising the fusion protein of claim 6.

10. An isolated or recombinant nucleic acid encoding the fusion protein of claim 1.

11. A recombinant vector comprising the nucleic acid of claim 10.

12. A host cell comprising the vector of claim 11.

13. An isolated or recombinant nucleic acid encoding the fusion protein of claim 6.

14. A recombinant vector comprising the nucleic acid of claim 13.

15. A host cell comprising the vector of claim 14.

* * * * *